United States Patent
Thevelein et al.

(10) Patent No.: US 11,692,187 B2
(45) Date of Patent: Jul. 4, 2023

(54) XYLOSE ISOMERASES THAT CONFER EFFICIENT XYLOSE FERMENTATION CAPABILITY TO YEAST

(71) Applicants: VIB vzw, Ghent (BE); Katholieke Universiteit Leuven, K.U. Leuven R&D, Leuven (BE); GlobalYeast N.V., Ghent (BE)

(72) Inventors: Johan Thevelein, Blanden (BE); Mekonnen Demeke, Leuven-Heverlee (BE); Maria Remedios Foulquié Moreno, Brussels (BE); Stijn De Graeve, Bertem (BE); Edgard Valdomiro Charles Belo, Heverlee (BE)

(73) Assignees: VIB vzw, Ghent (BE); Katholieke Universiteit Leuven, K.U. Leuven R&D, Leuven (BE); GlobalYeast N.V., Ghent (BE)

( * ) Notice: Subject to any disclaimer, the term of this patent is extended or adjusted under 35 U.S.C. 154(b) by 994 days.

(21) Appl. No.: 16/472,514

(22) PCT Filed: Dec. 21, 2017

(86) PCT No.: PCT/EP2017/084034
§ 371 (c)(1),
(2) Date: Jun. 21, 2019

(87) PCT Pub. No.: WO2018/115251
PCT Pub. Date: Jun. 28, 2018

(65) Prior Publication Data
US 2019/0316111 A1    Oct. 17, 2019

(30) Foreign Application Priority Data
Dec. 21, 2016  (EP) ..................... 16205614

(51) Int. Cl.
| | |
|---|---|
| *C12N 9/90* | (2006.01) |
| *C12N 15/87* | (2006.01) |
| *C12N 9/92* | (2006.01) |
| *C12P 5/02* | (2006.01) |
| *C12P 7/10* | (2006.01) |
| *C12P 7/16* | (2006.01) |
| *C12P 7/18* | (2006.01) |
| *C12P 7/40* | (2006.01) |
| *C12P 7/42* | (2006.01) |
| *C12P 7/46* | (2006.01) |
| *C12P 7/48* | (2006.01) |
| *C12P 7/6409* | (2022.01) |
| *C12P 13/04* | (2006.01) |
| *C12P 35/00* | (2006.01) |
| *C12N 15/90* | (2006.01) |

(52) U.S. Cl.
CPC ............... *C12N 9/92* (2013.01); *C12N 15/87* (2013.01); *C12N 15/905* (2013.01); *C12P 5/026* (2013.01); *C12P 7/10* (2013.01); *C12P 7/16* (2013.01); *C12P 7/18* (2013.01); *C12P 7/40* (2013.01); *C12P 7/42* (2013.01); *C12P 7/46* (2013.01); *C12P 7/48* (2013.01); *C12P 7/6409* (2013.01); *C12P 13/04* (2013.01); *C12P 35/00* (2013.01); *C12Y 503/01005* (2013.01)

(58) Field of Classification Search
CPC .................................. C12N 9/90; C12N 15/87
See application file for complete search history.

(56) References Cited

U.S. PATENT DOCUMENTS

| | | | |
|---|---|---|---|
| 8,906,656 B2 * | 12/2014 | Chen | C12N 9/92 435/161 |
| 2014/0256049 A1 * | 9/2014 | Chen | C12P 7/10 435/471 |
| 2014/0377813 A1 * | 12/2014 | Dragovic | C12P 1/02 435/119 |

FOREIGN PATENT DOCUMENTS

| | | |
|---|---|---|
| WO | 93/03159 A1 | 2/1993 |
| WO | 2003/062430 A1 | 7/2003 |
| WO | 2006/009434 A1 | 1/2006 |
| WO | 2010/074577 A1 | 7/2010 |
| WO | WO2012/175552 | 12/2012 |
| WO | WO2013/003219 | 1/2013 |
| WO | WO2013/017644 | 2/2013 |
| WO | WO2014/048863 | 4/2014 |
| WO | 2014/090930 A1 | 6/2014 |
| WO | WO2014/170330 | 10/2014 |
| WO | WO2015/086805 | 12/2014 |
| WO | WO2015/181169 | 12/2015 |
| WO | 2016/026954 A1 | 2/2016 |

(Continued)

OTHER PUBLICATIONS

Database UniProt; RecName: Full=Xylose isomerase; XP002778302, Jul. 24, 2013.

(Continued)

*Primary Examiner* — Maryam Monshipouri
(74) *Attorney, Agent, or Firm* — TraskBritt

(57) ABSTRACT

The present invention relates to novel nucleic acid sequences encoding bacterial xylose isomerases that upon transformation of a eukaryotic microbial host cell, such as yeast, to confer to the host cell the ability of isomerising xylose to xylulose. The nucleic acid sequences encode xylose isomerases that originate from bacteria such as *Eubacterium* sp., *Clostridium cellulosi* and others. The invention further relates to fermentation processes wherein the transformed host cells ferment a xylose-containing medium to produce ethanol or other fermentation products.

Figure 1:
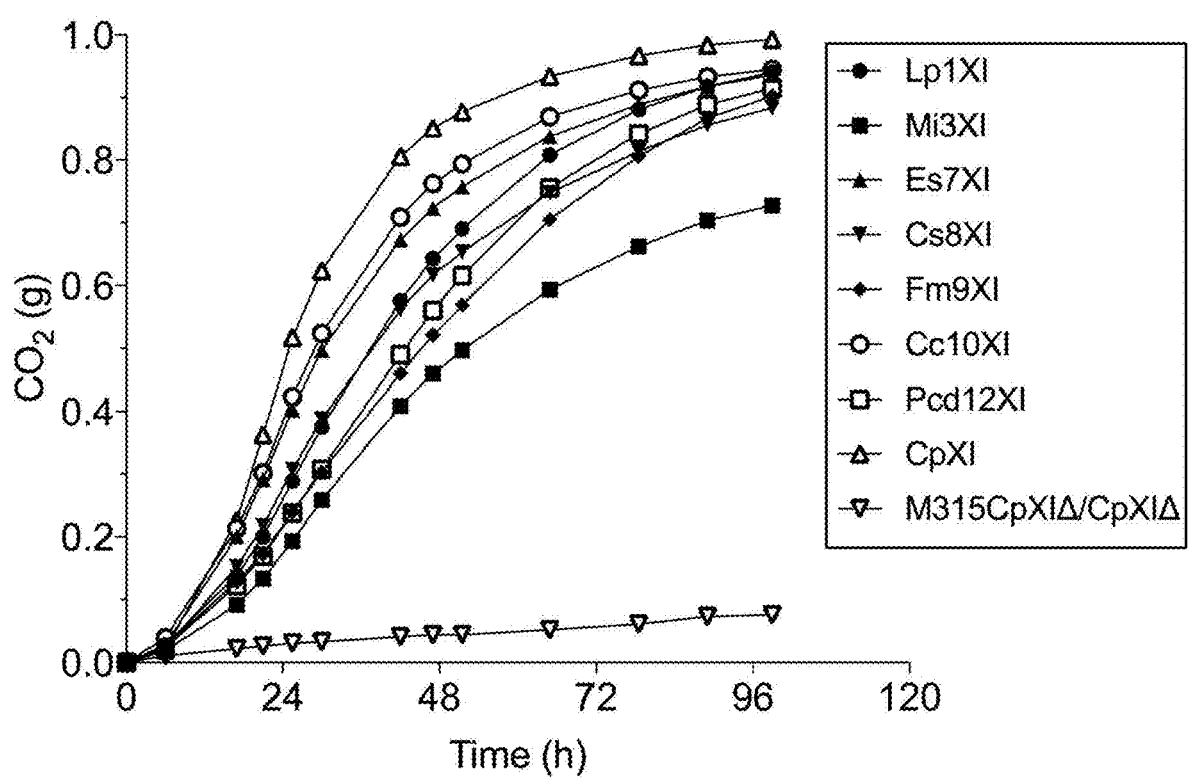

12 Claims, 5 Drawing Sheets
Specification includes a Sequence Listing.

(56) References Cited

FOREIGN PATENT DOCUMENTS

WO     WO2016/083397     6/2016

OTHER PUBLICATIONS

Database UniProt; RecName: Full=Xylose isomerase; UNIPROT:A0A078KPR4 Database accession No. A0A078KPR4; Oct. 29, 2014.

Database UniProt; RecName: Full=Xylose isomerase; UNIPR0T:M1MDX3 Database accession No. M1MDX3; May 1, 2013.

Austin et al. "*Mageeibacillus indolicus* gen. nov., sp. nov.: A novel bacterium isolated from the female genital tract" Anaerobe., vol. 32 (Apr. 2015) pp. 37-42.

Bettiga et al. "Comparing the xylose reductase/xylitol dehydrogenase and xylose isomerase pathways in arabinose and xylose fermenting *Saccharomyces cerevisiae* strains" Biotechnol Biofuels. 1:16 (Oct. 2008) pp. 1-8.

Bhosale et al. "Molecular and industrial aspects of glucose isomerase" Microbiol Rev. vol. 60, No. 2 (Jun. 1996) pp. 280-300.

Brat et al. "Functional Expression of a Bacterial Xylose Isomerase in *Saccharomyces cerevisiae*" Appl Environ Microbiol. 75(8) (Feb. 2009) pp. 2304-2311.

Çakar et al. "Evolutionary engineering of *Saccharomyces cerevisiae* for improved industrially important properties" FEMS Yeast Research, vol. 12, Issue 2 (Mar. 2012, pp. 171-182.

Demeke et al. "Combining inhibitor tolerance and D-xylose fermentation in industrial *Saccharomyces cerevisiae* for efficient lignocellulose-based bioethanol production" Biotechnol Biofuels, 26;6(1):120 (Aug. 2013) pp. 1-17.

Demeke et al. "Development of a D-xylose fermenting and inhibitor tolerant industrial *Saccharomyces cerevisiae* strain with high performance in lignocellulose hydrolysates using metabolic and evolutionary engineering" Biotechnol Biofuels, 6(1):89 (Jun. 2013) pp. 1-24.

Demeke et al. "Rapid Evolution of Recombinant *Saccharomyces cerevisiae* for Xylose Fermentation through Formation of Extrachromosomal Circular DNA" PLoS Genet., vol. 11(3) (Mar. 2015) pp. 1-24.

Gietz et al. "Studies on the transformation of intact yeast cells by the LiAc/SS-DNA/PEG procedure" Yeast. 11(4) (Apr. 1995) pp. 355-360.

Glanemann et al. "Disparity between changes in mRNA abundance and enzyme activity in Corynebacterium glutamicum: implications for DNA microarray analysis" Appl Microbiol Botechnol., 61(1) (Dec. 2002) pp. 61-68.

Hahn-Hägerdal et al. "Towards industrial pentose-fermenting yeast strains" Appl Microbiol Biotechnol. 74(5) (Apr. 2007) pp. 937-953 (Abstract).

Hector et al. "*Saccharomyces cerevisiae* engineered for xylose metabolism requires gluconeogenesis and the oxidative branch of the pentose phosphate pathway for aerobic xylose assimilation" Yeast, vol. 28, Issue 9 (Sep. 2011) pp. 645-660 (Abstract).

Henikoff et al. "Amino acid substitution matrices from protein blocks" Proc Natl Acad Sci U S A. Nov. 15, 1992;89(22): 10915-9.

Henrick et al. "Structures of D-xylose isomerase from Arthrobacter strain B3728 containing the inhibitors xylitol and D-sorbitol at 2.5 A and 2.3 A resolution, respectively" J Mol Biol., vol. 208, issue 1 (Jul. 1989) pp. 129-157.

Hou et al. "Fine-tuning of NADH oxidase decreases byproduct accumulation in respiration deficient xylose metabolic *Saccharomyces cerevisiae*" BMC Biotechnol. vol. 14 (Feb. 2014) pp. 1-10.

Jeppsson et al. "The expression of a Pichia stipitis xylose reductase mutant with higher KM for NADPH increases ethanol production from xylose in recombinant *Saccharomyces cerevisiae*" Biotechnol Bioeng. 93(4) (Mar. 2006) pp. 665-673 (Abstract).

Kuyper et al. High-level functional expression of a fungal xylose isomerase: the key to efficient ethanolic fermentation of xylose by *Saccharomyces cerevisiae*? FEMS Yeast Res., vol. 4, Issue 1 (Oct. 2003) pp. 69-78.

Lau et al. "Comparing the fermentation performance of *Escherichia coli* KO11, *Saccharomyces cerevisiae* 424A(LNH-ST) and Zymomonas mobilis AX101 for cellulosic ethanol production" Biotechnol Biofuels, 27;3:11 (May 2010) pp. 1-10.

Mumberg et al. "Yeast vectors for controlled expression of heterologous protein in different genetic backgrounds" Gene, vol. 156, No. 1 (May 1995) pp. 119-122.

Peng et al. "Bacterial xylose isomerases from the mammal gut Bacteroidetes cluster function in *Saccharomyces cerevisiae* for effective xylose fermentation" Microb Cell Factories. 14(1):70 (May 2015) pp. 1-14.

Träff et al. Deletion of the GRE3 aldose reductase gene and its influence on xylose metabolism in recombinant strains of *Saccharomyces cerevisiae* expressing the xylA and XKS1 genes Appl Environ Microbiol, vol. 67, No. 12 (Dec. 2001) pp. 5668-5674.

Vangrysperre et al. "Localization of the essential histidine and carboxylate group in D-xylose isomerases" Biochem J. Volumnbet 265, No. 3 (Feb. 1990) pp. 699-705.

Walfridsson et al. "Ethanolic fermentation of xylose with *Saccharomyces cerevisiae* harboring the Thermus thermophilus xylA gene, which expresses an active xylose (glucose) isomerase" Appl Environ Microbiol. vol. 62(Dec. 12, 1996) pp. 4648-4651.

Zaldivar et al. "Fuel ethanol production from lignocellulose: a challenge for metabolic engineering and process integration" Appl Microbiol Biotechnol. 56(1-2) (Jul. 2001) pp. 17-34.

\* cited by examiner

XYLOSE ISOMERASES THAT CONFER EFFICIENT XYLOSE FERMENTATION CAPABILITY TO YEAST

FIELD OF THE INVENTION

The present invention relates to the fields of microbiology and fermentation technology. In particular, the invention relates to nucleic acid sequences encoding xylose isomerases that upon transformation of a eukaryotic microbial host cell, such as yeast, to confer to the host cell the ability of isomerising xylose to xylulose. The invention further relates to fermentation processes wherein the transformed host cells ferment a pentose-containing medium to produce ethanol or other fermentation products.

BACKGROUND ART

The yeast *Saccharomyces cerevisiae* has been the primary organism of choice in industrial fermentation processes including alcoholic beverages and bioethanol production. The dominance of this organism in these industries is due to its superior properties such as high ethanol productivity and yield, high tolerance to ethanol and other inhibitors, and its excellent maintenance of viability during production, storage and transport. Additionally, since it is one of the most intensively studied microorganisms, numerous molecular tools are available for its genetic and physiological manipulation (1).

On the other hand, natural strains of *S. cerevisiae* are not useful in lignocellulose based ethanol industries. This is primarily due to their inability to metabolize pentose sugars, particularly xylose. Xylose is the second most abundant sugar in nature. It accounts for a third of the total sugar present in lignocellulosic biomass, such as agricultural and forest residues, and municipal solid waste. Hence, efficient utilization of xylose is crucial for lignocellulose based (second generation) bioethanol production (2).

There are several microorganisms that are able to naturally ferment xylose. However, unlike *S. cerevisiae*, those organisms do not have enough inherent robustness to cope with the harsh environments existing in industrial fermentations. Compared to *S. cerevisiae*, they are less tolerant to ethanol and to various growth and fermentation inhibitors such as organic acids, furan derivatives and phenolic compounds that are present in lignocellulosic hydrolysates (3). For that reason, much effort is being undertaken to engineer *S. cerevisiae* for efficient xylose fermentation, rather than endowing industrial robustness to naturally xylose utilizing micro-organisms.

Two different xylose utilization pathways have been engineered in yeast. The first pathway, called fungal pathway or the redox pathway, works by a two-step enzymatic conversion of xylose to xylulose. In the first step the NADPH-dependent enzyme Xylose Reductase (XR) reduces xylose to xylitol. Xylitol is subsequently oxidized to xylulose by the NAD-dependent Xylitol Dehydrogenase (XDH). Xylulose can then be phosphorylated to Xylulose-5-Phosphate by the native Xylulokinase. Though yeast strains expressing the fungal redox pathway can efficiently ferment xylose, they generally produce less ethanol per gram biomass, due to accumulation of xylitol as a by-product (4). The low ethanol yield and high xylitol accumulation are due to cofactor imbalance generated by the heterologous enzymes XR/XDH. A number of strategies has been applied to resolve the problem of cofactor imbalance. This includes modification of cofactor specificity of XR and XDH, and expression of heterologous transhydrogenases that catalyse the transfer of $H^+$ between NADPH and $NAD^+$ (5-7). Balancing cofactor usage in yeast expressing XR/XDH has shown good potential but until now, it could not eliminate production of xylitol as by-product. The yield of ethanol per amount of sugar consumed by such strains remains too low.

The second pathway works with a one-step conversion of xylose to xylulose using Xylose Isomerase (XI). This pathway alleviates the cofactor imbalance associated with the fungal redox pathway. The XI pathway is predominantly found in bacteria but also in some fungi. Many earlier attempts to express bacterial XI into yeast failed, or resulted in very low expression. The first functionally active bacterial XI expressed in yeast was encoded by the XylA gene from the thermophilic bacterium *Thermus thermophiles* (8). However, the optimal enzymatic activity was observed at 85° C., which is far above the optimum temperature at which yeasts can grow. Nevertheless, the recombinant strain was able to grow very slowly with xylose as sole carbon source. Later on, expression of an enzymatically active fungal XI from *Piromyces* sp. became a great success story (9). Subsequently, other XIs from various species of bacteria or fungi have been actively expressed in *S. cerevisiae* (10). However, the activity of those enzymes in yeast remains lower compared to that of *Piromyces* sp. XI. The first bacterial XI that showed very good enzymatic activity when expressed in yeast was the XI from the bacterial species *Clostridium phytofermentans*. This enzyme was less inhibited by xylitol as opposed to xylose isomerases from other bacterial species (11). However, in spite of the high in vitro enzyme activities of these XIs reported so far, the recombinant strains expressing these enzymes exhibited only slow growth and fermentation capacity with xylose. Further improvement by mutagenesis or adaptive evolution of the recombinant yeast is required to obtain an acceptable xylose fermentation capacity (12).

To date, there are hundreds of XylA sequences available in NCBI sequence databases. These sequences are a great tool to search for functionally active XIs originating from various species. In spite of the vast sequence information, only few XIs originating from several species of bacteria have been functionally expressed in yeast. Recently it was reported that most of the XIs actively expressed in yeast originate from the Bacteroidetes group living in the mammalian gut (10). A drawback of the XIs originating from the Bacteroidetes group is their strong inhibition by xylitol (11). However, many bacterial XIs other than those originating from the Bacteroidetes group cannot be functionally expressed in yeast and we can still not predict beforehand whether a particular XI will be functionally expressed in yeast or not.

There is, therefore, still a need in the art for nucleotide sequences encoding other xylose isomerases that may be used to transform host cells like *S. cerevisiae* to confer to them the ability of isomerising xylose to xylulose, so as to enable the use of thus transformed host cell in processes for the production of ethanol or other fermentation products by fermentation of pentose-containing feedstock.

SUMMARY OF THE INVENTION

In a first aspect the invention relates to a eukaryotic microbial cell comprising a nucleotide sequence, the expression of which confers to, or increases in the cell the ability to directly isomerise xylose into xylulose, wherein the nucleotide sequence encodes a polypeptide with xylose isomerase activity, which polypeptide comprises an amino acid sequence that has at least 68% sequence identity with the amino acid sequence of SEQ ID NO. 7. Preferably, the nucleotide sequence encodes an amino acid sequence that is obtainable from a bacterium of the genus *Eubacterium*, more preferably a bacterium of the species *Eubacterium* sp. CAG_180. A preferred cell according to the invention further comprises a second nucleotide sequence, the expression of which confers to, or increases in the cell the ability to directly isomerise xylose into xylulose, wherein the nucleotide sequence encodes a polypeptide with xylose isomerase activity, which polypeptide comprises an amino acid sequence that has at least 71% sequence identity with the amino acid sequence of SEQ ID NO. 10. Preferably the second nucleotide sequence encodes an amino acid sequence that is obtainable from a bacterium of the genus *Clostridium*, more preferably a bacterium of the species *Clostridium cellulosi*.

The eukaryotic microbial cell according to the invention preferably is a yeast or a filamentous fungus of a genus selected from the group consisting of *Saccharomyces, Kluyveromyces, Candida, Pichia, Schizosaccharomyces, Hansenula, Kloeckera, Schwanniomyces, Yarrowia, Kazachstania Naumovia, Aspergillus, Trichoderma, Humicola, Acremonium, Fusarium,* and *Penicillium*.

In one embodiment the eukaryotic microbial cell preferably is a yeast is capable of anaerobic alcoholic fermentation. Preferably, the yeast belongs to a *Saccharomyces* species selected from the group consisting of *S. cerevisiae, S. bayanus, S. bulderi, S. cervazzii, S. cariocanus, S. castellii, S. dairenensis, S. exiguus, S. kluyveri, S. kudriazevii, S. mikatae, S. paradoxus, S. pastorianus, S. turicensis* and *S. unisporus*.

In a eukaryotic microbial cell according to the invention, the nucleotide sequence encoding the polypeptide with xylose isomerase activity preferably is operably linked to a promoter that is insensitive to catabolite repression and/or that does not require xylose for induction.

The eukaryotic microbial cell according to the invention preferably comprises at least one genetic modification selected from: a) a genetic modification that increases the specific xylulose kinase activity; b) a genetic modification that increases the flux of the pentose phosphate pathway; and, c) a genetic modification that reduces unspecific aldose reductase activity in the cell. The cell further preferably comprises at least one genetic modification that results in a characteristic selected from the group consisting of: a) increased tolerance to ethanol; b) increased tolerance to acetic acid; c) reduced production of glycerol; d) increased xylose to ethanol fermentation rate; and, e) increased thermotolerance. More preferably in the cell: a) the genetic modification is a modification that introduces an allele of one or more of the ADE1, KIN3, MKT1, VPS70, SWS2 and APJ1 genes that confers increased tolerance to ethanol as described in WO 2012/175552 and WO 2014/170330; b) the genetic modification is a modification that introduces an allele of one or more of the GLO1, DOT5, CUP2 and HAA1 genes that confers increased tolerance to acetic acid as described in WO 2015/181169 and WO 2016/083397; c) the genetic modification is a modification that introduces a mutant SSK1 gene encoding a truncated ssk1 protein as described in WO 2014/048863; d) the genetic modification is a modification that introduces an allele of the NNK1 gene that confers an increased xylose to ethanol fermentation rate as described in WO 2015/086805; and, e) the genetic modification is overexpression of at least one of a gene encoding the Prp42 protein and a gene encoding the Smd2 protein.

In a preferred eukaryotic microbial cell according to the invention, the nucleotide sequence encoding the polypeptide with xylose isomerase activity is integrated into the genome of the cell.

A eukaryotic microbial cell according to the invention preferably is a cell of an industrial yeast strain or derived from an industrial yeast strain. The cell can be a diploid, aneuploid or polyploid cell.

In one embodiment, a eukaryotic microbial cell according to the invention is a cell that is improved in at least one industrially relevant phenotype by evolutionary engineering, wherein preferably the industrially relevant phenotype is xylose utilisation rate.

A eukaryotic microbial cell according to the invention further preferably has the ability to produce at least one fermentation product selected from the group consisting of ethanol, lactic acid, 3-hydroxy-propionic acid, acrylic acid, acetic acid, succinic acid, citric acid, amino acids, 1,3-propane-diol, ethylene, glycerol, butyric acid, caproate, butanol, glyoxylate, muconic acid, fatty alcohols, fatty acids, 1-lactam antibiotics and cephalosporins.

In a second aspect the invention pertain to a process for producing a fermentation product selected from the group consisting of ethanol, lactic acid, 3-hydroxy-propionic acid, acrylic acid, acetic acid, succinic acid, citric acid, amino acids, 1,3-propane-diol, ethylene, glycerol, butyric acid, caproate, butanol, glyoxylate, muconic acid, fatty alcohols, fatty acids, 1-lactam antibiotics and cephalosporins. The process preferably comprises the steps of: (a) fermenting a medium containing a source of xylose, and optionally a source of glucose, with a eukaryotic microbial cell according to the invention, whereby the cell ferments the xylose, and optionally the glucose, to the fermentation product, and optionally, (b) recovery of the fermentation product.

In a third aspect, the invention relates to the use of a eukaryotic microbial cell according to first aspect in a process according to the second aspect.

DESCRIPTION OF THE INVENTION

Definitions

The enzyme "xylose isomerase" (EC 5.3.1.5) is herein defined as an enzyme that catalyses the direct isomerisation of D-xylose into D-xylulose and vice versa. The enzyme is also known as a D-xylose ketoisomerase. Some xylose isomerases are also capable of catalysing the conversion between D-glucose and D-fructose and are therefore sometimes referred to as glucose isomerase. Xylose isomerases require magnesium as cofactor. Xylose isomerases of the invention may be further defined by their amino acid sequence as herein described below. Likewise xylose isomerases may be defined by the nucleotide sequences encoding the enzyme as well as by nucleotide sequences hybridising to a reference nucleotide sequence encoding a xylose isomerase as herein described below. A unit (U) of xylose isomerase activity is herein defined as the amount of enzyme producing 1 nmol of xylulose per minute, in a reaction mixture containing 50 mM phosphate buffer (pH 7.0), 10 mM xylose and 10 mM $MgCl_2$, at 37° C. Xylulose formed was determined by the method of Dische and Borenfreund (1951, J. Biol. Chem. 192: 583-587) or by HPLC as is known in the art.

The terms "homology", "sequence identity" and the like are used interchangeably herein. Sequence identity is herein defined as a relationship between two or more amino acid (polypeptide or protein) sequences or two or more nucleic acid (polynucleotide) sequences, as determined by comparing the sequences. In the art, "identity" also means the degree of sequence relatedness between amino acid or nucleic acid sequences, as the case may be, as determined by the match between strings of such sequences. "Similarity" between two amino acid sequences is determined by comparing the amino acid sequence and its conserved amino acid substitutes of one polypeptide to the sequence of a second polypeptide. "Identity" and "similarity" can be readily calculated by known methods.

"Sequence identity" and "sequence similarity" can be determined by alignment of two peptide or two nucleotide sequences using global or local alignment algorithms, depending on the length of the two sequences. Sequences of similar lengths are preferably aligned using a global alignment algorithms (e.g. Needleman Wunsch) which aligns the sequences optimally over the entire length, while sequences of substantially different lengths are preferably aligned using a local alignment algorithm (e.g. Smith Waterman). Sequences may then be referred to as "substantially identical" or "essentially similar" when they (when optimally aligned by for example the programs GAP or BESTFIT using default parameters) share at least a certain minimal percentage of sequence identity (as defined below). GAP uses the Needleman and Wunsch global alignment algorithm to align two sequences over their entire length (full length), maximizing the number of matches and minimizing the number of gaps. A global alignment is suitably used to determine sequence identity when the two sequences have similar lengths. Generally, the GAP default parameters are used, with a gap creation penalty=50 (nucleotides)/8 (proteins) and gap extension penalty=3 (nucleotides)/2 (proteins). For nucleotides the default scoring matrix used is nwsgapdna and for proteins the default scoring matrix is Blosum62 (Henikoff & Henikoff, 1992, PNAS 89, 915-919). Sequence alignments and scores for percentage sequence identity may be determined using computer programs, such as the GCG Wisconsin Package, Version 10.3, available from Accelrys Inc., 9685 Scranton Road, San Diego, Calif. 92121-3752 USA, or using open source software, such as the program "needle" (using the global Needleman Wunsch algorithm) or "water" (using the local Smith Waterman algorithm) in EmbossWIN version 2.10.0, using the same parameters as for GAP above, or using the default settings (both for 'needle' and for 'water' and both for protein and for DNA alignments, the default Gap opening penalty is 10.0 and the default gap extension penalty is 0.5; default scoring matrices are Blossum62 for proteins and DNAFull for DNA). When sequences have a substantially different overall lengths, local alignments, such as those using the Smith Waterman algorithm, are preferred.

Alternatively percentage similarity or identity may be determined by searching against public databases, using algorithms such as FASTA, BLAST, etc. Thus, the nucleic acid and protein sequences of the disclosure can further be used as a "query sequence" to perform a search against public databases to, for example, identify other family members or related sequences. Such searches can be performed using the BLASTn and BLASTx programs (version 2.0) of Altschul, et al. (1990) J. Mol. Biol. 215:403-10. BLAST nucleotide searches can be performed with the NBLAST program, score=100, wordlength=12 to obtain nucleotide sequences homologous to oxidoreductase nucleic acid molecules of the disclosure. BLAST protein searches can be performed with the BLASTx program, score=50, wordlength=3 to obtain amino acid sequences homologous to protein molecules of the invention disclosure. To obtain gapped alignments for comparison purposes, Gapped BLAST can be utilized as described in Altschul et al., (1997) Nucleic Acids Res. 25(17): 3389-3402. When utilizing BLAST and Gapped BLAST programs, the default parameters of the respective programs (e.g., BLASTx and BLASTn) can be used. See the homepage of the National Center for Biotechnology Information at www.ncbi.nlm.nih.gov/.

Optionally, in determining the degree of amino acid similarity, the skilled person may also take into account so-called "conservative" amino acid substitutions, as will be clear to the skilled person. Conservative amino acid substitutions refer to the interchangeability of residues having similar side chains. Examples of classes of amino acid residues for conservative substitutions are given in the Tables below.

| | |
|---|---|
| Acidic Residues | Asp (D) and Glu (E) |
| Basic Residues | Lys (K), Arg (R), and His (H) |
| Hydrophilic Uncharged Residues | Ser (S), Thr (T), Asn (N), and Gln (Q) |
| Aliphatic Uncharged Residues | Gly (G), Ala (A), Val (V), Leu (L), and Ile (I) |
| Non-polar Uncharged Residues | Cys (C), Met (M), and Pro (P) |
| Aromatic Residues | Phe (F), Tyr (Y), and Trp (W) |

Alternative conservative amino acid residue substitution classes.

| | | | |
|---|---|---|---|
| 1 | A | S | T |
| 2 | D | E | |
| 3 | N | Q | |
| 4 | R | K | |
| 5 | I | L | M |
| 6 | F | Y | W |

Alternative Physical and Functional Classifications of Amino Acid Residues.

| | |
|---|---|
| Alcohol group-containing residues | S and T |
| Aliphatic residues | I, L, V, and M |
| Cycloalkenyl-associated residues | F, H, W, and Y |
| Hydrophobic residues | A, C, F, G, H, I, L, M, R, T, V, W, and Y |
| Negatively charged residues | D and E |
| Polar residues | C, D, E, H, K, N, Q, R, S, and T |
| Positively charged residues | H, K, and R |
| Small residues | A, C, D, G, N, P, S, T, and V |
| Very small residues | A, G, and S |
| Residues involved in turn formation | A, C, D, E, G, H, K, N, Q, R, S, P and T |
| Flexible residues | Q, T, K, S, G, P, D, E, and R |

Nucleotide sequences encoding xylose isomerases of the invention may also be defined by their capability to hybridise with the nucleotide sequences of encoding xylose isomerases as exemplified herein, under moderate, or preferably under stringent hybridisation conditions. Stringent hybridisation conditions are herein defined as conditions that allow a nucleic acid sequence of at least about 25, preferably about 50 nucleotides, 75 or 100 and most preferably of about 200 or more nucleotides, to hybridise at a temperature of about 65° C. in a solution comprising about 1 M salt, preferably 6×SSC or any other solution having a comparable ionic strength, and washing at 65° C. in a solution comprising about 0.1 M salt, or less, preferably 0.2×SSC or any other solution having a comparable ionic strength. Preferably, the hybridisation is performed overnight, i.e. at least for 10 hours and preferably washing is performed for at least one hour with at least two changes of the washing solution. These conditions will usually allow the specific hybridisation of sequences having about 90% or more sequence identity.

Moderate conditions are herein defined as conditions that allow a nucleic acid sequences of at least 50 nucleotides, preferably of about 200 or more nucleotides, to hybridise at a temperature of about 45° C. in a solution comprising about 1 M salt, preferably 6×SSC or any other solution having a comparable ionic strength, and washing at room temperature in a solution comprising about 1 M salt, preferably 6×SSC or any other solution having a comparable ionic strength. Preferably, the hybridisation is performed overnight, i.e. at least for 10 hours, and preferably washing is performed for at least one hour with at least two changes of the washing solution. These conditions will usually allow the specific hybridisation of sequences having up to 50% sequence identity. The person skilled in the art will be able to modify these hybridisation conditions in order to specifically identify sequences varying in identity between 50% and 90%.

A "nucleic acid construct" or "nucleic acid vector" is herein understood to mean a man-made nucleic acid molecule resulting from the use of recombinant DNA technology. The term "nucleic acid construct" therefore does not include naturally occurring nucleic acid molecules although a nucleic acid construct may comprise (parts of) naturally occurring nucleic acid molecules. The terms "expression vector" or expression construct" refer to nucleotide sequences that are capable of affecting expression of a gene in host cells or host organisms compatible with such sequences. These expression vectors typically include at least suitable transcription regulatory sequences and optionally, 3' transcription termination signals. Additional factors necessary or helpful in effecting expression may also be present, such as expression enhancer elements. The expression vector will be introduced into a suitable host cell and be able to effect expression of the coding sequence in an in vitro cell culture of the host cell. The expression vector will be suitable for replication in the host cell or organism of the invention.

As used herein, the term "promoter" or "transcription regulatory sequence" refers to a nucleic acid fragment that functions to control the transcription of one or more coding sequences, and is located upstream with respect to the direction of transcription of the transcription initiation site of the coding sequence, and is structurally identified by the presence of a binding site for DNA-dependent RNA polymerase, transcription initiation sites and any other DNA sequences, including, but not limited to transcription factor binding sites, repressor and activator protein binding sites, and any other sequences of nucleotides known to one of skill in the art to act directly or indirectly to regulate the amount of transcription from the promoter. A "constitutive" promoter is a promoter that is active in most tissues under most physiological and developmental conditions. An "inducible" promoter is a promoter that is physiologically or developmentally regulated, e.g. by the application of a chemical inducer.

The term "selectable marker" is a term familiar to one of ordinary skill in the art and is used herein to describe any genetic entity which, when expressed, can be used to select for a cell or cells containing the selectable marker. The term "reporter" may be used interchangeably with marker, although it is mainly used to refer to visible markers, such as green fluorescent protein (GFP). Selectable markers may be dominant or recessive or bidirectional.

As used herein, the term "operably linked" refers to a linkage of polynucleotide elements in a functional relationship. A nucleic acid is "operably linked" when it is placed into a functional relationship with another nucleic acid sequence. For instance, a transcription regulatory sequence is operably linked to a coding sequence if it affects the transcription of the coding sequence. Operably linked means that the DNA sequences being linked are typically contiguous and, where necessary to join two protein encoding regions, contiguous and in reading frame.

The terms "protein" or "polypeptide" are used interchangeably and refer to molecules consisting of a chain of amino acids, without reference to a specific mode of action, size, 3-dimensional structure or origin.

"Fungi" (singular fungus) are herein understood as heterotrophic eukaryotic microorganism that digest their food externally, absorbing nutrient molecules into their cells. Fungi are a separate kingdom of eukaryotic organisms and include yeasts, molds, and mushrooms. The terms fungi, fungus and fungal as used herein thus expressly includes yeasts as well as filamentous fungi.

The term "gene" means a DNA fragment comprising a region (transcribed region), which is transcribed into an RNA molecule (e.g. an mRNA) in a cell, operably linked to suitable regulatory regions (e.g. a promoter). A gene will usually comprise several operably linked fragments, such as a promoter, a 5' leader sequence, a coding region and a 3'nontranslated sequence (3'end) comprising a polyadenylation site. "Expression of a gene" refers to the process wherein a DNA region which is operably linked to appropriate regulatory regions, particularly a promoter, is transcribed into an RNA, which is biologically active, i.e. which is capable of being translated into a biologically active protein or peptide.

The term "homologous" when used to indicate the relation between a given (recombinant) nucleic acid or polypeptide molecule and a given host organism or host cell, is understood to mean that in nature the nucleic acid or polypeptide molecule is produced by a host cell or organisms of the same species, preferably of the same variety or strain. If homologous to a host cell, a nucleic acid sequence encoding a polypeptide will typically (but not necessarily) be operably linked to another (heterologous) promoter sequence and, if applicable, another (heterologous) secretory signal sequence and/or terminator sequence than in its natural environment. It is understood that the regulatory sequences, signal sequences, terminator sequences, etc. may also be homologous to the host cell. In this context, the use of only "homologous" sequence elements allows the construction of "self-cloned" genetically modified organisms (GMO's) (self-cloning is defined herein as in European Directive 98/81/EC Annex II). When used to indicate the relatedness of two nucleic acid sequences the term "homologous" means that one single-stranded nucleic acid sequence may hybridize to a complementary single-stranded nucleic acid sequence. The degree of hybridization may depend on a number of factors including the amount of identity between the sequences and the hybridization conditions such as temperature and salt concentration as discussed later.

The term "heterologous" when used with respect to a nucleic acid (DNA or RNA) or protein refers to a nucleic acid or protein that does not occur naturally as part of the organism, cell, genome or DNA or RNA sequence in which it is present, or that is found in a cell or location or locations in the genome or DNA or RNA sequence that differ from that in which it is found in nature. Heterologous nucleic acids or proteins are not endogenous to the cell into which it is introduced, but has been obtained from another cell or synthetically or recombinantly produced. Generally, though not necessarily, such nucleic acids encode proteins that are not normally produced by the cell in which the DNA is transcribed or expressed. Similarly exogenous RNA encodes for proteins not normally expressed in the cell in which the exogenous RNA is present. Heterologous nucleic acids and proteins may also be referred to as foreign nucleic acids or proteins. Any nucleic acid or protein that one of skill in the art would recognize as heterologous or foreign to the cell in which it is expressed is herein encompassed by the term heterologous nucleic acid or protein. The term heterologous also applies to non-natural combinations of nucleic acid or amino acid sequences, i.e. combinations where at least two of the combined sequences are foreign with respect to each other.

DESCRIPTION OF EMBODIMENTS

To date a vast amount of xylose isomerase amino acid sequences are publicly available in Genbank and other sequence databases. Among them are few amino acid sequences of xylose isomerases that are known for the ability of functional expression in yeasts, including e.g. xylose isomerases from anaerobic fungi like *Piromyces*, from the Bacteroidetes group living in the mammalian gut, as well as a bacterial xylose isomerases from the species *Clostridium phytofermentans*. The present inventors have surprisingly found amino acid sequences of xylose isomerases that are not related to the *Piromyces*, Bacteroidetes and *C. phytofermentans* enzymes—in the sense that most of them share less than 70% amino acid sequence identity with the amino acid sequences of the *Piromyces* (PiXI; SEQ ID NO: 18) and *C. phytofermentans* (CpXI; SEQ ID NO: 17) enzymes (see Table 1), and that nonetheless have the ability of functional (i.e. active) expression in yeasts.

Functional expression of a xylose isomerase in a yeast is herein understood as expression of a codon-optimised coding sequence for the xylose isomerase from a glycolytic promoter on a 2p-based plasmid in a *S. cerevisiae* host strain, which expression allows the detectable growth of the yeast on xylose as sole carbon source, preferably under anaerobic conditions with production of ethanol at the expense of xylose, more preferably with at least one of a growth rate, biomass and ethanol yield that is at least 10, 20, 50 or 80% of that achieved with a codon-optimised sequence coding for the *Piromyces* xylose isomerase (with amino acid sequence of SEQ ID NO: 18) under otherwise identical conditions. The *S. cerevisiae* host strain preferably is a host strain modified for growth on xylose by overexpression of xylulose kinase (XKS1) and all the genes of the pentose phosphate pathway (PPP), such as e.g. the strain M315CpXIΔ/CpXIΔ (see Examples). Preferably, functional expression is expression that allows the detectable growth of the host strain on xylose as sole carbon source at a temperature which is lower than 35, 33, 30 or 28° C. and at a temperature which is higher than 20, 22, or 25° C.

TABLE 1

Sequence identity of amino acid sequences of xylose isomerases in comparison to the amino acid sequence of *Piromyces* sp. XI (PiXI) and *C. phytofermentans* XI (CpXI).

| Source of xylose isomerase | % identity to PiXI | % identity to CpXI | Functional expression in yeast | SEQ ID NO. | Code |
|---|---|---|---|---|---|
| *Lachnoclostridium phytofermentans* | 54.99 | 96.12 | + | 1 | Lp1XI |
| *Clostridium algidicarnis* | 53.83 | 72.60 | + | 2 | Ca2XI |
| *Mageeibacillus indolicus* | 53.02 | 69.35 | + | 3 | Mi3XI |
| *Ruminococcus* sp. NK3A76 | 52.19 | 68.64 | − | 4 | Rs4XI |
| *Epulopiscium* sp. 'N.t. morphotype B | 52.94 | 67.28 | + | 5 | Es5XI |
| *Alkaliphilus metalliredigens* | 52.76 | 65.53 | + | 6 | Am6XI |
| *Eubacterium* sp. CAG_180 | 54.38 | 65.44 | + | 7 | Es7XI |
| *Clostridium saccharoperbutylacetonicum* | 53.23 | 64.61 | + | 8 | Cs8XI |
| *Fusobacterium mortiferum* | 51.96 | 65.67 | + | 9 | Fm9XI |
| [*Clostridium*] *cellulosi* | 50.69 | 64.84 | + | 10 | Cc10XI |
| *Cellulosilyticum lentocellum* | 53.35 | 64.53 | + | 11 | Cl11XI |
| *Peptoclostridium difficile* | 54.04 | 62.93 | + | 12 | Pcd12XI |
| (Pepto)*clostridium difficile* NAP08 | 54.50 | 62.70 | − | 13 | Cd13XI |
| *Caldicellulosiruptor acetigenus* | 50.35 | 61.75 | − | 14 | Ca14XI |
| *Agrobacterium tumefaciens* | 49.89 | 52.50 | − | 15 | At15XI |
| *Burkholderia cenocepacia* | 49.32 | 51.70 | − | 16 | Bc16XI |

In a first aspect the invention relates to a transformed host cell that has the ability of isomerising xylose to xylulose. The ability of isomerising xylose to xylulose is conferred to the host cell by transformation of the host cell with a nucleic acid construct comprising a nucleotide sequence encoding a xylose isomerase. The transformed host cell's ability to isomerise xylose into xylulose is understood to mean the direct isomerisation of xylose, in a single reaction catalysed by a xylose isomerase, to xylulose, as opposed to the two step conversion of xylose into xylulose via a xylitol intermediate as catalysed by xylose reductase and xylitol dehydrogenase, respectively.

In one embodiment the nucleotide sequence encoding the xylose isomerase is selected from the group consisting of:
(a) a nucleotide sequence encoding a polypeptide with xylose isomerase activity, which polypeptide comprises an amino acid sequence that has at least 65.5, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 95, 96, 97, 98, or 99% sequence identity with the amino acid sequence of SEQ ID NO. 7 (*Eubacterium* sp. CAG_180);

(b) a nucleotide sequence encoding a polypeptide with xylose isomerase activity, which polypeptide comprises an amino acid sequence that has at least 64.9, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 95, 96, 97, 98, or 99% sequence identity with the amino acid sequence of SEQ ID NO. 10 ([*Clostridium*] *cellulosi*);

(c) a nucleotide sequence encoding a polypeptide with xylose isomerase activity, which polypeptide comprises an amino acid sequence that has at least 64.7, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 95, 96, 97, 98, or 99% sequence identity with the amino acid sequence of SEQ ID NO. 8 (*Clostridium saccharoperbutylacetonicum*);

(d) a nucleotide sequence encoding a polypeptide with xylose isomerase activity, which polypeptide comprises an amino acid sequence that has at least 64.6, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 95, 96, 97, 98, or 99% sequence identity with the amino acid sequence of SEQ ID NO. 11 (*Cellulosilyticum lentocellum*);

(e) a nucleotide sequence encoding a polypeptide with xylose isomerase activity, which polypeptide comprises an amino acid sequence that has at least 67.3, 68, 69, 70, 71, 72, 73, 74, 75, 76, 77, 78, 79, 80, 81, 82, 83, 84, 85, 86, 87, 88, 89, 90, 91, 92, 93, 94, 95, 95, 96, 97, 98, or 99% sequence identity with the amino acid sequence of SEQ ID NO. 5 (*Epulopiscium* sp. 'N.t. morphotype B);

(f) a nucleotide sequence encoding a polypeptide with xylose isomerase activity, which polypeptide comprises an amino acid sequence that has at least 96.2, 96.5, 97, 98, or 99% sequence identity with the amino acid sequence of SEQ ID NO. 1 (*Lachnoclostridium phytofermentans*);

(g) a nucleotide sequence encoding a polypeptide with xylose isomerase activity, which polypeptide comprises an amino acid sequence that has at least 65.6, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 95, 96, 97, 98, or 99% sequence identity with the amino acid sequence of SEQ ID NO. 6 (*Alkaliphilus metalliredigens*);

(h) a nucleotide sequence encoding a polypeptide with xylose isomerase activity, which polypeptide comprises an amino acid sequence that has at least 69.4, 70, 71, 72, 73, 74, 75, 76, 77, 78, 79, 80, 81, 82, 83, 84, 85, 86, 87, 88, 89, 90, 91, 92, 93, 94, 95, 95, 96, 97, 98, or 99% sequence identity with the amino acid sequence of SEQ ID NO. 3 (*Mageeibacillus indolicus*);

(i) a nucleotide sequence encoding a polypeptide with xylose isomerase activity, which polypeptide comprises an amino acid sequence that has at least 72.7, 73, 74, 75, 76, 77, 78, 79, 80, 81, 82, 83, 84, 85, 86, 87, 88, 89, 90, 91, 92, 93, 94, 95, 95, 96, 97, 98, or 99% sequence identity with the amino acid sequence of SEQ ID NO. 2 (*Clostridium algidicarnis*);

(j) a nucleotide sequence encoding a polypeptide with xylose isomerase activity, which polypeptide comprises an amino acid sequence that has at least 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 95, 96, 97, 98, or 99% sequence identity with the amino acid sequence of SEQ ID NO. 12 (*Peptoclostridium difficile*);

(k) a nucleotide sequence the complementary strand of which hybridises to a nucleotide sequence of one of (a)-(j); and, (l) a nucleotide sequence the sequence of which differs from the sequence of a nucleotide sequence of (k) due to the degeneracy of the genetic code.

The nucleotide sequences of the invention encode a novel class of xylose isomerases that may be functionally expressed in eukaryotic microbial host cells of the invention as defined below. The nucleotide sequences of the invention preferably encode xylose isomerases that naturally occurs in the source organism, e.g. the source bacterium.

A preferred nucleotide sequence of the invention thus encodes a xylose isomerase with an amino acid sequence that is identical to that of a xylose isomerase that is obtainable from (or naturally occurs in) a bacterium of the Family Clostridiaceae, more preferably a bacterium of the genus *Clostridium*, e.g. *Clostridium algidicarnis*, but more preferred is *Clostridium saccharoperbutylacetonicum* and most preferred is [*Clostridium*] *cellulosi*.

Another preferred nucleotide sequence of the invention encodes a xylose isomerase with an amino acid sequence that is identical to that of a xylose isomerase that is obtainable from (or naturally occurs in) a bacterium of the Family Eubacteriaceae, more preferably a bacterium of the genus *Eubacterium*, of which the species *Eubacterium* sp. CAG_180 is most preferred.

Alternatively, nucleotide sequence of the invention encodes a xylose isomerase with an amino acid sequence that is identical to that of a xylose isomerase that is obtainable from (or naturally occurs in) a bacterium of a genus selected from the group consisting of *Cellulosilyticum, Epulopiscium, Lachnoclostridium, Alkaliphilus, Mageeibacillus* and *Peptoclostridium*, more preferably a bacterium of a species selected from the group consisting of *Cellulosilyticum lentocellum, Epulopiscium* sp. 'N.t. morphotype B, *Lachnoclostridium phytofermentans, Alkaliphilus metalliredigens, Mageeibacillus indolicus* and *Peptoclostridium difficile*.

It is however understood that nucleotide sequences encoding engineered forms of any of the xylose isomerases defined above and that comprise one or more amino acid substitutions, insertions and/or deletions as compared to the corresponding naturally occurring xylose isomerases but that are within the ranges of identity or similarity as defined herein are expressly included in the invention. Therefore, in one embodiment the nucleotide sequence of the invention encodes a xylose isomerase amino acid sequence comprising a xylose isomerase signature sequence as defined by Meaden et al. (1994, Gene, 141: 97-101): VXW[GP]GREG[YSTA] (present at positions 187-195) and [LIVM]EPKPX[EQ]P (present at positions 232-239), wherein "X" can be any amino acid and wherein amino acids in brackets indicates that one of the bracketed amino acids can be present at that position in the signature sequence. A xylose isomerase amino acid sequence of the invention further preferably comprises the conserved amino acid residues His-102, Asp-105, and Asp-340, which constitute a triad directly involved in catalysis, Lys-235 plays a structural as well as a functional catalytic role, and Glu-233, which is involved in binding of the magnesium (Vangrysperre et al., 1990, Biochem. J. 265: 699-705; Henrick et al., J. Mol. Biol. 208: 129-157; Bhosale et al., 1996 Microbiol. Rev. 60: 280-300). Amino acid positions of the above signature sequences and conserved residues refer to positions in the reference amino acid sequence of the Piromycesxylose isomerase of SEQ ID NO: 18. In amino acid sequences of the invention other than SEQ ID NO: 18, preferably, the amino acid positions of the above signature sequences and conserved residues are present in amino acid positions corresponding to the positions of the signature sequences and conserved residues in SEQ ID NO: 18, preferably in a ClustalW (1.83 or 1.81) sequence alignment using default settings. The skilled person will know how to identify corresponding amino acid positions in xylose isomerase amino acid sequences other than SEQ ID NO: 18 using amino acid sequence alignment algorithms as defined hereinabove. An example of such an alignment is depicted in Table 2.

In one embodiment therefore, the nucleotide sequence can encode engineered forms of any of the xylose isomerases defined above and that comprise one or more amino acid substitutions, insertions and/or deletions as compared to the corresponding naturally occurring xylose isomerase but that are within the ranges of identity or similarity as defined herein. The nucleotide sequence of the invention encodes a xylose isomerase, the amino acid sequence of which at least comprises in each of the invariable positions (that are indicated in Table 2 with a "*"), the amino acid present in a invariable position. Preferably, the amino acid sequence also comprises in the strongly conserved positions (that are indicated in Table 2 with a ":") one of the amino acids present in a strongly conserved position. More preferably, the amino acid sequence further also comprises in the less strongly conserved positions (that are indicated in Table 2 with a ".") one of the amino acids present in a less strongly conserved position. Amino acid substitutions outside of these invariable and conserved positions are less unlikely to affect xylose isomerase activity. In addition, to date a vast amount of amino acid sequences of xylose isomerases are known in the art and new ones are added continuously being added. Sequence alignments of SEQ ID NO: 18 and the xylose isomerase sequences of the invention with these known and new xylose isomerase amino acid sequences will indicate further conserved regions and amino acid positions, the conservation of which are important for structure and enzymatic activity.

The nucleotide sequence encodes a xylose isomerase that is preferably expressed in active form in the host cell. Thus, expression of the nucleotide sequence in the host cell produces a xylose isomerase with a specific activity of at least 10 U xylose isomerase activity per mg protein at 25° C., preferably at least 20, 25, 30, 50, 100, 200 or 300 U per mg at 25° C. The specific activity of the xylose isomerase expressed in the host cell is herein defined as the amount of xylose isomerase activity units per mg protein of cell free lysate of the host cell, e.g. a yeast cell free lysate. Determination of the xylose isomerase activity, amount of protein and preparation of the cell free lysate are as described in the Examples. Preferably, expression of the nucleotide sequence in the host cell produces a xylose isomerase with a $K_m$ for xylose that is less than 50, 40, 30 or 25 mM, more preferably, the $K_m$ for xylose is about 20 mM or less.

The nucleotide sequence encodes a xylose isomerase that preferably has reduced sensitivity to inhibition by xylitol. Preferably, the xylose isomerase shows less inhibition by xylitol than the *Piromyces* isomerase (SEQ ID NO: 18), more preferably the xylose isomerase shows less inhibition by xylitol than the *C. phytofermentans* isomerase (SEQ ID NO: 17). The nucleotide sequence thus preferably encodes a xylose isomerase that has an apparent inhibition constant K; that is greater than 4.6, 5, 10, 14.51, 15 mM xylitol. Sensitivity to inhibition by xylitol and apparent inhibition constant K; for xylitol can be determined as described in (11).

The nucleotide sequences of the invention, encoding polypeptides with xylose isomerase activity, are obtainable from genomic and/or cDNA of a bacterium that belongs to a phylum, class, order, family or genus as described above, using method for isolation of nucleotide sequences that are well known in the art per se (see e.g. Sambrook and Russell (2001) "Molecular Cloning: A Laboratory Manual ($3^{rd}$ edition), Cold Spring Harbor Laboratory, Cold Spring Harbor Laboratory Press, New York). The nucleotide sequences of the invention are e.g. obtainable in a process wherein a) degenerate PCR primers (such as those in SEQ ID NO.'s 19 and 20) are used on genomic and/or cDNA of a suitable organism (e.g. a bacterium as indicated above) to generate a PCR fragment comprising part of the nucleotide sequences encoding the polypeptides with xylose isomerase activity; b) the PCR fragment obtained in a) is used as probe to screen a cDNA and/or genomic library of the organism; and c) producing a cDNA or genomic DNA comprising the nucleotide sequence encoding a polypeptide with xylose isomerase activity.

To increase the likelihood that the xylose isomerase is expressed at sufficient levels and in active form in the host cells of the invention, the nucleotide sequence encoding these enzymes, as well as other enzymes of the invention (see below), are preferably adapted to optimise their codon usage to that of the host cell in question. The adaptiveness of a nucleotide sequence encoding an enzyme to the codon usage of a host cell may be expressed as codon adaptation index (CAI). The codon adaptation index is herein defined as a measurement of the relative adaptiveness of the codon usage of a gene towards the codon usage of highly expressed genes in a particular host cell or organism. The relative adaptiveness (w) of each codon is the ratio of the usage of each codon, to that of the most abundant codon for the same amino acid. The CAI index is defined as the geometric mean of these relative adaptiveness values. Non-synonymous codons and termination codons (dependent on genetic code) are excluded. CAI values range from 0 to 1, with higher values indicating a higher proportion of the most abundant codons (see Sharp and Li, 1987, Nucleic Acids Research 15: 1281-1295; also see: Jansen et al., 2003, Nucleic Acids Res. 31(8):2242-51). An adapted nucleotide sequence preferably has a CAI of at least 0.2, 0.3, 0.4, 0.5, 0.6, 0.7, 0.8 or 0.9. Most preferred are the sequences which have been codon optimised for expression in *S. cerevisiae* cells, as listed in SEQ ID NO's: 21-34, of which SEQ ID NO's: 27, 28 and 30 are preferred, and SEQ ID NO: 28 is most preferred.

The host cell to be transformed with a nucleic acid construct comprising a nucleotide sequence encoding a xylose isomerase of the invention preferably is a eukaryotic microbial host, more preferably a fungal host cell, such as a yeast or filamentous fungal host cell. Preferably the host cell is a cultured cell. The host cell of the invention, preferably is a host capable of active or passive pentose (xylose and preferably also arabinose) transport into the cell. The host cell preferably contains active glycolysis. The host cell may further preferably contains an endogenous pentose phosphate pathway and may contain endogenous xylulose kinase activity so that xylulose isomerised from xylose may be metabolised to pyruvate. The host further preferably contains enzymes for conversion of a pentose (preferably through pyruvate) to a desired fermentation product such as ethanol, lactic acid, 3-hydroxy-propionic acid, acrylic acid, acetic acid, succinic acid, citric acid, amino acids, 1,3-propane-diol, ethylene, glycerol, 1-lactam antibiotics and cephalosporins. A particularly preferred host cell is a host cell that is naturally capable of alcoholic fermentation, preferably, anaerobic alcoholic fermentation. The host cell further preferably has a high tolerance to ethanol, a high tolerance to low pH (i.e. capable of growth at a pH lower than 5, 4, or 3) and towards organic acids like lactic acid, acetic acid or formic acid and sugar degradation products such as furfural and hydroxy-methylfurfural, and a high tolerance to elevated temperatures. Any of these characteristics or activities of the host cell may be naturally present in the host cell or may be introduced or modified by genetic modification, preferably by self-cloning or by the methods of the invention described below. A suitable cell is a cultured cell, a cell that may be cultured in fermentation process e.g. in submerged or solid state fermentation. Particularly suitable cells are eukaryotic microorganism like e.g. fungi, however, most suitable for use in the present inventions are yeasts or filamentous fungi.

Yeasts are herein defined as eukaryotic microorganisms and include all species of the subdivision Eumycotina (Yeasts: characteristics and identification, J. A. Barnett, R. W. Payne, D. Yarrow, 2000, 3rd ed., Cambridge University Press, Cambridge UK; and, The yeasts, a taxonomic study, C. P. Kurtzman and J. W. Fell (eds) 1998, 4$^{th}$ ed., Elsevier Science Publ. B.V., Amsterdam, The Netherlands) that predominantly grow in unicellular form. Yeasts may either grow by budding of a unicellular thallus or may grow by fission of the organism. Preferred yeasts as host cells belong to the genera *Saccharomyces*, *Kluyveromyces*, *Candida*, *Pichia*, *Schizosaccharomyces*, *Hansenula*, *Kloeckera*, *Schwanniomyces*, *Yarrowia*, *Kazachstania* and *Naumovia*. Preferred yeast species as host cells include *S. cerevisiae*, *S. exiguus*, *S. bayanus*, *K. lactis*, *K. marxianus* and *Schizosaccharomyces pombe*.

Preferably the yeast cell of the invention is a yeast cell that is naturally capable of anoxic fermentation, more preferably alcoholic fermentation and most preferably anoxic alcoholic fermentation. Over the years suggestions have been made for the introduction of various organisms for the production of bio-ethanol from crop sugars. In practice, however, all major bio-ethanol production processes have continued to use the yeasts of the genus *Saccharomyces* as ethanol producer. This is due to the many attractive features of *Saccharomyces* species for industrial processes, i.e., a high acid-, ethanol- and osmo-tolerance, capability of anaerobic growth, and of course its high alcoholic fermentative capacity. Most preferably therefore a yeast host cell of the invention belongs to a species selected from the group consisting of *Saccharomyces cerevisiae*, *S. bayanus*, *S. bulderi*, *S. cervazzii*, *S. cariocanus*, *S. castellii*, *S. dairenensis*, *S. exiguus*, *S. kluyveri*, *S. kudriazevii*, *S. mikatae*, *S. paradoxus*, *S. pastorianus*, *S. turicensis* and *S. unisporus* (Kurtzman, 2003, supra; and J. A. Barnett, R. W. Payne, D. Yarrow, 2000, supra). Preferably the yeast cell of the invention is an industrial yeast strain or a yeast strain derived from industrial yeast strain. Industrial yeast strains are often diploid, polypoloid or aneuploid and have proven capabilities for application in large scale industrial fermentation. Suitable industrial yeast strains include e.g. the commercial strains Gert Strand Turbo yeasts, Alltech SuperStart™, Fermiol Super HA™, Thermosacc™ and Ethanol Red™. Also suitable are yeast cells derived from any of these strain by modifications as described herein.

Filamentous fungi are herein defined as eukaryotic microorganisms that include all filamentous forms of the subdivision Eumycotina. These fungi are characterized by a vegetative mycelium composed of chitin, cellulose, and other complex polysaccharides. The filamentous fungi of the present invention are morphologically, physiologically, and genetically distinct from yeasts. Vegetative growth by filamentous fungi is by hyphal elongation and carbon catabolism of most filamentous fungi is obligately aerobic. Preferred filamentous fungi as host cells belong to the genera *Aspergillus*, *Trichoderma*, *Humicola*, *Acremonium*, *Fusarium*, and *Penicillium*.

In a host cell of the invention, the nucleotide sequence encoding the xylose isomerase as defined above is preferably operably linked to a promoter that causes sufficient expression of the nucleotide sequences in the cell to confer to the cell the ability to convert xylose into xylulose. More preferably the promoter causes sufficient expression of the nucleotide sequences to confer to the cell the ability to grow on xylose as sole carbon and/or energy source, most preferably under anaerobic conditions. Suitable promoters for expression of the nucleotide sequence as defined above include promoters that are insensitive to catabolite (glucose) repression and/or that do not require xylose for induction. Promoters having these characteristics are widely available and known to the skilled person. Suitable examples of such promoters include e.g. promoters from glycolytic genes such as the phosphofructokinase (PPK), triose phosphate isomerase (TPI), glyceraldehyde-3-phosphate dehydrogenase (GPD, TDH3 or GAPDH), pyruvate kinase (PYK), phosphoglycerate kinase (PGK), glucose-6-phosphate isomerase promoter (PG/1) promoters from yeasts or filamentous fungi; more details about such promoters from yeast may be found in (WO 93/03159). Other useful promoters are ribosomal protein encoding gene promoters, the lactase gene promoter (LAC4), alcohol dehydrogenase promoters (ADH1, ADH4, and the like), the enolase promoter (ENO), the hexose(glucose) transporter promoter (HXT7), and the cytochrome cl promoter (CYC1). Other promoters, both constitutive and inducible, and enhancers or upstream activating sequences will be known to those of skill in the art. Preferably the promoter that is operably linked to nucleotide sequence as defined above is homologous to the host cell.

In a host cell of the invention, the nucleotide sequence encoding the xylose isomerase as defined above is preferably expressed from an expression construct wherein the coding sequence is operably linked to a promoter as defined above. An expression construct in a host cell of the invention may be present on a plasmid, preferable a multicopy plasmid. However, more preferably the expression construct is integrated into the genome of the host cell. Preferably, the host cell comprises multiple copies of the expression construct integrated into its genome. More preferably, the multiple copies (e.g. 2, 3, 4, 5, 6, 8, 10 ore more copies) of the expression construct are integrated into in more than one, e.g. at least two, different genomic or chromosomal locations in the host cell's genome. A preferred chromosomal location for integration of an expression construct into the genome of a host cell of the invention is an intergenic region, e.g. the intergenic region downstream of TYE7 and upstream of the tRNA gene tP(UGG)O3 in chromosome XV. In one embodiment, the host cell is a diploid, polypoloid or aneuploid host cell. Preferably in the diploid, polypoloid or aneuploid host cell, the expression construct is present at a chromosomal location that is present in at least two copies in the cell's genome. Optionally more than one tandem copies, e.g. two copies, of the expression construct is integrated in a genomic or chromosomal location.

In one embodiment a host cell of the invention comprises more than one different type of nucleotide sequence encoding e.g. at least two different xylose isomerases as defined above, or e.g. encoding a xylose isomerases as defined above in combination with any other xylose isomerase, e.g. a xylose isomerase already known in the art.

The host cell of the invention further preferably comprises xylulose kinase activity so that xylulose isomerised from xylose may be metabolised to pyruvate. Preferably, the cell contains endogenous xylulose kinase activity. More preferably, a cell of the invention comprises a genetic modification that increases the specific xylulose kinase activity. Preferably the genetic modification causes overexpression of a xylulose kinase, e.g. by overexpression of a nucleotide sequence encoding a xylulose kinase. The gene encoding the xylulose kinase may be endogenous to the cell or may be a xylulose kinase that is heterologous to the cell. A nucleotide sequence that may be used for overexpression of xylulose kinase in the cells of the invention is e.g. the xylulose kinase gene from S. cerevisiae (XKS1) as described by Deng and Ho (1990, Appl. Biochem. Biotechnol. 24-25: 193-199). Another preferred xylulose kinase is a xylose kinase that is related to the xylulose kinase from *Piromyces* (xylB; see WO 03/062430). This *Piromyces* xylulose kinase is actually more related to prokaryotic kinase than to all of the known eukaryotic kinases such as the yeast kinase. The eukaryotic xylulose kinases have been indicated as non-specific sugar kinases, which have a broad substrate range that includes xylulose. In contrast, the prokaryotic xylulose kinases, to which the *Piromyces* kinase is most closely related, have been indicated to be more specific kinases for xylulose, i.e. having a narrower substrate range. In the cells of the invention, a xylulose kinase to be overexpressed is overexpressed by at least a factor 1.1, 1.2, 1.5, 2, 5, 10 or 20 as compared to a strain which is genetically identical except for the genetic modification causing the overexpression. It is to be understood that these levels of overexpression may apply to the steady state level of the enzyme's activity, the steady state level of the enzyme's protein as well as to the steady state level of the transcript coding for the enzyme.

A cell of the invention further preferably comprises a genetic modification that increases the flux of the pentose phosphate pathway as described in WO 06/009434. In particular, the genetic modification causes an increased flux of the non-oxidative part pentose phosphate pathway. A genetic modification that causes an increased flux of the non-oxidative part of the pentose phosphate pathway is herein understood to mean a modification that increases the flux by at least a factor 1.1, 1.2, 1.5, 2, 5, 10 or 20 as compared to the flux in a strain which is genetically identical except for the genetic modification causing the increased flux. The flux of the non-oxidative part of the pentose phosphate pathway may be measured as described in WO 06/009434.

Genetic modifications that increase the flux of the pentose phosphate pathway may be introduced in the cells of the invention in various ways. These including e.g. achieving higher steady state activity levels of xylulose kinase and/or one or more of the enzymes of the non-oxidative part pentose phosphate pathway and/or a reduced steady state level of unspecific aldose reductase activity. These changes in steady state activity levels may be effected by selection of mutants (spontaneous or induced by chemicals or radiation) and/or by recombinant DNA technology e.g. by overexpression or inactivation, respectively, of genes encoding the enzymes or factors regulating these genes.

In a preferred cell of the invention, the genetic modification comprises overexpression of at least one enzyme of the (non-oxidative part) pentose phosphate pathway. Preferably the enzyme is selected from the group consisting of the enzymes encoding for ribulose-5-phosphate isomerase, ribulose-5-phosphate 3-epimerase, transketolase and transaldolase. Various combinations of enzymes of the (non-oxidative part) pentose phosphate pathway may be overexpressed. In one embodiment of the invention each of the enzymes ribulose-5-phosphate isomerase, ribulose-5-phosphate 3-epimerase, transketolase and transaldolase is overexpressed in the cell of the invention.

There are various means available in the art for overexpression of enzymes in the cells of the invention. In particular, an enzyme may be overexpressed by increasing the copynumber of the gene coding for the enzyme in the cell, e.g. by integrating additional copies of the gene in the cell's genome, by expressing the gene from an episomal multicopy expression vector or by introducing a episomal expression vector that comprises multiple copies of the gene. The coding sequence used for overexpression of the enzymes preferably is homologous to the host cell of the invention. However, coding sequences that are heterologous to the host cell of the invention may likewise be applied.

Alternatively overexpression of enzymes in the cells of the invention may be achieved by using a promoter that is not native to the sequence coding for the enzyme to be overexpressed, i.e. a promoter that is heterologous to the coding sequence to which it is operably linked. Although the promoter preferably is heterologous to the coding sequence to which it is operably linked, it is also preferred that the promoter is homologous, i.e. endogenous to the cell of the invention. Preferably the heterologous promoter is capable of producing a higher steady state level of the transcript comprising the coding sequence (or is capable of producing more transcript molecules, i.e. mRNA molecules, per unit of time) than is the promoter that is native to the coding sequence, preferably under conditions where xylose or xylose and glucose are available as carbon sources, more preferably as major carbon sources (i.e. more than 50% of the available carbon source consists of xylose or xylose and glucose), most preferably as sole carbon sources. Suitable promoters in this context include promoters as described above for expression of the nucleotide sequences encoding xylose isomerases as defined above.

A further preferred cell of the invention comprises a genetic modification that reduces unspecific aldose reductase activity in the cell. Preferably, unspecific aldose reductase activity is reduced in the host cell by one or more genetic modifications that reduce the expression of or inactivates a gene encoding an unspecific aldose reductase. Preferably, the genetic modifications reduce or inactivate the expression of each endogenous copy of a gene encoding an unspecific aldose reductase that is capable of reducing an aldopentose, including, xylose, xylulose and arabinose, in the cell's genome. A given cell may comprise multiple copies of genes encoding unspecific aldose reductases as a result of di-, poly- or aneu-ploidy, and/or a cell may contain several different (iso)enzymes with aldose reductase activity that differ in amino acid sequence and that are each encoded by a different gene. Also in such instances preferably the expression of each gene that encodes an unspecific aldose reductase is reduced or inactivated. Preferably, the gene is inactivated by deletion of at least part of the gene or by disruption of the gene, whereby in this context the term gene also includes any non-coding sequence up- or down-stream of the coding sequence, the (partial) deletion or inactivation of which results in a reduction of expression of unspecific aldose reductase activity in the host cell. A nucleotide sequence encoding an aldose reductase whose activity is to be reduced in the cell of the invention and amino acid sequences of such aldose reductases are described in WO 06/009434 and include e.g. the (unspecific) aldose reductase genes of *S. cerevisiae* GRE3 gene (Traff et al., 2001, Appl. Environm. Microbiol. 67: 5668-5674) and orthologues thereof in other species.

A host cell of the invention further preferably comprises at least one genetic modification that results in a characteristic selected from the group consisting of: a) increased tolerance to ethanol; b) increased tolerance to acetic acid; c) reduced production of glycerol; d) increased xylose to ethanol fermentation rate; and e) increased thermotolerance.

The genetic modification that results in increased tolerance to ethanol preferably is a modification as e.g. described in WO 2012/175552 and WO 2014/170330, such as e.g. a modification that introduces alleles of one or more of the ADE1, KIN3, MKT1 and VPS70 that confer increased tolerance to ethanol, and/or a modification that overexpresses a wild type SWS2 gene and/or that inactivates the APJ1 gene, which also confers increased tolerance to ethanol.

The genetic modification that results in increased tolerance to acetic acid preferably is a modification as e.g. described in WO 2015/181169 and WO 2016/083397, such as e.g. a modification that introduces an allele of one or more of the GLO1, DOT5, CUP2 and HAA1 genes that confers increased tolerance to acetic acid.

The genetic modification that results in reduced production of glycerol, preferably is a modification as e.g. described in WO 2014/048863, such as e.g. a modification that introduces a mutant SSK1 gene encoding a truncated ssk1 protein.

The genetic modification that results in increased xylose to ethanol fermentation rate preferably is a modification as e.g. described in WO 2015/086805, such as e.g. a modification that introduces an allele of the NNK1 gene that confers an increased xylose to ethanol fermentation rate.

The genetic modification that results in increased thermotolerance preferably is a modification as e.g. described in WO 2014/090930, such as e.g. a modification that introduces overexpression of at least one of a gene encoding the Prp42 protein and a gene encoding the Smd2 protein.

A preferred host cell of the invention is a host cell that is improved in at least one industrially relevant phenotype by evolutionary engineering. Evolutionary engineering is a process wherein industrially relevant phenotypes of a microorganism, herein the yeast, can be coupled to the specific growth rate and/or the affinity for a nutrient, by a process of rationally set-up natural selection. Evolutionary Engineering is e.g. described in detail in Cakar et al. (2011, FEMS Yeast Research 12:171-182). Preferably, the D-xylose utilization rate of the host cell is improved by evolutionary engineering. Improvement of the D-xylose utilization rate of yeast host cells by evolutionary engineering is described in detail by Demeke et al. (12, 15 and 16).

In a preferred host cell according to the invention, the nucleic acid construct confers to the host cell the ability to grow on xylose as carbon/energy source, preferably as sole carbon/energy source, and preferably under anaerobic conditions, i.e. conditions as defined herein below for anaerobic fermentation process. Preferably, when grown on xylose as carbon/energy source the transformed host produces essentially no xylitol, e.g. the xylitol produced is below the detection limit or e.g. less than 5, 2, 1, 0.5, or 0.3% of the carbon consumed on a molar basis.

A host cell of the invention preferably has the ability to grow on xylose as sole carbon/energy source at a rate of at least 0.01, 0.02, 0.05, 0.1, 0.2, 0.25 or 0.3 $h^{-1}$ under aerobic conditions, or, more preferably, at a rate of at least 0.005, 0.01, 0.02, 0.05, 0.08, 0.1, 0.12, 0.15 or 0.2 $h^{-1}$ under anaerobic conditions. A cell of the invention preferably has the ability to grow on a mixture of glucose and xylose (in a 1:1 weight ratio) as sole carbon/energy source at a rate of at least 0.01, 0.02, 0.05, 0.1, 0.2, 0.25 or 0.3 $h^{-1}$ under aerobic conditions, or, more preferably, at a rate of at least 0.005, 0.01, 0.02, 0.05, 0.08, 0.1, 0.12, 0.15 or 0.2 $h^{-1}$ under anaerobic conditions. Thus, in a preferred host cell according to the invention, the nucleic acid construct confers to the host cell the ability to anaerobically ferment xylose as sole carbon source in a process wherein ultimately pyruvate is used as an electron (and hydrogen acceptor) and is reduced to fermentation products such as ethanol, lactic acid, 3-hydroxy-propionic acid, acrylic acid, acetic acid, succinic acid, citric acid, amino acids, 1,3-propane-diol, ethylene, glycerol, butyric acid, caproate, butanol, glyoxylate, muconic acid, fatty alcohols, fatty acids, 1-lactam antibiotics and cephalosporins.

Preferably, a cell of the invention has a specific xylose consumption rate of at least 200, 300, 400, 600, 700, 800, 900 or 1000 mg h-1 (g dry weight)-1. Preferably, a cell of the invention has a yield of fermentation product (such as ethanol) on xylose that is at least 20, 40, 50, 60, 80, 90, 95 or 98% of the cell's yield of fermentation product (such as ethanol) on glucose. More preferably, the modified host cell's yield of fermentation product (such as ethanol) on xylose is equal to the host cell's yield of fermentation product (such as ethanol) on glucose. Likewise, the modified host cell's biomass yield on xylose is preferably at least 55, 60, 70, 80, 85, 90, 95 or 98% of the host cell's biomass yield on glucose. More preferably, the modified host cell's biomass yield on xylose is equal to the host cell's biomass yield on glucose. It is understood that in the comparison of yields on glucose and xylose both yields are compared under aerobic conditions or both under anaerobic conditions.

In another aspect the invention relates to a process for producing a fermentation product selected from the group consisting of ethanol, lactic acid, 3-hydroxy-propionic acid, acrylic acid, acetic acid, succinic acid, citric acid, amino acids, 1,3-propane-diol, ethylene, glycerol, butyric acid, caproate, butanol, glyoxylate, muconic acid, fatty alcohols, fatty acids, 1-lactam antibiotics and cephalosporins. The process preferably comprises the steps of: a) fermenting a medium containing a source of xylose with a cell as defined hereinabove, whereby the cell ferments xylose to the fermentation product, and optionally, b) recovery of the fermentation product.

In addition to a source of xylose the carbon source in the fermentation medium may also comprise a source of glucose. The skilled person will further appreciate that the fermentation medium may further also comprise other types of carbohydrates such as e.g. in particular a source of arabinose. The sources of xylose and glucose may be xylose and glucose as such (i.e. as monomeric sugars) or they may be in the form of any carbohydrate oligo- or polymer comprising xylose and/or glucose units, such as e.g. lignocellulose, xylans, cellulose, starch and the like. For release of xylose and/or glucose units from such carbohydrates, appropriate carbohydrases (such as xylanases, glucanases, amylases, cellulases, glucanases and the like) may be added to the fermentation medium or may be produced by the modified host cell. In the latter case the modified host cell may be genetically engineered to produce and excrete such carbohydrases. An additional advantage of using oligo- or polymeric sources of glucose is that it enables to maintain a low(er) concentration of free glucose during the fermentation, e.g. by using rate-limiting amounts of the carbohydrases preferably during the fermentation. This, in turn, will prevent repression of systems required for metabolism and transport of non-glucose sugars such as xylose. In a preferred process the modified host cell ferments both the xylose and glucose, preferably simultaneously in which case preferably a modified host cell is used which is insensitive to glucose repression to prevent diauxic growth. In addition to a source of xylose (and glucose) as carbon source, the fermentation medium will further comprise the appropriate ingredient required for growth of the modified host cell. Compositions of fermentation media for growth of eukaryotic microorganisms such as yeasts and filamentous fungi are well known in the art.

The fermentation process may be an aerobic or an anaerobic fermentation process. An anaerobic fermentation process is herein defined as a fermentation process run in the absence of oxygen or in which substantially no oxygen is consumed, preferably less than 5, 2.5 or 1 mmol/L/h, more preferably 0 mmol/L/h is consumed (i.e. oxygen consumption is not detectable), and wherein organic molecules serve as both electron donor and electron acceptors. In the absence of oxygen, NADH produced in glycolysis and biomass formation, cannot be oxidised by oxidative phosphorylation. To solve this problem many microorganisms use pyruvate or one of its derivatives as an electron and hydrogen acceptor thereby regenerating $NAD^+$. Thus, in a preferred anaerobic fermentation process pyruvate is used as an electron (and hydrogen acceptor) and is reduced to fermentation products such as ethanol, as well as non-ethanol fermentation products such as lactic acid, 3-hydroxy-propionic acid, acrylic acid, acetic acid, succinic acid, citric acid, amino acids, 1,3-propane-diol, ethylene, glycerol, butyric acid, caproate, butanol, glyoxylate, muconic acid, fatty alcohols, fatty acids, β-lactam antibiotics and cephalosporins. Anaerobic processes of the invention are preferred over aerobic processes because anaerobic processes do not require investments and energy for aeration and in addition, anaerobic processes produce higher product yields than aerobic processes. Alternatively, the fermentation process of the invention may be run under aerobic oxygen-limited conditions. Preferably, in an aerobic process under oxygen-limited conditions, the rate of oxygen consumption is at least 5.5, more preferably at least 6 and even more preferably at least 7 mmol/L/h.

The fermentation process is preferably run at a temperature that is optimal for the modified cells of the invention. Thus, for most yeasts or fungal cells, the fermentation process is performed at a temperature which is less than 42° C., preferably less than 38° C. For yeast or filamentous fungal cells, the fermentation process is preferably performed at a temperature which is lower than 35, 33, 30 or 28° C. and at a temperature which is higher than 20, 22, or 25° C. For some species, such as *Kluyveromyces marxianus*, and engineered *Saccharomyces cerevisiae* strains, the fermentation process may be run at considerably higher temperatures, i.e. at 42° C., 43° C., or preferably between 45 and 50° C., or in rare cases between 50 and 55° C.

Preferably in the fermentation processes of the invention, the cells stably maintain the nucleic acid constructs that confer to the cell the ability of isomerising xylose into xylulose, and optionally converting arabinose into D-xylulose 5-phosphate. Preferably in the process at least 10, 20, 50 or 75% of the cells retain the abilities of isomerising xylose into xylulose, and optionally converting arabinose into D-xylulose 5-phosphate after 50 generations of growth, preferably under industrial fermentation conditions.

A preferred fermentation process according to the invention is a process for the production of ethanol, whereby the process comprises the steps of: a) fermenting a medium containing a source of xylose with a cell as defined hereinabove, whereby the cell ferments xylose, and optionally, b) recovery of the ethanol. The fermentation medium may further be performed as described above. In the process the volumetric ethanol productivity is preferably at least 0.5, 1.0, 1.5, 2.0, 2.5, 3.0, 5.0 or 10.0 g ethanol per litre per hour. The ethanol yield on xylose and/or glucose in the process preferably is at least 50, 60, 70, 80, 90, 95 or 98%. The ethanol yield is herein defined as a percentage of the theoretical maximum yield, which, for xylose and glucose is 0.51 g. ethanol per g. xylose or glucose.

In this document and in its claims, the verb "to comprise" and its conjugations is used in its non-limiting sense to mean that items following the word are included, but items not specifically mentioned are not excluded. In addition, reference to an element by the indefinite article "a" or "an" does not exclude the possibility that more than one of the element is present, unless the context clearly requires that there be one and only one of the elements. The indefinite article "a" or "an" thus usually means "at least one".

All patent and literature references cited in the present specification are hereby incorporated by reference in their entirety.

The following examples are offered for illustrative purposes only, and are not intended to limit the scope of the present invention in any way.

SHORT DESCRIPTION OF DRAWINGS

FIG. 1. Xylose fermentation performance of the M315CpXIΔ/CpXIΔ strain expressing a plasmid containing one of the first 7 XylA genes. The code indicating the bacterial origin of XylA genes is explained in Table 1. The fermentation was performed in duplicate using two independent transformants at a starting cell density of 1 g DW/L in 50 mL YP medium containing 4% xylose at 35° C. The average value is shown in the graph. The $CO_2$ production was estimated by measuring the weight loss during the fermentation.

Figure 2:
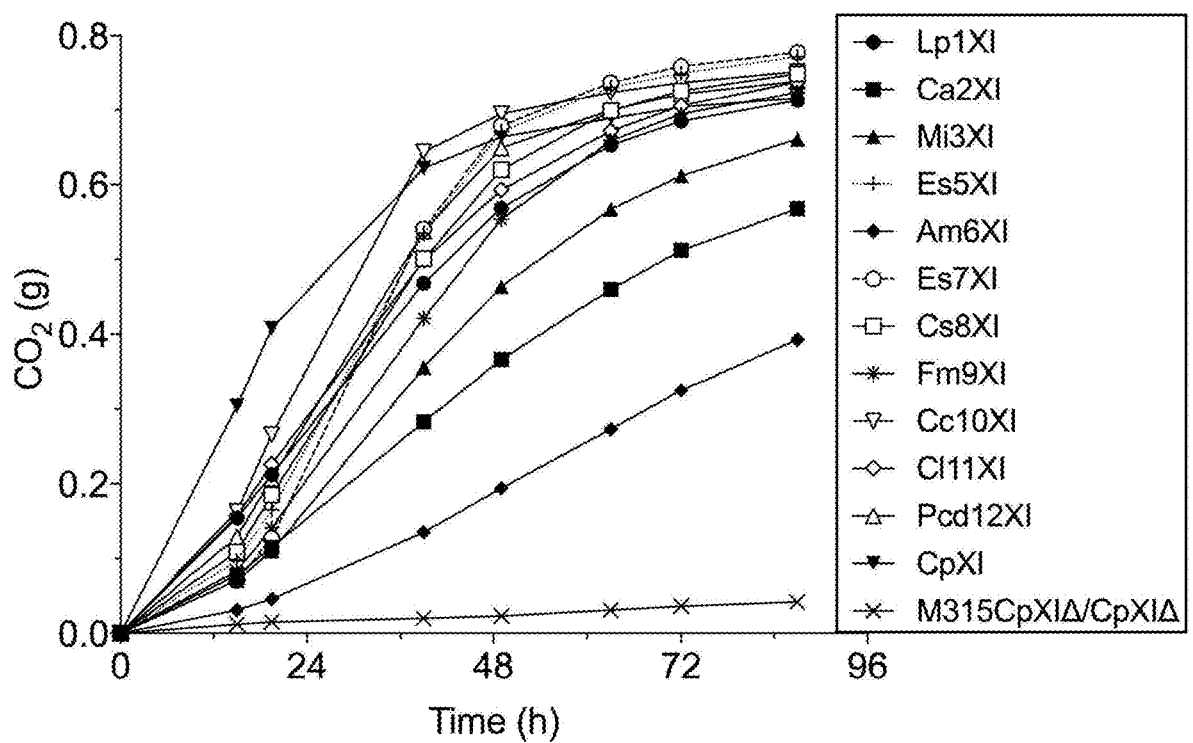

FIG. 2. Xylose fermentation performance of the M315CpXIΔ/CpXIΔ strain expressing a plasmid with one of the 11 XylA genes. The code indicating the bacterial origin of XylA genes is explained in Table 1. The fermentation was performed using 1 g DW/L initial cell density in 45 mL YP medium containing 4% xylose at 35° C. The $CO_2$ production was estimated by measuring the weight loss during fermentation.

Figure 3A:
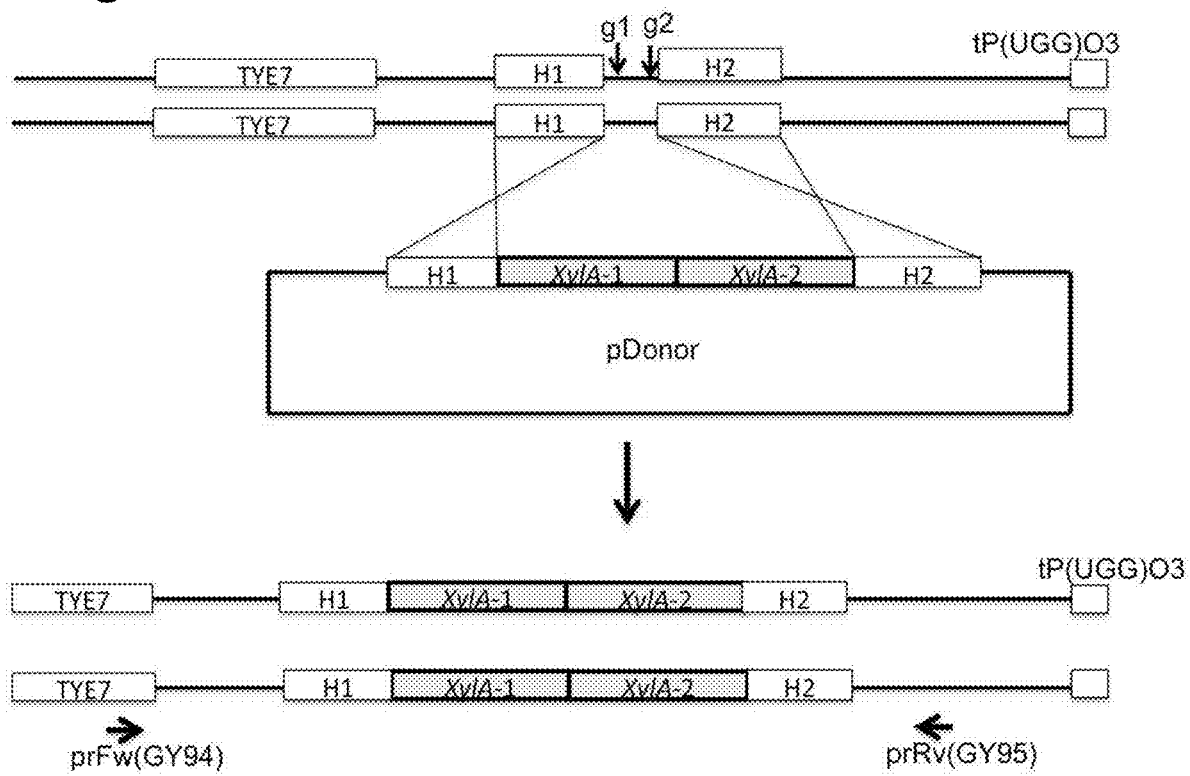
Figure 3B:
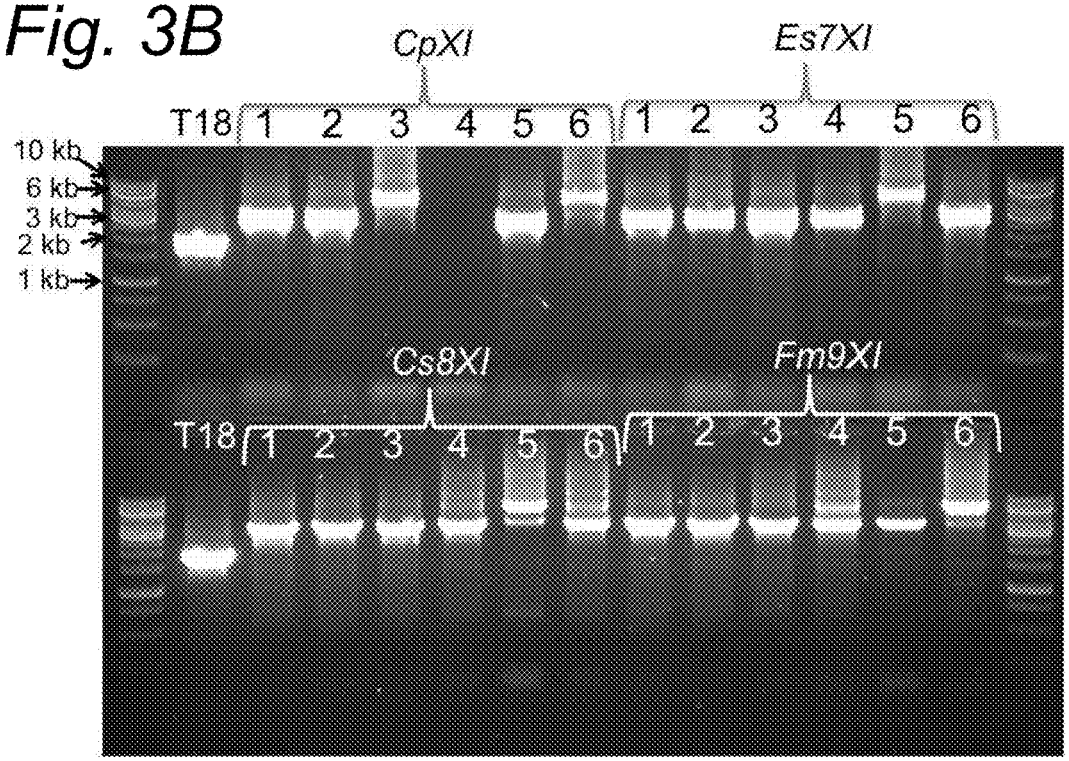

FIG. 3. Integration of XylA genes in the genome.

A) Method of integration using CRISPR/Cas9 methodology in chromosome XV between TYE7 and tp(UGG)O3. Arrows indicated by g1 and g2 are gRNA sites where Cas9 makes a double strand break in the chromosomes, guided by two gRNA cutting sites in a single guide RNA plasmid. A plasmid based donor DNA (pDonor) carried two XylA sequences XI1 and XI2 flanked by sequences H1 and H2 that are homologous to the site of integration to support homologous recombination.

B) Gel electrophoresis picture of the PCR performed for checking proper insertion of the XylA genes in the genome using two primers flanking the homologous sequences H1 and H2 [shown as prFw(GY94) and prRv(GY95)] at the bottom of panel A. Insertion of a single XylA copy in both alleles of the chromosome produced a PCR product of about 3 kb (e.g. Lane CpXI 1, 2 and 5), while insertion of two copies in both alleles resulted in a 5 kb PCR product (e.g. Lane CpXI 3 and 6). Absence of a XylA insertion is expected to produce a PCR band of about 1.6 Kb band, which is the size of the PCR band obtained for the control strain T18.

Figure 4:
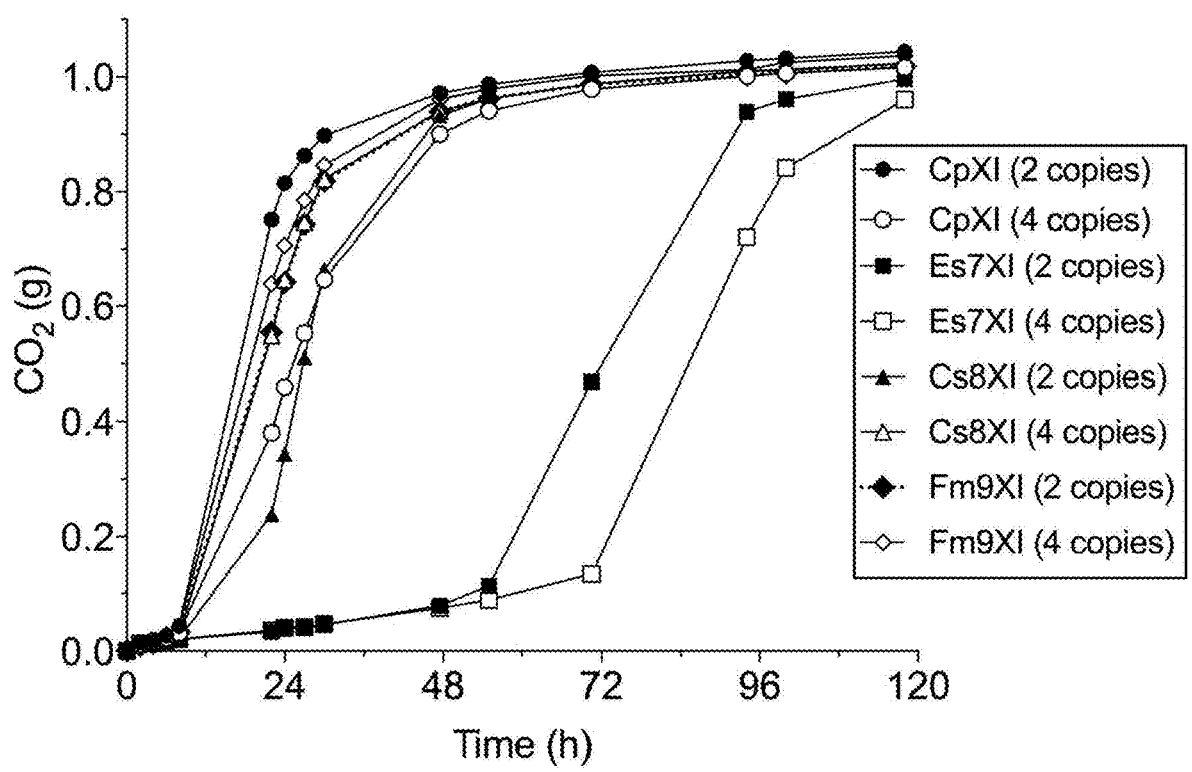

FIG. 4. Xylose fermentation performance of the GSE16-T18CpXIΔ/CpXIΔ based strains after genomic integration of different XylA genes. The code indicating the bacterial origin of XylA genes is explained in Table 1. For each XylA gene, two strains carrying either 2 copies or 4 copies were selected. The fermentation was performed using 1 g DW/L initial cell density in 50 mL YP medium containing 4% xylose at 35° C. $CO_2$ production was estimated by measuring the weight loss during fermentation.

FIG. 5. A) Xylose fermentation performance of the MDS130-based strains with genomic integration of different XylA genes as indicated. The code indicating the bacterial origin of XylA genes is explained in Table 1. B) Direct comparison of xylose fermentation performance of the MDS130 strain with the MDC5 strain.

EXAMPLES

Example 1

Introduction

In spite of the vast sequence information on xylose isomerases in public sequence databases, only few have been functionally expressed in yeast. One bottleneck might be due to differences in protein synthesis regulation mechanisms between prokaryotes and eukaryotes. The synthesis of bacterial proteins in yeast might not be properly regulated, which could be the reason for the frequent occurrence of inactive or insoluble proteins. Studies showed that proper expression of a gene does not necessarily correlate with proper enzymatic activity (13). In most XylA expressing strains, high enzymatic activity of XI and proper xylose fermentation capacity was observed only after further evolutionary adaptation of the host yeast strain, indicating that there are other regulatory mechanisms required for the proper functioning of the XI enzymes and for their proper connection with the other enzymes of the yeast fermentation pathway (11,12). Although the regulatory mechanisms are not well understood, certain genetic changes are required by the recombinant host for proper XI activity. This lack of a proper yeast strain as a host for functional expression in turn hinders the screening of potential XIs that might be active in an appropriate host but not in a regular yeast strain.

To overcome the bottleneck of lacking a proper host strain for screening of active bacterial XI genes, we have developed two yeast strains that are able to directly grow and efficiently ferment xylose upon expression of a bacterial XI. These strains have the same industrial yeast strain background of the strain that successfully expressed the Clostridium phytofermentans XylA gene (CpXI) (12,15,16). The first strain M315_CpXIΔ/CpXIΔ has been developed by deletion of the two copies of CpXI from the genome of strain M315. This parent strain M315 has been developed by random mutagenesis of a recombinant industrial strain Ethanol Red, which carried two copies of CpXI and xylulokinase (XKS1) and all the genes of the pentose phosphate pathway (PPP) overexpressed in the chromosome. The second platform strain GSE16-T18CpXIΔ/CpXIΔ has been developed by deletion of all the CpXI gene copies from the chromosome of the industrial xylose fermenting strain GSE16-T18, which carried 16 to 18 copies of CpXI. GSE16-T18 had been developed from the M315 strain through a series of evolutionary adaptation rounds in synthetic medium and in lignocellulose hydrolysate. Deletion of all the CpXI copies from the strain completely abolished the xylose fermentation performance. Reintroduction of xylose isomerase into these platform strains restored efficient xylose fermentation capacity. Therefore, these two strains provided us with a useful tool for screening of potential XylA genes from different sources for functional expression in yeast. Using these platform strains, we were able to screen several bacterial XylA genes for rapid xylose fermentation capacity, which resulted in the identification of several genes expressing xylose isomerase with superior performance.

Materials and Methods

Construction of Multi-Copy Plasmids Carrying XylA Genes

Each of the 14 bacterial XylA genes was synthesized in two blocks of about 700 bp with a 30 bp overlap to each other. The two gblock gene fragments were linked by PCR using a pair of primers each having a 30 bp tail sequence to create overlap to the 5' and 3' end of a linearized vector p426tef1. The vector p426tef1 (Mumberg et. al., 1995, Yeast vectors for controlled expression of heterologous protein in different genetic backgrounds. Gene, 156; 119-122) was linearized using PstI and HindIII restriction enzymes between the tef1 promoter and cyc1 terminator. The PCR fragment and the linearized vector were assembled using Gibson assembly cloning kit (New England BioLabs, USA), and transformed into chemically competent E. coli strain Top10 (Invitrogen). The plasmids were subsequently isolated from the E. coli using NucleoSpin® Plasmid EasyPure kit (MACHEREY-NEGEL GMBH & CO. KG, Germany). The isolated plasmids were transformed into the host yeast strain using standard LiAc/PEG method (18).

Deletion of CpXI from GSE16-T18

The strain GSE16-T18 carried between 16 and 18 copies of the CpXIgene that was originally inserted in two copies by replacing part of the PYK2 gene in chromosome XV. The CpXI gene was amplified in the chromosomal locus into multiple tandem repeats during an evolutionary engineering step (15).

The multiple copies of the XylA genes were deleted using a CRISPR/Cas9 based methodology. First, a single gRNA plasmid carrying two gRNA target sequences from either ends of the amplified XylA genes and a hygromycin resistance gene hph has been constructed. Next, two donor DNA fragments were made by PCR amplification of two selection marker genes, the kanamycin resistance gene kan and nourseothricin resistance marker nat. Each marker gene was flanked by sequences homologous to the upstream and downstream gRNA target sequences in the genome. After that, the GSE16-T18 strain was transformed with a Cas9 plasmid having a ble selection marker. The GSE16-T18-Cas9 strain expressing Cas9 was subsequently transformed with the gRNA plasmid and the two donor-DNA fragments. Transformants were selected only for the hph marker in the gRNA. Positive transformants expressing the hph resistance marker were evaluated for effective replacement of the multiple copies of the XylA gene with the two markers kan and nat, both phenotypically and by PCR. A strain that replaced all the XylA copies by a kan and a nat marker was selected, and the markers were subsequently removed by another CRISPR/Cas9 step using a gRNA plasmid that targets each of the kan and nat markers. A full length PYK2 sequence flanked by sequences upstream and downstream of the inserted markers in the genome was used as a donor DNA to cure the partially deleted PYK2 gene. The final strain devoid of any CpXI gene and carrying the full length PYK2 was referred to as GSE16-T18CpXIΔ/CpXA.

Optimization of the CRISPR/Cas9 Method for Genomic Integration of the XylA Genes Genomic integration of 2 to 4 copies of each of the XylA genes was performed using an optimized CRISPR/Cas9 system. First, a donor DNA was constructed in a multicopy plasmid carrying two XylA sequences flanked by sequences homologous to upstream and downstream sequences of the site of integration to trigger homologous recombination. The donor plasmid DNA (pDonor) was transformed into the yeast strain GSE16-T18CpXIΔ/CpXIΔ and selected directly on plates containing xylose as a carbon source. The pDonor plasmid carrying strains were then transformed with a gRNA plasmid with the hph marker and a Cas9 plasmid with the kan marker, and selected on YPD+geneticin and hygromycin. Transformants growing in the presence of both antibiotic resistance markers were transferred to a new YPD plate to be evaluated for the proper integration of the donor DNA into the genome. This was performed by PCR using a pair of primers annealing upstream and downstream of the insertion site. Once the insertion was confirmed, the strains were allowed to lose the plasmids by growing them in YPD medium for 5 days and then serially transferring the strains to a new YPD plate every 24 h. After 5 days, a sample was spread for single colonies and several colonies were evaluated for loss of the gRNA and Cas9 plasmids carrying the hph and kan markers, respectively. Colonies that lost both plasmids were checked by PCR to evaluate the loss of the donor plasmid since the donor plasmid was devoid of selection marker.

Small-Scale Fermentations

Small scale fermentations were performed essentially according to the protocol described previously (12). Briefly, cells were pre-grown in 5 ml YPD for 24 h. Subsequently, 1 ml of culture was transferred to 50 mL YPD in a 300 mL Erlenmeyer flask. After 24 h growth, cells were harvested and a 1 g DW/L amount of cells was inoculated into 50 mL YP medium containing 4% w/v xylose as a carbon source, in cylindrical tubes with cotton plugged rubber stopper and glass tubing. Cultures were continuously stirred with a magnetic rod at 120 rpm and incubated at 35° C. Progress of the fermentations was followed by measuring the weight due to $CO_2$ loss during the fermentation.

Results

Screening for XI Sequences that Support Growth of *S. cerevisiae* on Xylose as a Sole Carbon Source Expression in yeast of XIs originating from several species of bacteria has been reported in the last decade. Most of the enzymes failed to show reasonable enzymatic activity in *S. cerevisiae*. Only a limited number of XIs with good enzymatic activity is available to date. Since a large number of sequences exist in public databases such as NCBI, we explored sequence databases to search for XylA genes originating from diverse environments. We selected 16 sequences coding for XI from 16 bacterial species. The sequences varied from 62% to 96% identity to the sequence of *C. phytofermentans* XylA (Table 1), and between 50 and 55% to the sequence of *Piromyces* sp E2 XylA at the amino acid level.

Each sequence has been codon optimized and synthesized by IDT (Integrated DNA Technologies, Heverlee, Belgium). The codon-optimized genes were subsequently cloned into a yeast expression vector p426-tef1, under control of the tef1 promoter and Cyc1 terminator. For comparison, we also constructed a plasmid with the CpXI gene under control of the same promoter and terminator. The constructed plasmids were subsequently transformed into the platform strain M315CpXIΔ/CpXIΔ.

Transformants were selected in synthetic medium containing xylose as a carbon source (SCX plate). After 5 days at 30° C., 7 of the 14 transformants were able to grow on the SCX plate. Later, an additional 4 transformants grew into smaller colonies, after 7 days, indicating that the genes in these 4 additional transformants supported only slow growth on xylose. Nevertheless, a total of 11 out of the 16 genes tested were able to support growth in medium with xylose as a sole carbon source.

Confirmation of Correct Expression of the Genes

In order to confirm the presence of the expressed gene in the host strain, polymerase chain reaction (PCR) was performed using primers that specifically amplify each gene. As expected, a positive PCR result was obtained at the expected molecular weight of 1.2 kb for all the strains tested (data not shown). The negative control strains M315CpXIΔ/CpXIΔ and M315CpXI failed to show a PCR band, confirming the specificity of the PCR product.

Fermentation in Medium with Xylose

Since growth and fermentation are different traits, and frequently do not correlate well to one another, we evaluated all the 11 XylA transformants for fermentation performance in YP medium containing xylose as a sole carbon source. The first 7 XylA transformants were tested in a first batch of fermentation assays. Interestingly, all 7 XylA transformants showed rapid xylose fermentation capacity in YP medium containing 4% xylose (FIG. 1). A control strain with the gene CpXI was also evaluated for comparison. Two of the newly isolated genes (Es7XI and Cc10XI) sustained similar xylose fermentation performance as that of CpXI.

Subsequently, we repeated the fermentation test and included the four slow growing XylA transformants. As shown in FIG. 2, all 11 transformants were able to ferment xylose very well. The 7 strains showing rapid fermentation in the first fermentation test also showed the same rapid fermentation profile. In addition, two strains from the slowly growing second batch (Es5XI and Cl11XI) showed a similar fermentation profile as the first 7 rapidly fermenting strains. Therefore, 9 of the 11 transformants were able to support rapid xylose fermentation capacity in an industrial yeast strain background.

To confirm that the XylA transformants truly did not carry CpXI anymore, which is able to support high xylose fermentation capacity by itself, we tested all the cultures at the end of the fermentation by PCR using specific primers unique for the CpXI sequence. As expected, none of the cultures was positive for the CpXI gene, while the control strain that carries the CpXI plasmid was positive for the expected molecular weight band (data no shown).

Integration of XylA Genes into the Genome

Since plasmid copy number varies greatly in vivo during growth or fermentation, selection of the most active gene based on the fermentation performance of plasmid carrying strains can create a strong bias. Moreover, plasmids are unstable and are not an ideal gene expression system for industrial application. Hence, we performed genomic integration of 3 of the 8 genes supporting the best xylose fermentation capacity and also the gene CpXI for comparison. The integration was carried out into the genome of a robust industrial platform yeast strain GSE16-T18CpXIΔ/CpXIΔ, using a modified CRISPR/Cas9 system that we optimized for a single step transformation and for efficient integration of foreign genes in 2 to 4 copies, as described in the methods section. Using this methodology, we were able to stably integrate 2 to 4 copies of each of the genes at an intergenic region downstream of TYE7 and upstream of the tRNA gene tP(UGG)O3 in chromosome XV. Proper integration of the genes in the genome was confirmed by PCR (FIG. 3).

Fermentation Performance after XylA Genomic Integration

The fermentation performance of the strains carrying 2 to 4 copies of each XylA gene has been evaluated in YP medium with xylose as sole carbon source. As shown in FIG. 4, strains carrying either the Es7XI, Cs8XI or Fm9XI gene in the genome showed high xylose fermentation capacity. Strains carrying Cs8XI and Fm9XI showed from the beginning a comparable xylose fermentation rate as the strain carrying CpXI, while the strain carrying Es7XI showed a delay at the beginning of the fermentation but later recovered a high xylose fermentation rate. Although the strain with two copies of Cs8XI showed a slightly slower xylose fermentation rate than the strain with two copies of CpXI, it showed the highest rate of fermentation during the exponential phase of fermentation (FIG. 4). Moreover, the strains with 4 copies of Cs8XI fermented at a higher rate than the strain with the same number of copies of CpXI.

Conclusion

Eleven of the 16 newly identified XylA genes confer very good xylose fermentation performance in an industrial yeast strain when expressed from a multi-copy plasmid under control of the Tef1 promoter and Cyc1 terminator. Except for the XylA gene obtained from *L. phytofermentans*, which has 96% sequence identity with that of CpXI, all the functionally expressed XylA genes lack significant sequence identity with any of the Xylose Isomerases that have been actively expressed to date. The bacterial species from which these XylA genes have been obtained are isolates from diverse environments. Though most of the species inhabit environments that are rich in plant matter, which explains their cellulolytic capacity, the bacterium *M. indolicus* is a non-cellulolytic organism that has been isolated from the female genital tract (17). From an evolutionary point of view, this would indicate that there is no correlation with the functionality of the Xylose Isomerase, since there is no need for the XI to remain active in environment lacking hemicellulose. On the other hand, it cannot be excluded that the bacterium *M. indolicus* also lives in environments where xylose utilization is important for its survival but not lignocellulolytic capacity.

Three of the 11 XylA genes were studied after their integration into the genome. The Cs8XI gene was among the best to confer xylose fermentation capacity to the platform industrial strain when integrated in 2 or 4 copies. This gene is derived from an acetone-butanol producing bacterial species *C. saccharoperbutylacetonicum*. Although the bacterium is known to utilize xylose, the XI gene from this organism has never been expressed in the yeast *S. cerevisiae*.

On the other hand, the gene Fm9XI has previously been expressed in yeast (WO 2010/074577). Interestingly, the Cs8XI and Fm9XI XylA genes have only 68% sequence identity at the amino acid level. The low sequence identity of the two XylA genes is not surprising since the two source organisms are unrelated. Cs8XI is therefore a novel gene that confers excellent xylose fermentation capacity in yeast with chromosomal integration of only 2 to 4 copies. Integration of additional copies of the gene might further improve the xylose fermentation capacity. Furthermore, integration of the other identified genes in this work into the genome of the platform strain is important for stable expression of the genes and may also result in high xylose fermentation capacity.

Example 2

Performance of Es7XI and Cc10XI in Strain MDS130

Figure 5A:
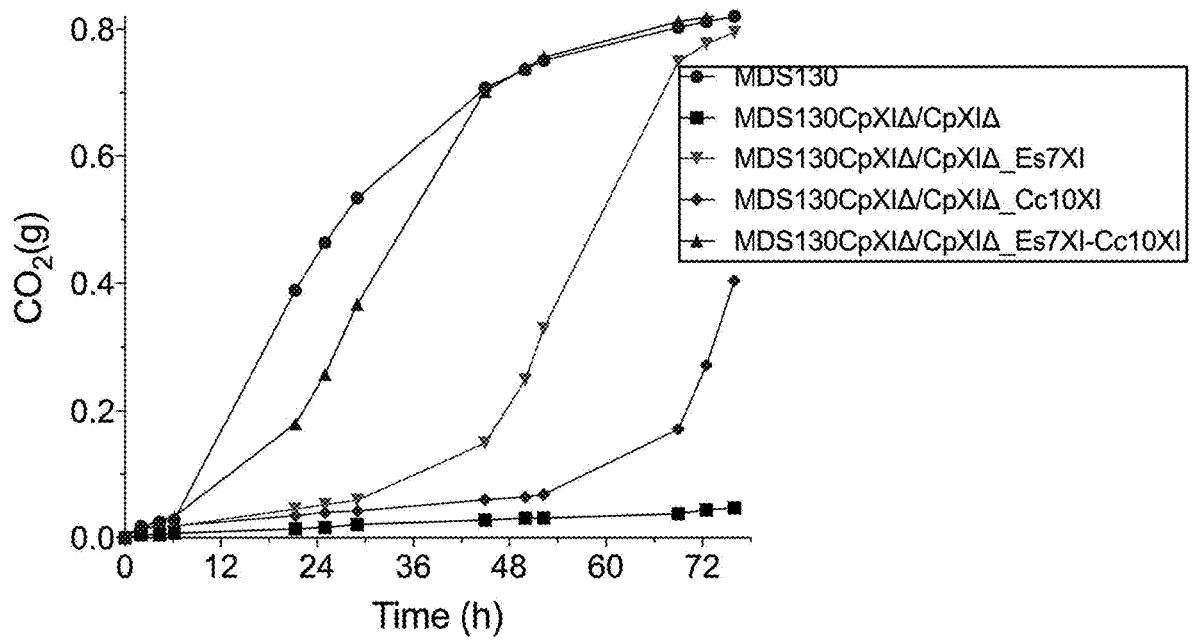

We further improved the strain GSE16-T18 for improved xylose fermentation and inhibitor tolerance by genome shuffling and evolutionary adaption. Strain MDS130 has thus been selected showing highly improved xylose fermentation capacity in inhibitor-rich hydrolysates. Afterwards, we completely knocked out the CpXI genes from the genome of MDS130 using the CRISPR/Cas9 technique as described above in the section "deletion of CpXI from GSE16-T18". As expected, the knockout strain MDS130CpXIΔ/CpXIΔ was not able to utilize xylose (FIG. 5A).

Next, we introduced the two best performing novel XI genes Es7XI and Cc10XI into the genome of MDS130CpXIΔ/CpXIΔ downstream of TYE7 gene in chromosome XV. With only two copies of each gene introduced, the deletion strain was able to utilized xylose but at a slower rate compared to the original MDS130 strain that carried about 18 copies of CpXI. In order to evaluate if combining the two genes improved xylose fermentation performance, we introduced additional 4 copies of Cc10XI into strain carrying two copies of Es7X. This resulted in significant improvement of the fermentation rate, close to the performance of strain MDS130 (FIG. 5A).

Figure 5B:
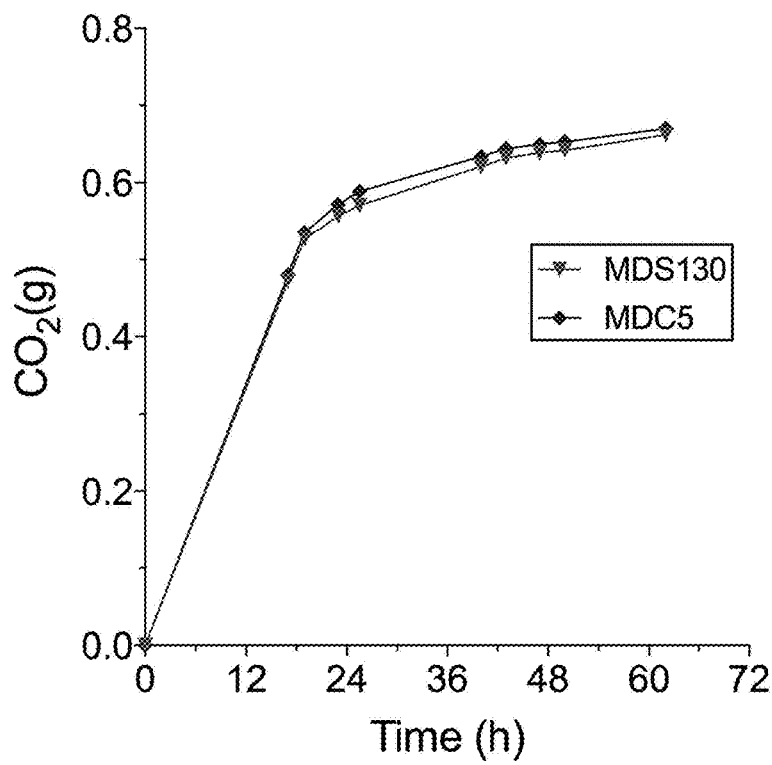

We have previously shown that a gene of interest adjacent to an ARS sequence is frequently amplified when cells are grown in a selective pressure requiring high expression of the gene of interest (WO2016026954). For that reason, we introduced Ex7XI about 2000 nucleotide upstream of ARS1529 in two copies and evolved in YP+4% xylose to induce chromosomal amplification. After 3 weeks, single cells isolates were evaluated and strain MDC5 that performed best from the tested single cell isolates has been selected. Gene copy number analysis by qPCR analysis showed that this strain carried about 12 copies of Es7XI. The performance of strain MDC5 with 12 copies of Es7XI was similar to that of MDS130 that carried about 18 copies of CpXI (FIG. 5B). This shows the superior performance of Es7XI over CpXI, at least in the strain background tested.

TABLE 2

CLUSTAL alignment of xylose isomerase amino acid sequences by MUSCLE (3.8)

```
PiXI    MAKEYFPQIQKIKFEGKDSKNPLAFHYYDAEKEVMGKKMKDWLRFAMAWWHTLCAEGADQ
Cc10XI  -MKEYFSNIPKVRYEGPDSKNPFAFKFYNPEEKIAGKTMREQLKFSLAYWHTLDAEGTDM
Am6XI   -MREHFLEINKIKFEGGDSTNPLAFKYYDANRIVAGKKMKDHLRFALSYWHTLTGNGTDP
Fm9XI   --MEFFKGIDKVKYEGVKTNNLLAFAHYNPEEVILGKKMKDHLKFAMSYWHTLTGEGTDP
Cs8XI   -MKEYFGNVSKINYEGPGSKNPYSFKYYNPDEVIGGKTMKEHLRFSLSYWHTLTANGADP
Cl11XI  -MAEFFKGIGVIPFEGADSVNPLAFKHYNKDEKVGDKTMAEHLRFAMSYWHTLCAEGGDP
Pcd12XI -MSEIFKGIGQIKFEGVKSDNELAFRYYNPEQVVGNKTMKEHLRFAMSYWHTLCGEGNDP
```

TABLE 2-continued

CLUSTAL alignment of xylose isomerase amino acid sequences by MUSCLE (3.8)

```
Es7XI    ---MYFNNIEKIKFEGVNSKNPLAFKYYDADRIIAGKKMSEHLKFAMSYWHTMCADGTDM
Es5XI    -MVNGLTNIPPVKFEGRDSKKALSFKYYNPDEMIQGKKMKDYLKFAMSYWHTLCGDGTDP
Mi3XI    --MKFFENVPKVKYEGSKSTNPFAFKYYNPEAVIAGKKMKDHLKFAMSWWHTMTATGQDQ
Ca2XI    -MKEYFKGIPEVKYEGKDSINPFAFKFYDAKRVIDGKSMEEHLKFAMSWWHTMTATGTDP
Lp1XI    -MKNYFPNVPEVKYEGPNSTNPFAFKYYDAERIVAGKTMKEHCRFALSWWHTLCAGGADP
CpXI     -MKNYFPNVPEVKYEGPNSTNPFAFKYYDANKVVAGKTMKEHCRFALSWWHTLCAGGADP
              :    :   :**   :  :  :* .*: .    .*.* :   .*:::***: .  *  *

PiXI     FGGGTKSFPWNEGTDAIEIAKQKVDAGFEIMQKLGIPYYCFHDVDLVSEGNSIEEYESNL
Cc10XI   FGRATMDKSFGETD-PMAIYKNKAYAAFELMDKLDIDYFCFHDRDIAPEGPTLSETNKNL
Am6XI    FGQPTMERDYNSLD-GIELSKARVDAAFELMTKLGIEFFCFHDLDIAPEGNSLQEKLDNL
Fm9XI    FGNATMDREWNEYT-PMEKAKARVKAGFEFMEKLGLEYFCFHDKDIAPEAETLEEYHRNL
Cs8XI    FGAGTMLRPWDDITNEMDLAKARMEAAFELMDKLNIEYFCFHDRDIAPEGKTLQETNENL
Cl11XI   FGSTTAARPWNQIANPIEMAKAKVDAGFEFMQKLGIEYFCFHDRDIAPEGKDLAETNQIL
Pcd12XI  FGVGTVERPWNNITDPIEIAKIKVDAGFEFMSKMGIEYFCFHDRDIAPEGRDLEETNKIL
Es7XI    FGRGTINKSFGGKT-AIEIYEHKVYAAFELMEKLGMQYFCFHDRDIAPEGATLKETNENL
Es5XI    FGSSTIDRDYSGQT-PMEKAKTKADVAFALMQILGIEYFCFHDLDIAPTGNSLKELKNNL
Mi3XI    FGSGTMSRIYDGQTEPLALAKARVDAAFDFMEKLNIEYFCFHDADLAPEGNSLQERNENL
Ca2XI    FGAGTIDRNYGQTE-SMEIARAKVDAAFELMKKLGIKYFCFHDVDIVPEGKDLKETKENL
Lp1XI    FGVTTMDRSYGNITDPMEFAKAKVDAGFELMTKLGIEYFCFHDADIAPEGENFEESKKNL
CpXI     FGVTTMDRTYGNITDPMELAKAKVDAGFELMTKLGIEFFCFHDADIAPEGDTFEESKKNL
              **  *     *       :.        . ..* :*  ::: ::****  *:..  .  :   *         *

PiXI     KAVVAYLKEKQKETGIKLLWSTANVFGHKRYMNGASTNPDFDVVARAIVQIKNAIDAGIE
Cc10XI   DEIVSLLKKLMAEHNKKLLWGTANTFSHPRYVHGAGTSCNASVFAFAAAQIKKAIEITKE
Am6XI    DTILERIEDKMKETGIKCLWGTTNAFSHPRFMHGAATSPNADVFAFAAAQVKKALEITHR
Fm9XI    DEIVDLIEEEMKRTGILLWGTSNMFSHPRFMHGAATSCNADVFAYAAAQVKKALEITKR
Cs8XI    DEIVAYCKELMKKYNKKLLWGTANCFTNPRYVHGAGTSCNADVFAYAAAQIKKALEVTKE
Cl11XI   DEVVAYIKVKMQETGIKLLWGTANCFNNKRFMHGAGTTCNAEVFAYAAAQIKKAIEVTKE
Pcd12XI  DEIVEYIKVNMEKTGIKLLWGTANMFGNPRFVHGASTTCNADVYAYAAAQVKKAMEITKY
Es7XI    ERIVPIIKSEMKRTGINCFNHPRYMCGAGTAPSADVFAYAAAQIKKAIEITVE
Es5XI    IEITDYIKGLMDKTGIKLLWGTANCFSHPRYMNGAGTSPQADIFACAAAQIKNAIDATIK
Mi3XI    QEMVSYLKQKMAGTSIKLLWGTSNCFSNPRFMHGAATSCEADVFAWTATQLKNAIDATIA
Ca2XI    SVIVDYIEEKMKGTDIKLLWGTANCFSSPRYMHGAGTSCNADSFSYAASQIKNAIDATIQ
Lp1XI    FVIVDYIKEKMDQTGIKLLWGTANNFGHPRFMHGASTCNADVFAYAAAKIKNALDATIK
CpXI     FEIVDYIKEKMDQTGIKLLWGTANNFSHPRFMHGASTCNADVFAYAAAKIKNALDATIK
             :              :    .  *  **.*:*  *      *::  **.*    . .    :    :    *:*::

PiXI     LGAENYVFWGGREGYMSLLNTDQKREKEHMATMLTMARDYARSKGFKGTFLIEPKPMEPT
Cc10XI   LDGCGYVFWGGREGYETLLNTDMELELDNMARLLKMARDYARSIGFKGEFFIEPKPKEPT
Am6XI    LRGENYVFWGGREGYETLLNTDIALENDNLAKFLKMAKDYARNIGFEGQFLIEPKPKEPT
Fm9XI    LNGTGYVFWGGREGYETLLNTDIGLELDNLARFLQMAVDYAKKIGFEGQFFIEPKPKEPT
Cs8XI    LGGENYVFWGGREGYETLLNTDMGLELDNFARLLQMAVDYAKEIGFTGQFLIEPKPKEPT
Cl11XI   LGGENYVFWGGREGYETLLNTDTGLELDNFARLLQMAVDYAKEIGFTGQFLIEPKPKEPT
Pcd12XI  LGGENFVFWGGREGYETLLNTNTELEMDNFARFLQMAVDYAKEIGFTGQFLIEPKPKEPT
Es7XI    LGGQGYVFWGGREGYDTILNTDMAKEQDNMAYLMRMAVDYGRSIGFTGDFYIEPKPKEPT
Es5XI    LGGTGYVFWGGREGYETLLNTNMEIELDNMAKLMHMAVDYARSKGFTGDFYIEPKPKEPT
Mi3XI    LGGKGYVFWGGREGYETLLNTDVGLEMDNYARMLKMAVAYARSKGYTGDFYIEPKPKEPT
Ca2XI    LGGSGYVFWGGREGYETLLNTDMGFELDNMARLMKMAVKYARKKGFNGDFYIEPKPKEPT
Lp1XI    LGGKGYVFWGGREGYETLLNTDLGLELDNMARLMKMAVEYGRANGFDGDFYIEPKPKEPT
CpXI     LGGKGYVFWGGREGYETLLNTDLGLELDNMARLMKMAVEYGRANGFDGDFYIEPKPKEPT
             *  .  .:*********   ::***:    *  ::  *  :: **  *..    *:  *  * *****  ***

PiXI     KHQYDVDTETAIGFLKAHNLDKDFKVNIEVHNATLAGHTFEHELACAVDAGMLGSIDANR
Cc10XI   KHQYDYDVSTVLAFLRKYGLDKVFKVNIEANHATLAQHTFQHELRVARINGVLGSVDANQ
Am6XI    KHQYDFDTMTVLGFLRKYNLIDDFKLNIEANHATLAGHTFQHELAMARINGVLGSVDANQ
Fm9XI    KHQYDFDTTTVLEFLRKYNLDKYFKMNIEANHATLAGHTFQHELCTARINGVFGSIDANQ
Cs8XI    KHQYDFDTATVLGFLKKYNLDKYFKVNIEANHATLAQHTFQHELNFARINNFLGSIDANQ
Cl11XI   KHQYDFDTATVLAFLRKYNLDTYFKMNIEANHATLAGHTFQHELNMSRINNVLGSIDANQ
Pcd12XI  KHQYDFDTATVLGFLRKYNLDKYFKMNIEANHATLAGHTFQHELNIARINNVLGSIDANQ
Es7XI    KHQYDFDVSTVLAFLRKYDLDKDFKMNIEANHATLAGHTFQHELRVARDNGVFGSIDANQ
Es5XI    KHQYDFDVATVVGFLRKYGLDKDFKMNIEANHATLAGHTFQHELNVARVNNFGSIDANQ
Mi3XI    KHQYDFDVATCVAFLEKYDLMRDFKVNIEANHATLAGHTFQHELRMARTFGVFGSVDANQ
Ca2XI    KHQYDFDAATVIGFLRKYDLMDDFKLNIEANHATLAGHTFPHELAVARINGVFGSVDANQ
Lp1XI    KHQYDFDTATVLGFLRKYGLEKDFKMNIEANHATLAGHTFEHELAMARVNGVFGSVDANQ
CpXI     KHQYDFDTATVLAFLRKYGLEKDFKMNIEANHATLAGHTFEHELAMARVNGAFGSVDANQ
             *****  *.  *    : **       :.*     **:***.******   ***   ***          :      .   :**:***.

PiXI     GDYQNGWDTDQFPIDQYELVQAWMEIIRGGGFVTGGTNFDAKTRRNSTDLEDIIIAHVSG
Cc10XI   GDVMLGWDTDQFPTNVYDTALAMYEILKNGGLPSGGLNFDSKNRRGSFEPEDIFHGFIAG
Am6XI    GDLLLGWDTDQFPTNIYDATLSMYEVLKNGGIAPGGLNFDAKVRRGSFKPDDLFIAYIVG
Fm9XI    GDMLLGWDTDQFPTNVYDAVLAMYETLLAGGFKEGGLNFDAKVRRGSFEPKDLFYAYISG
Cs8XI    GDPMLGWDTDQFPTNIYDATLAMYEILKNGGLAPGGVNFDAKRRASFEKEDLFLAYIAG
Cl11XI   GDLMLGWDTDQFPTNIYDATMAMYEVLKAGGIAPGGFNFDSKVRRGSFEEADLFIAYIAG
Pcd12XI  GDLLLGWDTDQFPTNIYDATLAMYEVLKQGGIAPGGFNFDSKVRRASFEVEDLFLAYIAG
Es7XI    GDMLLGWDTDQFPTDLYSTTMCMYEVLKQGGFTNGGLNFDAKARRASNTYEDVFLSYIAG
Es5XI    GDLLLGWDTDQFPTNVYDTTLCMLEVIKAGGFTNGGLNFDAKVRRASYTMEDIILAYISG
Mi3XI    GDSNLGWDTDQFPGNIYDTTLAMYEILKAGGFTNGGLNFDAKVRRPSFTPEDIAYAYILG
```

TABLE 2-continued

CLUSTAL alignment of xylose isomerase amino acid sequences by MUSCLE (3.8)

```
Ca2XI     GDSLLGWDTDQFPTDVKEATLSMLEIIKAGGFTNGGLNFDAKVRRPSFTFEDIVYGYISG
Lp1XI     GDPNLGWDTDQFPTDVHSATLAMLEVLKAGGFTNGGLNFDAKVRRGSFEFDDIAYGYIAG
CpXI      GDPNLGWDTDQFPTDVHSATLAMLEVLKAGGFTNGGLNFDAKVRRGSFEFDDIAYGYIAG
          **  ********  :   . .  * :  **:  ** ***:* ** *    *:  ..: *

PiXI      MDAMARALENAAKLLQESPYTKMKKERYASFDSGIGKDFEDGKLTLEQVYEYGKKNGEP-
Cc10XI    MDAFALGLRIADRIIRDGRLEQFVKDRYKSYQSGIGADIVSGRAKIEDLEKYALKLGEVN
Am6XI     MDTFAKGLLVADKLLTDGVLENFVTKRYESYTAGIGKKIIEDATSFEELAEYALKHDKI-
Fm9XI     MDTFAKGLKVAAKLIEDGTFEKIKVERYSSYTTGIGKQIVNGEVGFEELSKYALTNGVK-
Cs8XI     MDTFAKGLKVAHKLLENGELENFIKNKYASFSEGIGKEIVEGKVGLKELEAYALKNNEI-
Cl11XI    MDTFAKGLKVAYNLLKDGVLEDFVADRYASFNEGIGKDIVSGNVGFKELEAYALKQQPI-
Pcd12XI   MDTFAKGLLIAHKLLEDEVFENFTKERYASFSEGIGKDIVEGKVGFKELESYALQMPVI-
Es7X1     MDAFAYGLIVADKIISDGVMDKFVENRYSSYTEGIGKKIADKQTSLAELEQYTLTNGEP-
Es5X1     MDTFALGLKIANKIIEDGRIDEFVSRRYASYKTGIGADIIAGRTNLEELEKYALELPPV-
Mi3XI     MDTFALGLIKAQQLIEDGRIDRFVAEKYASYKSGIGAEILSGKTSLPELEAYALKKGEP-
Ca2XI     MDTFALGLIKAYEVIEDGRIDEFIEKRYASYESGIGKKILNNEVTLEELEAYTLENKER-
Lp1XI     MDTFALGLIKAAEIIEDGRIAKFVEDRYASYKTGIGKAIVDGTTSLEELEQYVLTHNEP-
CpXI      MDTFALGLIKAAEIIDDGRIAKFVDDRYASYKTGIGKAIVDGTTSLEELEQYVLTHSEP-
          **::* .* *   :: :      :    .* *:  ***  :        : :: *

PiXI      KQTSGKQELYEAIVA--MYQ-------
Cc10XI    AIGSGRQEYLEDILNSIMFGK------
Am6XI     VLESGRQEMLEDIVNRYIYK-------
Fm9XI     KNSSGRQEMLENILNRYIYE-------
Cs8XI     TNKSGRQELLEAIVNQYIFED------
Cl11XI    VNKSGRQEWLETVVNQYIYNNK-----
Pcd12XI   KNKSGRQEMLESILNRYIYEVDTISNK
Es7X1     TAESGKQEYLEALVNQYIISAGREL--
Es5X1     EPHPGKQEYLEAVFNNVMFTV------
Mi3XI     KLYSGRQEYLESVVNNVIFNGNL----
Ca2XI     PMESGRQEYLETILNQILYK-------
Lp1XI     VMQSGRQEVLESIVNNILFR-------
CpXI      VMQSGRQEVLETIVNNILFR-------
           .*.**   * :.   :
```

REFERENCES

1. Zaldivar J, Nielsen J, Olsson L. Fuel ethanol production from lignocellulose: a challenge for metabolic engineering and process integration. Appl Microbiol Biotechnol. 2001 July; 56(1-2):17-34.
2. Hahn-Hägerdal B, Karhumaa K, Fonseca C, Spencer-Martins I, Gorwa-Grauslund M F. Towards industrial pentose-fermenting yeast strains. Appl Microbiol Biotechnol. 2007 April; 74(5):937-53.
3. Lau M W, Gunawan C, Balan V, Dale B E. Comparing the fermentation performance of *Escherichia coli* KO11, *Saccharomyces cerevisiae* 424A(LNH-ST) and *Zymomonas mobilis* AX101 for cellulosic ethanol production. Biotechnol Biofuels. 2010 May 27; 3(1):11.
4. Bettiga M, Hahn-Hagerdal B, Gorwa-Grauslund M F. Comparing the xylose reductase/xylitol dehydrogenase and xylose isomerase pathways in arabinose and xylose fermenting *Saccharomyces cerevisiae* strains. Biotechnol Biofuels. 2008 Oct. 23; 1(1):16.
5. Hector R E, Mertens J A, Bowman M J, Nichols N N, Cotta M A, Hughes S R. *Saccharomyces cerevisiae* engineered for xylose metabolism requires gluconeogenesis and the oxidative branch of the pentose phosphate pathway for aerobic xylose assimilation. Yeast. 2011 Sep. 1; 28(9):645-60.
6. Hou J, Suo F, Wang C, Li X, Shen Y, Bao X. Fine-tuning of NADH oxidase decreases byproduct accumulation in respiration deficient xylose metabolic *Saccharomyces cerevisiae*. BMC Biotechnol. 2014 Feb. 14; 14(1):13.
7. Jeppsson M, Bengtsson O, Franke K, Lee H, Hahn-Hagerdal B, Gorwa-Grauslund M F. The expression of a *Pichia stipitis* xylose reductase mutant with higher K M for NADPH increases ethanol production from xylose in recombinant *Saccharomyces cerevisiae*. Biotechnol Bioeng. 2006; 93(4):665-73.
8. Walfridsson M, Bao X, Anderlund M, Lilius G, Bulow L, Hahn-Hagerdal B. Ethanolic fermentation of xylose with *Saccharomyces cerevisiae* harboring the *Thermus thermophilus* xylA gene, which expresses an active xylose (glucose) isomerase. Appl Environ Microbiol. 1996 December; 62(12):4648-51.
9. Kuyper M, Harhangi H R, Stave A K, Winkler A A, Jetten M S M, de Laat W T A M, et al. High-level functional expression of a fungal xylose isomerase: the key to efficient ethanolic fermentation of xylose by *Saccharomyces cerevisiae*? FEMS Yeast Res. 2003; 4(1):69-78.
10. Peng B, Huang S, Liu T, Geng A. Bacterial xylose isomerases from the mammal gut Bacteroidetes cluster function in *Saccharomyces cerevisiae* for effective xylose fermentation. Microb Cell Factories. 2015 May 17; 14(1):70.
11. Brat D, Boles E, Wiedemann B. Functional Expression of a Bacterial Xylose Isomerase in *Saccharomyces cerevisiae*. Appl Environ Microbiol. 2009 Feb. 13; 75(8):2304-11.
12. Demeke M M, Dietz H, Li Y, Foulquié-Moreno M R, Mutturi S, Deprez S, et al. Development of a D-xylose fermenting and inhibitor tolerant industrial *Saccharomyces cerevisiae* strain with high performance in lignocellulose hydrolysates using metabolic and evolutionary engineering. Biotechnol Biofuels. 2013 Jun. 21; 6(1):89.
13. Glanemann C, Loos A, Gorret N, Willis L B, O'Brien X M, Lessard P A, et al. Disparity between changes in mRNA abundance and enzyme activity in *Corynebacterium glutamicum*: implications for DNA microarray analysis. Appl Microbiol Biotechnol. 2002 Dec. 21; 61(1):61-8.

14. Glanemann03.pdf [Internet]. [cited 2016 Nov. 6]. Available from: web.mit.edu/biology/sinskey/www/GlanemannO3.pdf
15. Demeke M M, Foulquié-Moreno M R, Dumortier F, Thevelein J M. Rapid Evolution of Recombinant *Saccharomyces cerevisiae* for Xylose Fermentation through Formation of Extra-chromosomal Circular DNA. PLoS Genet. 2015 Mar. 4; 11 (3):e1005010.
16. Demeke M M, Dumortier F, Li Y, Broeckx T, Foulquié-Moreno M R, Thevelein J M. Combining inhibitor tolerance and D-xylose fermentation in industrial *Saccharomyces cerevisiae* for efficient lignocellulose-based bioethanol production. Biotechnol Biofuels. 2013 Aug. 26; 6(1):120.
17. Austin M N, Rabe L K, Srinivasan S, Fredricks D N, Wiesenfeld H C, Hillier S L. *Mageeibacillus indolicus* gen. nov., sp. nov.: A novel bacterium isolated from the female genital tract. Anaerobe. 2015 April; 32:37-42.
18. Gietz R D, Schiestl R H, Willems A R, Woods R A. Studies on the transformation of intact yeast cells by the LiAc/SS-DNA/PEG procedure. Yeast. 1995 Apr. 15; 11(4):355-60.

The invention claimed is:

1. A genetically engineered fungal cell that is able to grow on xylose as a sole carbon source, wherein the fungal cell comprises a polynucleotide encoding a xylose isomerase having at least 95% sequence identity with SEQ ID NO: 7.

2. The fungal cell according to claim 1, wherein the fungal cell is a yeast or a filamentous fungus of a genus selected from the group consisting of *Saccharomyces, Kluyveromyces, Candida, Pichia, Schizosaccharomyces, Hansenula, Kloeckera, Schwanniomyces, Yarrowia, Kazachstania Naumovia, Aspergillus, Trichoderma, Humicola, Acremonium, Fusarium*, and *Penicillium*.

3. The fungal cell according to claim 2, wherein the fungal cell is a yeast that is capable of performing anaerobic alcoholic fermentation.

4. The fungal cell according to claim 3, wherein the yeast belongs to a *Saccharomyces* species selected from the group consisting of *S. cerevisiae, S. bayanus, S. bulderi, S. cervazzii, S. cariocanus, S. castellii, S. dairenensis, S. exiguus, S. kluyveri, S. kudriazevii, S. mikatae, S. paradoxus, S. pastorianus, S. turicensis* and *S. unisporus*.

5. The fungal cell according to claim 1, wherein the polynucleotide encoding the xylose isomerase is operably linked to a promoter that is insensitive to catabolite repression and that does not require xylose for induction.

6. The fungal cell according to claim 1, wherein the fungal cell is further genetically modified to comprise a polynucleotide encoding a xylulose kinase.

7. The fungal cell according to claim 1, wherein the fungal cell further comprises at least one genetic modification that results in a characteristic selected from the group consisting of:
a) increased tolerance to ethanol;
b) increased tolerance to acetic acid;
c) reduced production of glycerol;
d) increased xylose to ethanol fermentation rate; and,
e) increased thermotolerance.

8. The fungal cell according to claim 1, wherein the polynucleotide encoding the polypeptide with xylose isomerase activity is integrated into the genome of the fungal cell.

9. The fungal cell according to claim 1, wherein the fungal cell is suitable for large scale industrial fermentation.

10. The fungal cell according to claim 1, wherein the fungal cell is a diploid, aneuploid, or polyploid cell.

11. The fungal cell according to claim 1, wherein the fungal cell has the ability to produce at least one fermentation product selected from the group consisting of ethanol, lactic acid, 3-hydroxy-propionic acid, acrylic acid, acetic acid, succinic acid, citric acid, amino acids, 1,3-propanediol, ethylene, glycerol, butyric acid, caproate, butanol, glyoxylate, muconic acid, fatty alcohols, fatty acids, β-lactam antibiotics, and cephalosporins.

12. The fungal cell of claim 6, wherein the xylulose kinase is XKS1.

* * * * *

SEQUENCE LISTING

```
<160> NUMBER OF SEQ ID NOS: 34

<210> SEQ ID NO 1
<211> LENGTH: 438
<212> TYPE: PRT
<213> ORGANISM: Lachnoclostridium phytofermentans

<400> SEQUENCE: 1

Met Lys Asn Tyr Phe Pro Asn Val Pro Glu Val Lys Tyr Glu Gly Pro
1               5                   10                  15

Asn Ser Thr Asn Pro Phe Ala Phe Lys Tyr Tyr Asp Ala Glu Arg Ile
            20                  25                  30

Val Ala Gly Lys Thr Met Lys Glu His Cys Arg Phe Ala Leu Ser Trp
        35                  40                  45

Trp His Thr Leu Cys Ala Gly Ala Asp Pro Phe Gly Val Thr Thr
    50                  55                  60

Met Asp Arg Ser Tyr Gly Asn Ile Thr Asp Pro Met Glu Phe Ala Lys
65                  70                  75                  80

Ala Lys Val Asp Ala Gly Phe Glu Leu Met Thr Lys Leu Gly Ile Glu
                85                  90                  95

Tyr Phe Cys Phe His Asp Ala Asp Ile Ala Pro Glu Gly Glu Asn Phe
            100                 105                 110

Glu Glu Ser Lys Lys Asn Leu Phe Val Ile Val Asp Tyr Ile Lys Glu
        115                 120                 125

Lys Met Asp Gln Thr Gly Ile Lys Leu Leu Trp Gly Thr Ala Asn Asn
    130                 135                 140

Phe Gly His Pro Arg Phe Met His Gly Ala Ser Thr Ser Cys Asn Ala
145                 150                 155                 160

Asp Val Phe Ala Tyr Ala Ala Ala Lys Ile Lys Asn Ala Leu Asp Ala
                165                 170                 175

Thr Ile Lys Leu Gly Gly Lys Gly Tyr Val Phe Trp Gly Gly Arg Glu
            180                 185                 190

Gly Tyr Glu Thr Leu Leu Asn Thr Asp Leu Gly Leu Glu Leu Asp Asn
        195                 200                 205

Met Ala Arg Leu Met Lys Met Ala Val Glu Tyr Gly Arg Ala Asn Gly
    210                 215                 220

Phe Asp Gly Asp Phe Tyr Ile Glu Pro Lys Pro Lys Glu Pro Thr Lys
225                 230                 235                 240

His Gln Tyr Asp Phe Asp Thr Ala Thr Val Leu Gly Phe Leu Arg Lys
                245                 250                 255

Tyr Gly Leu Glu Lys Asp Phe Lys Met Asn Ile Glu Ala Asn His Ala
            260                 265                 270

Thr Leu Ala Gly His Thr Phe Glu His Glu Leu Ala Leu Ala Arg Val
        275                 280                 285
```

-continued

```
Asn Gly Val Phe Gly Ser Val Asp Ala Asn Gln Gly Asp Pro Asn Leu
    290                 295                 300

Gly Trp Asp Thr Asp Gln Phe Pro Thr Asp Val His Ser Ala Thr Leu
305                 310                 315                 320

Ala Met Leu Glu Val Leu Lys Ala Gly Gly Phe Thr Asn Gly Gly Leu
                325                 330                 335

Asn Phe Asp Ala Lys Val Arg Arg Gly Ser Phe Glu Phe Asp Asp Ile
            340                 345                 350

Ala Tyr Gly Tyr Ile Ala Gly Met Asp Thr Phe Ala Leu Gly Leu Ile
        355                 360                 365

Lys Ala Ala Glu Ile Ile Glu Asp Gly Arg Ile Ala Lys Phe Val Glu
    370                 375                 380

Asp Arg Tyr Ala Ser Tyr Lys Thr Gly Ile Gly Lys Ala Ile Val Asp
385                 390                 395                 400

Gly Thr Thr Ser Leu Glu Glu Leu Glu Gln Tyr Val Leu Thr His Asn
                405                 410                 415

Glu Pro Val Met Gln Ser Gly Arg Gln Glu Val Leu Glu Ser Ile Val
            420                 425                 430

Asn Asn Ile Leu Phe Arg
        435

<210> SEQ ID NO 2
<211> LENGTH: 437
<212> TYPE: PRT
<213> ORGANISM: Clostridium algidicarnis
<400> SEQUENCE: 2

Met Lys Glu Tyr Phe Lys Gly Ile Pro Glu Val Lys Tyr Glu Gly Lys
1               5                   10                  15

Asp Ser Ile Asn Pro Phe Ala Phe Lys Phe Tyr Asp Ala Lys Arg Val
            20                  25                  30

Ile Asp Gly Lys Ser Met Glu Glu His Leu Lys Phe Ala Met Ser Trp
        35                  40                  45

Trp His Thr Met Thr Ala Thr Gly Thr Asp Pro Phe Gly Ala Gly Thr
    50                  55                  60

Ile Asp Arg Asn Tyr Gly Gln Thr Glu Ser Met Glu Ile Ala Arg Ala
65                  70                  75                  80

Lys Val Asp Ala Ala Phe Glu Leu Met Lys Lys Leu Gly Ile Lys Tyr
                85                  90                  95

Phe Cys Phe His Asp Val Asp Ile Val Pro Glu Gly Lys Asp Leu Lys
            100                 105                 110

Glu Thr Lys Glu Asn Leu Ser Val Ile Val Asp Tyr Ile Glu Glu Lys
        115                 120                 125

Met Lys Gly Thr Asp Ile Lys Leu Leu Trp Gly Thr Ala Asn Cys Phe
    130                 135                 140

Ser Ser Pro Arg Tyr Met His Gly Ala Gly Thr Ser Cys Asn Ala Asp
145                 150                 155                 160

Ser Phe Ser Tyr Ala Ala Ser Gln Ile Lys Asn Ala Ile Asp Ala Thr
                165                 170                 175

Ile Gln Leu Gly Gly Ser Gly Tyr Val Phe Trp Gly Gly Arg Glu Gly
            180                 185                 190

Tyr Glu Thr Leu Leu Asn Thr Asp Met Gly Phe Glu Leu Asp Asn Met
        195                 200                 205

Ala Arg Leu Met Lys Met Ala Val Lys Tyr Ala Arg Lys Lys Gly Phe
    210                 215                 220
```

```
Asn Gly Asp Phe Tyr Ile Glu Pro Lys Pro Lys Glu Pro Thr Lys His
225                 230                 235                 240

Gln Tyr Asp Phe Asp Ala Ala Thr Val Ile Gly Phe Leu Arg Lys Tyr
                245                 250                 255

Asp Leu Met Asp Asp Phe Lys Leu Asn Ile Glu Ala Asn His Ala Thr
            260                 265                 270

Leu Ala Gly His Thr Phe Pro His Glu Leu Ala Val Ala Arg Ile Asn
        275                 280                 285

Gly Val Phe Gly Ser Val Asp Ala Asn Gln Gly Asp Ser Leu Leu Gly
    290                 295                 300

Trp Asp Thr Asp Gln Phe Pro Thr Asp Val Lys Glu Ala Thr Leu Ser
305                 310                 315                 320

Met Leu Glu Ile Ile Lys Ala Gly Gly Phe Thr Asn Gly Gly Leu Asn
                325                 330                 335

Phe Asp Ala Lys Val Arg Arg Pro Ser Phe Thr Phe Glu Asp Ile Val
            340                 345                 350

Tyr Gly Tyr Ile Ser Gly Met Asp Thr Phe Ala Leu Gly Leu Ile Lys
        355                 360                 365

Ala Tyr Glu Val Ile Glu Asp Gly Arg Ile Asp Glu Phe Ile Glu Lys
    370                 375                 380

Arg Tyr Ala Ser Tyr Glu Ser Gly Ile Gly Lys Lys Ile Leu Asn Asn
385                 390                 395                 400

Glu Val Thr Leu Glu Glu Leu Glu Ala Tyr Thr Leu Glu Asn Lys Glu
                405                 410                 415

Arg Pro Met Glu Ser Gly Arg Gln Glu Tyr Leu Glu Thr Ile Leu Asn
            420                 425                 430

Gln Ile Leu Tyr Lys
        435

<210> SEQ ID NO 3
<211> LENGTH: 440
<212> TYPE: PRT
<213> ORGANISM: Mageeibacillus indolicus

<400> SEQUENCE: 3

Met Lys Phe Phe Glu Asn Val Pro Lys Val Lys Tyr Glu Gly Ser Lys
1               5                   10                  15

Ser Thr Asn Pro Phe Ala Phe Lys Tyr Tyr Asn Pro Glu Ala Val Ile
                20                  25                  30

Ala Gly Lys Lys Met Lys Asp His Leu Lys Phe Ala Met Ser Trp Trp
            35                  40                  45

His Thr Met Thr Ala Thr Gly Gln Asp Gln Phe Gly Ser Gly Thr Met
        50                  55                  60

Ser Arg Ile Tyr Asp Gly Gln Thr Glu Pro Leu Ala Leu Ala Lys Ala
65                  70                  75                  80

Arg Val Asp Ala Ala Phe Asp Phe Met Glu Lys Leu Asn Ile Glu Tyr
                85                  90                  95

Phe Cys Phe His Asp Ala Asp Leu Ala Pro Glu Gly Asn Ser Leu Gln
            100                 105                 110

Glu Arg Asn Glu Asn Leu Gln Glu Met Val Ser Tyr Leu Lys Gln Lys
        115                 120                 125

Met Ala Gly Thr Ser Ile Lys Leu Leu Trp Gly Thr Ser Asn Cys Phe
    130                 135                 140

Ser Asn Pro Arg Phe Met His Gly Ala Ala Thr Ser Cys Glu Ala Asp
```

```
            145                 150                 155                 160
        Val Phe Ala Trp Thr Ala Thr Gln Leu Lys Asn Ala Ile Asp Ala Thr
                        165                 170                 175

Ile Ala Leu Gly Gly Lys Gly Tyr Val Phe Trp Gly Gly Arg Glu Gly
                        180                 185                 190

Tyr Glu Thr Leu Leu Asn Thr Asp Val Gly Leu Glu Met Asp Asn Tyr
                        195                 200                 205

Ala Arg Met Leu Lys Met Ala Val Ala Tyr Ala Arg Ser Lys Gly Tyr
                        210                 215                 220

Thr Gly Asp Phe Tyr Ile Glu Pro Lys Pro Lys Glu Pro Thr Lys His
        225                 230                 235                 240

Gln Tyr Asp Phe Asp Val Ala Thr Cys Val Ala Phe Leu Glu Lys Tyr
                        245                 250                 255

Asp Leu Met Arg Asp Phe Lys Val Asn Ile Glu Ala Asn His Ala Thr
                        260                 265                 270

Leu Ala Gly His Thr Phe Gln His Glu Leu Arg Met Ala Arg Thr Phe
                        275                 280                 285

Gly Val Phe Gly Ser Val Asp Ala Asn Gln Gly Asp Ser Asn Leu Gly
                        290                 295                 300

Trp Asp Thr Asp Gln Phe Pro Gly Asn Ile Tyr Asp Thr Thr Leu Ala
        305                 310                 315                 320

Met Tyr Glu Ile Leu Lys Ala Gly Gly Phe Thr Asn Gly Gly Leu Asn
                        325                 330                 335

Phe Asp Ala Lys Val Arg Arg Pro Ser Phe Thr Pro Glu Asp Ile Ala
                        340                 345                 350

Tyr Ala Tyr Ile Leu Gly Met Asp Thr Phe Ala Leu Gly Leu Ile Lys
                        355                 360                 365

Ala Gln Gln Leu Ile Glu Asp Gly Arg Ile Asp Arg Phe Val Ala Glu
                        370                 375                 380

Lys Tyr Ala Ser Tyr Lys Ser Gly Ile Gly Ala Glu Ile Leu Ser Gly
        385                 390                 395                 400

Lys Thr Ser Leu Pro Glu Leu Glu Ala Tyr Ala Leu Lys Lys Gly Glu
                        405                 410                 415

Pro Lys Leu Tyr Ser Gly Arg Gln Glu Tyr Leu Glu Ser Val Val Asn
                        420                 425                 430

Asn Val Ile Phe Asn Gly Asn Leu
                        435                 440

<210> SEQ ID NO 4
<211> LENGTH: 441
<212> TYPE: PRT
<213> ORGANISM: Ruminococcus sp.

<400> SEQUENCE: 4

Met Ala Glu Phe Phe Ala Asn Ile Pro Lys Ile Lys Tyr Glu Gly Pro
        1               5                   10                  15

Gln Ser Thr Asn Pro Leu Ala Phe Lys Tyr Tyr Asn Pro Asp Glu Val
                        20                  25                  30

Ile Gly Gly Lys Thr Met Lys Glu Gln Leu Arg Phe Ala Leu Ser Trp
                        35                  40                  45

Trp His Thr Met Gly Gly Asp Gly Thr Asp Met Phe Gly Cys Gly Thr
                        50                  55                  60

Thr Asp Lys Thr Trp Gly Glu Ala Ser Pro Glu Ala Arg Ala Lys Ala
        65                  70                  75                  80
```

```
Lys Val Asp Ala Ala Phe Glu Ile Met Asp Lys Leu Ser Ile Asp Tyr
                85                  90                  95

Phe Cys Tyr His Asp Arg Asp Ile Ser Pro Glu Tyr Gly Ser Leu Lys
            100                 105                 110

Glu Thr Asn Glu Lys Phe Asp Glu Leu Ile Asp Tyr Ile Ala Glu Lys
        115                 120                 125

Met Lys Ala Asp Pro Ser Lys Lys Leu Leu Trp Gly Thr Ala Lys Cys
    130                 135                 140

Phe Asp His Pro Arg Tyr Met His Gly Ala Gly Thr Ser Pro Ser Ala
145                 150                 155                 160

Asp Val Phe Ala Tyr Ala Ala Ala Gln Ile Lys Lys Ala Ile Asp Ser
                165                 170                 175

Thr Ile Lys Leu Gly Gly Lys Gly Tyr Val Phe Trp Gly Gly Arg Glu
            180                 185                 190

Gly Tyr Glu Thr Leu Leu Asn Thr Asn Met Gly Leu Glu Leu Asp Asn
        195                 200                 205

Met Ala Arg Leu Met Lys Met Ala Val Glu Tyr Ala Arg Ser Lys Gly
    210                 215                 220

Tyr Asp Gly Asp Phe Tyr Ile Glu Pro Lys Pro Lys Glu Pro Thr Lys
225                 230                 235                 240

His Gln Tyr Asp Phe Asp Thr Ala Thr Val Ile Gly Phe Leu Arg Lys
                245                 250                 255

Tyr Gly Leu Asp Lys Asp Phe Lys Met Asn Ile Glu Ala Asn His Ala
            260                 265                 270

Thr Leu Ala Gln His Thr Phe Gln His Glu Leu Arg Val Ala Arg Asp
        275                 280                 285

Asn Gly Phe Phe Gly Ser Ile Asp Ala Asn Gln Gly Asp Pro Leu Leu
    290                 295                 300

Gly Trp Asp Thr Asp Gln Phe Pro Thr Asn Ala Tyr Asp Ala Thr Leu
305                 310                 315                 320

Cys Met Tyr Glu Val Ile Lys Ala Gly Gly Phe Thr Asn Gly Gly Leu
                325                 330                 335

Asn Phe Asp Ala Lys Ala Arg Arg Gly Ser Tyr Thr Leu Asp Asp Ile
            340                 345                 350

Phe Tyr Ser Tyr Ile Ala Gly Met Asp Thr Phe Ala Leu Gly Leu Arg
        355                 360                 365

Ala Ala Tyr Lys Leu Ile Glu Asp Gly Arg Val Asp Lys Phe Val Asp
    370                 375                 380

Asp Arg Tyr Ala Ser Trp Asn Thr Gly Ile Gly Lys Asp Ile Ile Asp
385                 390                 395                 400

Gly Lys Val Gly Phe Glu Glu Leu Glu Lys Tyr Ala Leu Glu Lys Gly
                405                 410                 415

Glu Val Thr Asp Ser Leu Thr Ser Gly Arg Gln Glu Tyr Leu Glu Ser
            420                 425                 430

Val Leu Asn Gln Ile Met Phe Thr Leu
        435                 440

<210> SEQ ID NO 5
<211> LENGTH: 438
<212> TYPE: PRT
<213> ORGANISM: Epulopiscium sp.

<400> SEQUENCE: 5

Met Val Asn Gly Leu Thr Asn Ile Pro Pro Val Lys Phe Glu Gly Arg
1               5                   10                  15
```

-continued

```
Asp Ser Lys Lys Ala Leu Ser Phe Lys Tyr Tyr Asn Pro Asp Glu Met
             20                  25                  30
Ile Gln Gly Lys Lys Met Lys Asp Tyr Leu Lys Phe Ala Met Ser Tyr
         35                  40                  45
Trp His Thr Leu Cys Gly Asp Gly Thr Asp Pro Phe Gly Ser Ser Thr
 50                  55                  60
Ile Asp Arg Asp Tyr Ser Gly Gln Thr Pro Met Glu Lys Ala Lys Thr
 65                  70                  75                  80
Lys Ala Asp Val Ala Phe Ala Leu Met Gln Ile Leu Gly Ile Glu Tyr
                 85                  90                  95
Phe Cys Phe His Asp Leu Asp Ile Ala Pro Thr Gly Asn Ser Leu Lys
             100                 105                 110
Glu Leu Lys Asn Asn Leu Ile Glu Ile Thr Asp Tyr Ile Lys Gly Leu
         115                 120                 125
Met Asp Lys Thr Gly Ile Lys Leu Leu Trp Gly Thr Ala Asn Cys Phe
130                 135                 140
Ser His Pro Arg Tyr Met Asn Gly Ala Gly Thr Ser Pro Gln Ala Asp
145                 150                 155                 160
Ile Phe Ala Cys Ala Ala Ala Gln Ile Lys Asn Ala Ile Asp Ala Thr
                 165                 170                 175
Ile Lys Leu Gly Gly Thr Gly Tyr Val Phe Trp Gly Gly Arg Glu Gly
             180                 185                 190
Tyr Glu Thr Leu Leu Asn Thr Asn Met Glu Ile Glu Leu Asp Asn Met
         195                 200                 205
Ala Lys Leu Met His Met Ala Val Asp Tyr Ala Arg Ser Lys Gly Phe
    210                 215                 220
Thr Gly Asp Phe Tyr Ile Glu Pro Lys Pro Lys Glu Pro Thr Lys His
225                 230                 235                 240
Gln Tyr Asp Phe Asp Val Ala Thr Val Val Gly Phe Leu Arg Lys Tyr
                 245                 250                 255
Gly Leu Asp Lys Asp Phe Lys Met Asn Ile Glu Ala Asn His Ala Thr
             260                 265                 270
Leu Ala Gly His Thr Phe Gln His Glu Leu Asn Val Ala Arg Val Asn
         275                 280                 285
Asn Val Phe Gly Ser Ile Asp Ala Asn Gln Gly Asp Leu Leu Leu Gly
    290                 295                 300
Trp Asp Thr Asp Gln Phe Pro Thr Asn Val Tyr Asp Thr Thr Leu Cys
305                 310                 315                 320
Met Leu Glu Val Ile Lys Ala Gly Gly Phe Thr Asn Gly Gly Leu Asn
                 325                 330                 335
Phe Asp Ala Lys Val Arg Arg Ala Ser Tyr Thr Met Glu Asp Ile Ile
             340                 345                 350
Leu Ala Tyr Ile Ser Gly Met Asp Thr Phe Ala Leu Gly Leu Lys Ile
         355                 360                 365
Ala Asn Lys Ile Ile Glu Asp Gly Arg Ile Asp Glu Phe Val Ser Arg
    370                 375                 380
Arg Tyr Ala Ser Tyr Lys Thr Gly Ile Gly Ala Asp Ile Ile Ala Gly
385                 390                 395                 400
Arg Thr Asn Leu Glu Glu Leu Glu Lys Tyr Ala Leu Glu Leu Pro Pro
                 405                 410                 415
Val Glu Pro His Pro Gly Lys Gln Glu Tyr Leu Glu Ala Val Phe Asn
             420                 425                 430
```

-continued

```
Asn Val Met Phe Thr Val
        435

<210> SEQ ID NO 6
<211> LENGTH: 437
<212> TYPE: PRT
<213> ORGANISM: Alkaliphilus metalliredigens

<400> SEQUENCE: 6

Met Arg Glu His Phe Leu Glu Ile Asn Lys Ile Lys Phe Glu Gly Gly
1               5                   10                  15

Asp Ser Thr Asn Pro Leu Ala Phe Lys Tyr Tyr Asp Ala Asn Arg Ile
            20                  25                  30

Val Ala Gly Lys Lys Met Lys Asp His Leu Arg Phe Ala Leu Ser Tyr
        35                  40                  45

Trp His Thr Leu Thr Gly Asn Gly Thr Asp Pro Phe Gly Gln Pro Thr
    50                  55                  60

Met Glu Arg Asp Tyr Asn Ser Leu Asp Gly Ile Glu Leu Ser Lys Ala
65                  70                  75                  80

Arg Val Asp Ala Ala Phe Glu Leu Met Thr Lys Leu Gly Ile Glu Phe
                85                  90                  95

Phe Cys Phe His Asp Leu Asp Ile Ala Pro Glu Gly Asn Ser Leu Gln
            100                 105                 110

Glu Lys Leu Asp Asn Leu Asp Thr Ile Leu Glu Arg Ile Glu Asp Lys
        115                 120                 125

Met Lys Glu Thr Gly Ile Lys Cys Leu Trp Gly Thr Thr Asn Ala Phe
    130                 135                 140

Ser His Pro Arg Phe Met His Gly Ala Ala Thr Ser Pro Asn Ala Asp
145                 150                 155                 160

Val Phe Ala Phe Ala Ala Ala Gln Val Lys Lys Ala Leu Glu Ile Thr
                165                 170                 175

His Arg Leu Arg Gly Glu Asn Tyr Val Phe Trp Gly Gly Arg Glu Gly
            180                 185                 190

Tyr Glu Thr Leu Leu Asn Thr Asp Ile Ala Leu Glu Asn Asp Asn Leu
        195                 200                 205

Ala Lys Phe Leu Lys Met Ala Lys Asp Tyr Ala Arg Asn Ile Gly Phe
    210                 215                 220

Glu Gly Gln Phe Leu Ile Glu Pro Lys Pro Lys Glu Pro Thr Lys His
225                 230                 235                 240

Gln Tyr Asp Phe Asp Thr Met Thr Val Leu Gly Phe Leu Arg Lys Tyr
                245                 250                 255

Asn Leu Ile Asp Asp Phe Lys Leu Asn Ile Glu Ala Asn His Ala Thr
            260                 265                 270

Leu Ala Gly His Thr Phe Gln His Glu Leu Ala Met Ala Arg Ile Asn
        275                 280                 285

Gly Val Leu Gly Ser Val Asp Ala Asn Gln Gly Asp Leu Leu Leu Gly
    290                 295                 300

Trp Asp Thr Asp Gln Phe Pro Thr Asn Ile Tyr Asp Ala Thr Leu Ser
305                 310                 315                 320

Met Tyr Glu Val Leu Lys Asn Gly Gly Ile Ala Pro Gly Gly Leu Asn
                325                 330                 335

Phe Asp Ala Lys Val Arg Arg Gly Ser Phe Lys Pro Asp Asp Leu Phe
            340                 345                 350

Ile Ala Tyr Ile Val Gly Met Asp Thr Phe Ala Lys Gly Leu Leu Val
        355                 360                 365
```

```
Ala Asp Lys Leu Leu Thr Asp Gly Val Leu Glu Asn Phe Val Thr Lys
        370                 375                 380

Arg Tyr Glu Ser Tyr Thr Ala Gly Ile Gly Lys Ile Ile Glu Asp
385                 390                 395                 400

Ala Thr Ser Phe Glu Glu Leu Ala Glu Tyr Ala Leu Lys His Asp Lys
                405                 410                 415

Ile Val Leu Glu Ser Gly Arg Gln Glu Met Leu Glu Asp Ile Val Asn
            420                 425                 430

Arg Tyr Ile Tyr Lys
            435

<210> SEQ ID NO 7
<211> LENGTH: 440
<212> TYPE: PRT
<213> ORGANISM: Eubacterium sp.

<400> SEQUENCE: 7

Met Tyr Phe Asn Asn Ile Glu Lys Ile Lys Phe Glu Gly Val Asn Ser
1               5                   10                  15

Lys Asn Pro Leu Ala Phe Lys Tyr Tyr Asp Ala Asp Arg Ile Ile Ala
                20                  25                  30

Gly Lys Lys Met Ser Glu His Leu Lys Phe Ala Met Ser Tyr Trp His
            35                  40                  45

Thr Met Cys Ala Asp Gly Thr Asp Met Phe Gly Arg Gly Thr Ile Asn
        50                  55                  60

Lys Ser Phe Gly Gly Lys Thr Ala Ile Glu Ile Tyr Glu His Lys Val
65                  70                  75                  80

Tyr Ala Ala Phe Glu Leu Met Glu Lys Leu Gly Met Gln Tyr Phe Cys
                85                  90                  95

Phe His Asp Arg Asp Ile Ala Pro Glu Gly Ala Thr Leu Lys Glu Thr
                100                 105                 110

Asn Glu Asn Leu Glu Arg Ile Val Pro Ile Ile Lys Ser Glu Met Lys
            115                 120                 125

Arg Thr Gly Ile Lys Leu Leu Trp Gly Thr Ala Asn Cys Phe Asn His
130                 135                 140

Pro Arg Tyr Met Cys Gly Ala Gly Thr Ala Pro Ser Ala Asp Val Phe
145                 150                 155                 160

Ala Tyr Ala Ala Ala Gln Ile Lys Lys Ala Ile Glu Ile Thr Val Glu
                165                 170                 175

Leu Gly Gly Gln Gly Tyr Val Phe Trp Gly Gly Arg Glu Gly Tyr Asp
            180                 185                 190

Thr Ile Leu Asn Thr Asp Met Ala Lys Glu Gln Asp Asn Met Ala Tyr
        195                 200                 205

Leu Met Arg Met Ala Val Asp Tyr Gly Arg Ser Ile Gly Phe Thr Gly
210                 215                 220

Asp Phe Tyr Ile Glu Pro Lys Pro Lys Glu Pro Thr Lys His Gln Tyr
225                 230                 235                 240

Asp Phe Asp Val Ser Thr Val Leu Ala Phe Leu Arg Lys Tyr Asp Leu
                245                 250                 255

Asp Lys Asp Phe Lys Met Asn Ile Glu Ala Asn His Ala Thr Leu Ala
            260                 265                 270

Gly His Thr Phe Gln His Glu Leu Arg Val Ala Arg Asp Asn Gly Val
        275                 280                 285

Phe Gly Ser Ile Asp Ala Asn Gln Gly Asp Met Leu Leu Gly Trp Asp
```

```
            290                 295                 300

Thr Asp Gln Phe Pro Thr Asp Leu Tyr Ser Thr Thr Met Cys Met Tyr
305                 310                 315                 320

Glu Val Leu Lys Gln Gly Gly Phe Thr Asn Gly Gly Leu Asn Phe Asp
                325                 330                 335

Ala Lys Ala Arg Arg Ala Ser Asn Thr Tyr Glu Asp Val Phe Leu Ser
                340                 345                 350

Tyr Ile Ala Gly Met Asp Ala Phe Ala Tyr Gly Leu Ile Val Ala Asp
            355                 360                 365

Lys Ile Ile Ser Asp Gly Val Met Asp Lys Phe Val Glu Asn Arg Tyr
        370                 375                 380

Ser Ser Tyr Thr Glu Gly Ile Gly Lys Lys Ile Ala Asp Lys Gln Thr
385                 390                 395                 400

Ser Leu Ala Glu Leu Glu Gln Tyr Thr Leu Thr Asn Gly Glu Pro Thr
                405                 410                 415

Ala Glu Ser Gly Lys Gln Glu Tyr Leu Glu Ala Leu Val Asn Gln Tyr
                420                 425                 430

Ile Ile Ser Ala Gly Arg Glu Leu
            435                 440

<210> SEQ ID NO 8
<211> LENGTH: 439
<212> TYPE: PRT
<213> ORGANISM: Clostridium saccharoperbutylacetonicum

<400> SEQUENCE: 8

Met Lys Glu Tyr Phe Gly Asn Val Ser Lys Ile Asn Tyr Glu Gly Pro
1               5                   10                  15

Gly Ser Lys Asn Pro Tyr Ser Phe Lys Tyr Tyr Asn Pro Asp Glu Val
                20                  25                  30

Ile Gly Gly Lys Thr Met Lys Glu His Leu Arg Phe Ser Leu Ser Tyr
            35                  40                  45

Trp His Thr Leu Thr Ala Asn Gly Ala Asp Pro Phe Gly Ala Gly Thr
    50                  55                  60

Met Leu Arg Pro Trp Asp Asp Ile Thr Asn Glu Met Asp Leu Ala Lys
65                  70                  75                  80

Ala Arg Met Glu Ala Ala Phe Glu Leu Met Asp Lys Leu Asn Ile Glu
                85                  90                  95

Tyr Phe Cys Phe His Asp Arg Asp Ile Ala Pro Glu Gly Lys Thr Leu
            100                 105                 110

Gln Glu Thr Asn Glu Asn Leu Asp Glu Ile Val Ala Tyr Cys Lys Glu
        115                 120                 125

Leu Met Lys Lys Tyr Asn Lys Lys Leu Leu Trp Gly Thr Ala Asn Cys
130                 135                 140

Phe Thr Asn Pro Arg Tyr Val His Gly Ala Gly Thr Ser Cys Asn Ala
145                 150                 155                 160

Asp Val Phe Ala Tyr Ala Ala Ala Gln Ile Lys Lys Ala Leu Glu Val
                165                 170                 175

Thr Lys Glu Leu Gly Gly Glu Asn Tyr Val Phe Trp Gly Gly Arg Glu
            180                 185                 190

Gly Tyr Glu Thr Leu Leu Asn Thr Asp Met Gly Leu Glu Leu Asp Asn
        195                 200                 205

Phe Ala Arg Leu Leu Gln Met Ala Val Asp Tyr Ala Lys Glu Ile Gly
210                 215                 220
```

Phe Thr Gly Gln Phe Leu Ile Glu Pro Lys Pro Lys Glu Pro Thr Lys
225                 230                 235                 240

His Gln Tyr Asp Phe Asp Thr Ala Thr Val Leu Gly Phe Leu Lys Lys
            245                 250                 255

Tyr Asn Leu Asp Lys Tyr Phe Lys Val Asn Ile Glu Ala Asn His Ala
        260                 265                 270

Thr Leu Ala Gln His Thr Phe Gln His Glu Leu Asn Phe Ala Arg Ile
    275                 280                 285

Asn Asn Phe Leu Gly Ser Ile Asp Ala Asn Gln Gly Asp Pro Met Leu
290                 295                 300

Gly Trp Asp Thr Asp Gln Phe Pro Thr Asn Ile Tyr Asp Ala Thr Leu
305                 310                 315                 320

Ala Met Tyr Glu Ile Leu Lys Asn Gly Gly Leu Ala Pro Gly Gly Val
            325                 330                 335

Asn Phe Asp Ala Lys Val Arg Arg Ala Ser Phe Glu Lys Glu Asp Leu
        340                 345                 350

Phe Leu Ala Tyr Ile Ala Gly Met Asp Thr Phe Ala Lys Gly Leu Lys
    355                 360                 365

Val Ala His Lys Leu Leu Glu Asn Gly Glu Leu Glu Asn Phe Ile Lys
370                 375                 380

Asn Lys Tyr Ala Ser Phe Ser Glu Gly Ile Gly Lys Glu Ile Val Glu
385                 390                 395                 400

Gly Lys Val Gly Leu Lys Glu Leu Glu Ala Tyr Ala Leu Lys Asn Asn
            405                 410                 415

Glu Ile Thr Asn Lys Ser Gly Arg Gln Glu Leu Leu Ala Ile Val
        420                 425                 430

Asn Gln Tyr Ile Phe Glu Asp
            435

<210> SEQ ID NO 9
<211> LENGTH: 436
<212> TYPE: PRT
<213> ORGANISM: Fusobacterium mortiferum

<400> SEQUENCE: 9

Met Glu Phe Phe Lys Gly Ile Asp Lys Val Lys Tyr Glu Gly Val Lys
1               5                   10                  15

Thr Asn Asn Leu Leu Ala Phe Ala His Tyr Asn Pro Glu Glu Val Ile
            20                  25                  30

Leu Gly Lys Lys Met Lys Asp His Leu Lys Phe Ala Met Ser Tyr Trp
        35                  40                  45

His Thr Leu Thr Gly Glu Gly Thr Asp Pro Phe Gly Asn Ala Thr Met
    50                  55                  60

Asp Arg Glu Trp Asn Glu Tyr Thr Pro Met Glu Lys Ala Lys Ala Arg
65                  70                  75                  80

Val Lys Ala Gly Phe Glu Phe Met Glu Lys Leu Gly Leu Glu Tyr Phe
            85                  90                  95

Cys Phe His Asp Lys Asp Ile Ala Pro Glu Ala Glu Thr Leu Glu Glu
        100                 105                 110

Tyr His Arg Asn Leu Asp Glu Ile Val Asp Leu Ile Glu Glu Glu Met
    115                 120                 125

Lys Arg Thr Gly Ile Lys Leu Leu Trp Gly Thr Ser Asn Met Phe Ser
130                 135                 140

His Pro Arg Phe Met His Gly Ala Ala Thr Ser Cys Asn Ala Asp Val
145                 150                 155                 160

```
Phe Ala Tyr Ala Ala Ala Gln Thr Lys Lys Ala Leu Glu Ile Thr Lys
                165                 170                 175

Arg Leu Asn Gly Thr Gly Tyr Val Phe Trp Gly Gly Arg Glu Gly Tyr
            180                 185                 190

Glu Thr Leu Leu Asn Thr Asp Ile Gly Leu Glu Leu Asp Asn Leu Ala
        195                 200                 205

Arg Phe Leu Gln Met Ala Val Asp Tyr Ala Lys Lys Ile Gly Phe Glu
    210                 215                 220

Gly Gln Phe Phe Ile Glu Pro Lys Pro Lys Glu Pro Thr Lys His Gln
225                 230                 235                 240

Tyr Asp Phe Asp Thr Thr Thr Val Leu Glu Phe Leu Arg Lys Tyr Asn
                245                 250                 255

Leu Asp Lys Tyr Phe Lys Met Asn Ile Glu Ala Asn His Ala Thr Leu
            260                 265                 270

Ala Gly His Thr Phe Gln His Glu Leu Cys Thr Ala Arg Ile Asn Gly
        275                 280                 285

Val Phe Gly Ser Ile Asp Ala Asn Gln Gly Asp Met Leu Leu Gly Trp
    290                 295                 300

Asp Thr Asp Gln Phe Pro Thr Asn Val Tyr Asp Ala Val Leu Ala Met
305                 310                 315                 320

Tyr Glu Thr Leu Leu Ala Gly Phe Lys Glu Gly Leu Asn Phe
                325                 330                 335

Asp Ala Lys Val Arg Arg Gly Ser Phe Glu Pro Lys Asp Leu Phe Tyr
            340                 345                 350

Ala Tyr Ile Ser Gly Met Asp Thr Phe Ala Lys Gly Leu Lys Val Ala
        355                 360                 365

Ala Lys Leu Ile Glu Asp Gly Thr Phe Glu Lys Ile Lys Val Glu Arg
    370                 375                 380

Tyr Ser Ser Tyr Thr Thr Gly Ile Gly Lys Gln Ile Val Asn Gly Glu
385                 390                 395                 400

Val Gly Phe Glu Glu Leu Ser Lys Tyr Ala Leu Thr Asn Gly Val Lys
                405                 410                 415

Lys Asn Ser Ser Gly Arg Gln Glu Met Leu Glu Asn Ile Leu Asn Arg
            420                 425                 430

Tyr Ile Tyr Glu
        435

<210> SEQ ID NO 10
<211> LENGTH: 439
<212> TYPE: PRT
<213> ORGANISM: Clostridium cellulosi

<400> SEQUENCE: 10

Met Lys Glu Tyr Phe Ser Asn Ile Pro Lys Val Arg Tyr Glu Gly Pro
1               5                   10                  15

Asp Ser Lys Asn Pro Phe Ala Phe Lys Phe Tyr Asn Pro Glu Glu Lys
            20                  25                  30

Ile Ala Gly Lys Thr Met Arg Glu Gln Leu Lys Phe Ser Leu Ala Tyr
        35                  40                  45

Trp His Thr Leu Asp Ala Glu Gly Thr Asp Met Phe Gly Arg Ala Thr
    50                  55                  60

Met Asp Lys Ser Phe Gly Glu Thr Asp Pro Met Ala Ile Tyr Lys Asn
65                  70                  75                  80

Lys Ala Tyr Ala Ala Phe Glu Leu Met Asp Lys Leu Asp Ile Asp Tyr
```

```
                    85                  90                  95
Phe Cys Phe His Asp Arg Asp Ile Ala Pro Glu Gly Pro Thr Leu Ser
            100                 105                 110

Glu Thr Asn Lys Asn Leu Asp Glu Ile Val Ser Leu Leu Lys Lys Leu
            115                 120                 125

Met Ala Glu His Asn Lys Lys Leu Leu Trp Gly Thr Ala Asn Thr Phe
        130                 135                 140

Ser His Pro Arg Tyr Val His Gly Ala Gly Thr Ser Cys Asn Ala Ser
145                 150                 155                 160

Val Phe Ala Phe Ala Ala Gln Ile Lys Lys Ala Ile Glu Ile Thr
                165                 170                 175

Lys Glu Leu Asp Gly Cys Gly Tyr Val Phe Trp Gly Arg Glu Gly
            180                 185                 190

Tyr Glu Thr Leu Leu Asn Thr Asp Met Glu Leu Glu Leu Asp Asn Met
                195                 200                 205

Ala Arg Leu Leu Lys Met Ala Val Asp Tyr Ala Arg Ser Ile Gly Phe
        210                 215                 220

Lys Gly Glu Phe Phe Ile Glu Pro Lys Pro Lys Glu Pro Thr Lys His
225                 230                 235                 240

Gln Tyr Asp Tyr Asp Val Ser Thr Val Leu Ala Phe Leu Arg Lys Tyr
                245                 250                 255

Gly Leu Asp Lys Val Phe Lys Val Asn Ile Glu Ala Asn His Ala Thr
            260                 265                 270

Leu Ala Gln His Thr Phe Gln His Glu Leu Arg Val Ala Arg Ile Asn
        275                 280                 285

Gly Val Leu Gly Ser Val Asp Ala Asn Gln Gly Asp Val Met Leu Gly
        290                 295                 300

Trp Asp Thr Asp Gln Phe Pro Thr Asn Val Tyr Asp Thr Ala Leu Ala
305                 310                 315                 320

Met Tyr Glu Ile Leu Lys Asn Gly Gly Leu Pro Ser Gly Leu Asn
                325                 330                 335

Phe Asp Ser Lys Asn Arg Arg Gly Ser Phe Glu Pro Glu Asp Ile Phe
            340                 345                 350

His Gly Phe Ile Ala Gly Met Asp Ala Phe Ala Leu Gly Leu Arg Ile
        355                 360                 365

Ala Asp Arg Ile Ile Arg Asp Gly Arg Leu Glu Gln Phe Val Lys Asp
        370                 375                 380

Arg Tyr Lys Ser Tyr Gln Ser Gly Ile Gly Ala Asp Ile Val Ser Gly
385                 390                 395                 400

Arg Ala Lys Ile Glu Asp Leu Glu Lys Tyr Ala Leu Lys Leu Gly Glu
                405                 410                 415

Val Asn Ala Ile Gly Ser Gly Arg Gln Glu Tyr Leu Glu Asp Ile Leu
            420                 425                 430

Asn Ser Ile Met Phe Gly Lys
            435

<210> SEQ ID NO 11
<211> LENGTH: 440
<212> TYPE: PRT
<213> ORGANISM: Cellulosilyticum lentocellum

<400> SEQUENCE: 11

Met Ala Glu Phe Phe Lys Gly Ile Gly Val Ile Pro Phe Glu Gly Ala
1               5                   10                  15
```

Asp Ser Val Asn Pro Leu Ala Phe Lys His Tyr Asn Lys Asp Glu Lys
             20                  25                  30

Val Gly Asp Lys Thr Met Ala Glu His Leu Arg Phe Ala Met Ser Tyr
         35                  40                  45

Trp His Thr Leu Cys Ala Glu Gly Gly Asp Pro Phe Gly Ser Thr Thr
     50                  55                  60

Ala Ala Arg Pro Trp Asn Gln Ile Ala Asn Pro Ile Glu Met Ala Lys
 65                  70                  75                  80

Ala Lys Val Asp Ala Gly Phe Glu Phe Met Gln Lys Leu Gly Ile Glu
                 85                  90                  95

Tyr Phe Cys Phe His Asp Arg Asp Ile Ala Pro Glu Gly Lys Asp Leu
             100                 105                 110

Ala Glu Thr Asn Gln Ile Leu Asp Glu Val Val Ala Tyr Ile Lys Val
         115                 120                 125

Lys Met Gln Glu Thr Gly Ile Lys Leu Leu Trp Gly Thr Ala Asn Cys
    130                 135                 140

Phe Asn Asn Lys Arg Phe Met His Gly Ala Gly Thr Thr Cys Asn Ala
145                 150                 155                 160

Glu Val Phe Ala Tyr Ala Ala Ala Gln Ile Lys Lys Ala Ile Glu Val
                165                 170                 175

Thr Lys Glu Leu Gly Gly Glu Asn Tyr Val Phe Trp Gly Gly Arg Glu
            180                 185                 190

Gly Tyr Glu Thr Leu Leu Asn Thr Asp Thr Gly Leu Glu Leu Asp Asn
        195                 200                 205

Phe Ala Arg Leu Leu Gln Met Ala Val Asp Tyr Ala Lys Glu Ile Gly
210                 215                 220

Phe Thr Gly Gln Phe Leu Ile Glu Pro Lys Pro Lys Glu Pro Thr Lys
225                 230                 235                 240

His Gln Tyr Asp Phe Asp Thr Ala Thr Val Leu Ala Phe Leu Arg Lys
                245                 250                 255

Tyr Asn Leu Asp Thr Tyr Phe Lys Met Asn Ile Glu Ala Asn His Ala
            260                 265                 270

Thr Leu Ala Gly His Thr Phe Gln His Glu Leu Asn Met Ser Arg Ile
        275                 280                 285

Asn Asn Val Leu Gly Ser Ile Asp Ala Asn Gln Gly Asp Leu Met Leu
290                 295                 300

Gly Trp Asp Thr Asp Gln Phe Pro Thr Asn Ile Tyr Asp Ala Thr Met
305                 310                 315                 320

Ala Met Tyr Glu Val Leu Lys Ala Gly Gly Ile Ala Pro Gly Gly Phe
                325                 330                 335

Asn Phe Asp Ser Lys Val Arg Arg Gly Ser Phe Glu Glu Ala Asp Leu
            340                 345                 350

Phe Ile Ala Tyr Ile Ala Gly Met Asp Thr Phe Ala Lys Gly Leu Lys
        355                 360                 365

Val Ala Tyr Asn Leu Leu Lys Asp Gly Val Leu Glu Asp Phe Val Ala
370                 375                 380

Asp Arg Tyr Ala Ser Phe Asn Glu Gly Ile Gly Lys Asp Ile Val Ser
385                 390                 395                 400

Gly Asn Val Gly Phe Lys Glu Leu Glu Ala Tyr Ala Leu Lys Gln Gln
                405                 410                 415

Pro Ile Val Asn Lys Ser Gly Arg Gln Glu Trp Leu Glu Thr Val Val
            420                 425                 430

Asn Gln Tyr Ile Tyr Asn Asn Lys

<210> SEQ ID NO 12
<211> LENGTH: 445
<212> TYPE: PRT
<213> ORGANISM: Peptoclostridium difficile

<400> SEQUENCE: 12

```
Met Ser Glu Ile Phe Lys Gly Ile Gly Gln Ile Lys Phe Glu Gly Val
1               5                   10                  15

Lys Ser Asp Asn Glu Leu Ala Phe Arg Tyr Tyr Asn Pro Glu Gln Val
            20                  25                  30

Val Gly Asn Lys Thr Met Lys Glu His Leu Arg Phe Ala Met Ser Tyr
        35                  40                  45

Trp His Thr Leu Cys Gly Glu Gly Asn Asp Pro Phe Gly Val Gly Thr
50                  55                  60

Val Glu Arg Pro Trp Asn Asn Ile Thr Asp Pro Ile Glu Ile Ala Lys
65                  70                  75                  80

Ile Lys Val Asp Ala Gly Phe Glu Phe Met Ser Lys Met Gly Ile Glu
                85                  90                  95

Tyr Phe Cys Phe His Asp Arg Asp Ile Ala Pro Glu Gly Arg Asp Leu
            100                 105                 110

Glu Glu Thr Asn Lys Ile Leu Asp Glu Ile Val Glu Tyr Ile Lys Val
        115                 120                 125

Asn Met Glu Lys Thr Gly Ile Lys Leu Leu Trp Gly Thr Ala Asn Met
130                 135                 140

Phe Gly Asn Pro Arg Phe Val His Gly Ala Ser Thr Thr Cys Asn Ala
145                 150                 155                 160

Asp Val Tyr Ala Tyr Ala Ala Ala Gln Val Lys Lys Ala Met Glu Ile
                165                 170                 175

Thr Lys Tyr Leu Gly Gly Glu Asn Phe Val Phe Trp Gly Gly Arg Glu
            180                 185                 190

Gly Tyr Glu Thr Leu Leu Asn Thr Asn Thr Glu Leu Glu Met Asp Asn
        195                 200                 205

Phe Ala Arg Phe Leu Gln Met Ala Val Asp Tyr Ala Lys Glu Ile Gly
210                 215                 220

Phe Thr Gly Gln Phe Leu Ile Glu Pro Lys Pro Lys Glu Pro Thr Lys
225                 230                 235                 240

His Gln Tyr Asp Phe Asp Thr Ala Thr Val Leu Gly Phe Leu Arg Lys
                245                 250                 255

Tyr Asn Leu Asp Lys Tyr Phe Lys Met Asn Ile Glu Ala Asn His Ala
            260                 265                 270

Thr Leu Ala Gly His Thr Phe Gln His Glu Leu Asn Ile Ala Arg Ile
        275                 280                 285

Asn Asn Val Leu Gly Ser Ile Asp Ala Asn Gln Gly Asp Leu Leu Leu
290                 295                 300

Gly Trp Asp Thr Asp Gln Phe Pro Thr Asn Ile Tyr Asp Ala Thr Leu
305                 310                 315                 320

Ala Met Tyr Glu Val Leu Lys Gln Gly Gly Ile Ala Pro Gly Gly Phe
                325                 330                 335

Asn Phe Asp Ser Lys Val Arg Arg Ala Ser Phe Glu Val Glu Asp Leu
            340                 345                 350

Phe Leu Ala Tyr Ile Ala Gly Met Asp Thr Phe Ala Lys Gly Leu Leu
        355                 360                 365
```

```
Ile Ala His Lys Leu Leu Glu Asp Glu Val Phe Glu Asn Phe Thr Lys
            370                 375                 380
Glu Arg Tyr Ala Ser Phe Ser Glu Gly Ile Gly Lys Asp Ile Val Glu
385                 390                 395                 400
Gly Lys Val Gly Phe Lys Glu Leu Glu Ser Tyr Ala Leu Gln Met Pro
                405                 410                 415
Val Ile Lys Asn Lys Ser Gly Arg Gln Glu Met Leu Glu Ser Ile Leu
            420                 425                 430
Asn Arg Tyr Ile Tyr Glu Val Asp Thr Ile Ser Asn Lys
            435                 440                 445

<210> SEQ ID NO 13
<211> LENGTH: 454
<212> TYPE: PRT
<213> ORGANISM: (Pepto)clostridium difficile NAP08

<400> SEQUENCE: 13

Met Cys Lys Ile Leu Gly Gly His Glu Met Asn Glu Ile Phe Lys Gly
1               5                   10                  15
Ile Gly Gln Ile Lys Phe Glu Gly Val Lys Ser Asn Asn Glu Leu Ala
            20                  25                  30
Phe Arg Tyr Tyr Asn Pro Glu Gln Val Val Gly Asn Lys Thr Met Lys
        35                  40                  45
Glu His Leu Arg Phe Ala Met Ser Tyr Trp His Thr Leu Cys Gly Glu
    50                  55                  60
Gly Asn Asp Pro Phe Gly Val Gly Thr Val Arg Pro Trp Asn Asn
65                  70                  75                  80
Ile Thr Asp Pro Ile Glu Ile Ala Lys Ile Lys Val Asp Ala Gly Phe
                85                  90                  95
Glu Phe Met Ser Lys Met Gly Ile Glu Tyr Phe Cys Phe His Asp Arg
            100                 105                 110
Asp Ile Ala Pro Glu Gly Arg Asp Leu Glu Glu Thr Asn Lys Ile Leu
        115                 120                 125
Asp Glu Ile Val Glu Tyr Ile Lys Ala Asn Met Glu Lys Thr Gly Ile
    130                 135                 140
Lys Leu Leu Trp Gly Thr Ala Asn Met Phe Gly Asn Pro Arg Phe Val
145                 150                 155                 160
His Gly Ala Ser Thr Thr Cys Asn Ala Asp Val Tyr Ala Tyr Ala Ala
                165                 170                 175
Ala Gln Val Lys Lys Ala Met Glu Ile Thr Lys Tyr Leu Gly Gly Glu
            180                 185                 190
Asn Phe Val Phe Trp Gly Gly Arg Glu Gly Tyr Glu Thr Leu Leu Asn
        195                 200                 205
Thr Asn Thr Glu Leu Glu Met Asp Asn Phe Ala Arg Phe Leu Gln Met
    210                 215                 220
Ala Val Asp Tyr Ala Lys Glu Ile Gly Phe Thr Gly Gln Phe Leu Ile
225                 230                 235                 240
Glu Pro Lys Pro Lys Glu Pro Thr Lys His Gln Tyr Asp Phe Asp Thr
                245                 250                 255
Ala Thr Val Leu Gly Phe Leu Arg Lys Tyr Asn Leu Asp Lys Tyr Phe
            260                 265                 270
Lys Val Asn Ile Glu Ala Asn His Ala Thr Leu Ala Gly His Thr Phe
        275                 280                 285
Gln His Glu Leu Asn Ile Ala Arg Ile Asn Asn Val Leu Gly Ser Ile
    290                 295                 300
```

```
Asp Ala Asn Gln Gly Asp Leu Leu Leu Gly Trp Asp Thr Asp Gln Phe
305                 310                 315                 320

Pro Thr Asn Ile Tyr Asp Ala Thr Leu Ala Met Tyr Glu Val Leu Lys
            325                 330                 335

Gln Gly Gly Ile Ala Pro Gly Gly Phe Asn Phe Asp Ser Lys Val Arg
        340                 345                 350

Arg Ala Ser Phe Glu Val Glu Asp Leu Phe Leu Ala Tyr Ile Ala Gly
            355                 360                 365

Met Asp Thr Phe Ala Lys Gly Leu Leu Ile Ala His Lys Leu Leu Glu
    370                 375                 380

Asp Glu Val Phe Glu Asn Phe Thr Lys Glu Arg Tyr Ala Ser Phe Ser
385                 390                 395                 400

Glu Gly Ile Gly Lys Asp Ile Val Gly Lys Val Gly Phe Lys Glu
                405                 410                 415

Leu Glu Ser Tyr Ala Leu Gln Met Pro Val Ile Lys Asn Lys Ser Gly
            420                 425                 430

Arg Gln Glu Met Leu Glu Ala Ile Leu Asn Arg Tyr Ile Tyr Glu Val
            435                 440                 445

Asp Thr Ile Ser Asn Lys
    450

<210> SEQ ID NO 14
<211> LENGTH: 438
<212> TYPE: PRT
<213> ORGANISM: Caldicellulosiruptor acetigenus

<400> SEQUENCE: 14

Met Lys Tyr Phe Lys Asp Ile Pro Glu Val Lys Tyr Glu Gly Pro Gln
1               5                   10                  15

Ser Asp Asn Pro Phe Ala Phe Lys Tyr Tyr Asn Pro Asp Glu Val Ile
            20                  25                  30

Asp Gly Lys Pro Leu Lys Asp His Leu Arg Phe Ala Ile Ala Tyr Trp
        35                  40                  45

His Thr Phe Cys Ala Thr Gly Ser Asp Pro Phe Gly Gln Pro Thr Ile
    50                  55                  60

Asn Arg Pro Trp Asp Lys Phe Ser Asn Pro Met Asp Asn Ala Lys Ala
65                  70                  75                  80

Arg Val Glu Ala Ala Phe Glu Phe Phe Glu Lys Leu Asn Val Pro Phe
                85                  90                  95

Phe Cys Phe His Asp Arg Asp Ile Ala Pro Glu Gly Glu Asn Leu Arg
            100                 105                 110

Glu Thr Asn Lys Asn Leu Asp Glu Ile Val Ser Met Ile Lys Glu Tyr
        115                 120                 125

Leu Lys Thr Ser Lys Thr Lys Val Leu Trp Gly Thr Ala Asn Leu Phe
130                 135                 140

Ser His Pro Arg Tyr Val His Gly Ala Ala Thr Ser Cys Asn Ala Asp
145                 150                 155                 160

Val Phe Ala Tyr Ala Ala Ala Gln Val Lys Lys Ala Leu Glu Val Thr
                165                 170                 175

Lys Glu Leu Gly Gly Glu Asn Tyr Val Phe Trp Gly Gly Arg Glu Gly
            180                 185                 190

Tyr Glu Thr Leu Leu Asn Thr Asp Met Glu Leu Glu Leu Asp Asn Leu
        195                 200                 205

Ala Arg Phe Leu His Met Ala Val Asp Tyr Ala Lys Glu Ile Gly Phe
```

```
               210                 215                 220
Asp Gly Gln Phe Leu Ile Glu Pro Lys Pro Lys Glu Pro Thr Lys His
225                 230                 235                 240

Gln Tyr Asp Phe Asp Ala Ala His Val Tyr Gly Phe Leu Lys Lys Tyr
                245                 250                 255

Asp Leu Asp Lys Tyr Phe Lys Leu Asn Ile Glu Val Asn His Ala Thr
            260                 265                 270

Leu Ala Gly His Asp Phe His His Glu Leu Arg Phe Ala Arg Ile Asn
            275                 280                 285

Asn Met Leu Gly Ser Ile Asp Ala Asn Met Gly Asp Leu Leu Leu Gly
        290                 295                 300

Trp Asp Thr Asp Gln Phe Pro Thr Asp Val Arg Leu Thr Thr Leu Ala
305                 310                 315                 320

Met Tyr Glu Val Ile Lys Met Gly Gly Phe Asp Lys Gly Gly Leu Asn
                325                 330                 335

Phe Asp Ala Lys Val Arg Arg Gly Ser Phe Glu Leu Glu Asp Leu Val
            340                 345                 350

Ile Gly His Ile Ala Gly Met Asp Ala Phe Lys Gly Phe Lys Ile
            355                 360                 365

Ala Tyr Lys Leu Val Lys Asp Gly Val Phe Asp Lys Phe Ile Glu Glu
370                 375                 380

Arg Tyr Arg Ser Tyr Lys Glu Gly Ile Gly Ala Lys Ile Val Ser Gly
385                 390                 395                 400

Gln Ala Asp Phe Lys Thr Leu Glu Glu Tyr Ala Leu Asn Leu Ser Lys
                405                 410                 415

Ile Glu Asn Lys Ser Gly Lys Gln Glu Leu Leu Glu Met Ile Leu Asn
            420                 425                 430

Lys Tyr Met Phe Ser Glu
            435

<210> SEQ ID NO 15
<211> LENGTH: 436
<212> TYPE: PRT
<213> ORGANISM: Agrobacterium tumefaciens

<400> SEQUENCE: 15

Met Ser Thr Gly Phe Phe Gly Asp Ile Ala Lys Val Lys Tyr Glu Gly
1               5                   10                  15

Pro Asp Ser Thr Asn Pro Leu Ala Phe Arg His Tyr Asn Lys Asp Glu
                20                  25                  30

Val Val Leu Gly Lys Arg Met Glu Asp His Leu Arg Phe Ala Val Ala
            35                  40                  45

Tyr Trp His Thr Phe Thr Trp Pro Gly Gly Asp Pro Phe Gly Gly Gln
        50                  55                  60

Thr Phe Leu Arg Pro Trp Phe Asn Glu Thr Met Glu Ala Ala Lys Leu
65                  70                  75                  80

Lys Ala Asp Val Ala Phe Glu Phe Phe Thr Leu Leu Gly Ser Pro Tyr
                85                  90                  95

Tyr Cys Phe His Asp Ala Asp Val Arg Pro Glu Gly Lys Asn Phe Ala
            100                 105                 110

Glu Asn Thr Lys Asn Leu Asn Glu Ile Val Asp Tyr Phe Ala Gln Lys
        115                 120                 125

Gln Ala Asp Thr Gly Val Lys Leu Leu Trp Gly Thr Ala Asn Leu Phe
    130                 135                 140
```

Ser Asn Arg Arg Phe Met Ser Gly Ala Ala Thr Asn Pro Asp Pro Asp
145 150 155 160

Val Phe Ala Phe Ser Ala Ala Thr Val Lys Thr Cys Met Asp Ala Thr
165 170 175

His Lys Leu Gly Gly Glu Asn Tyr Val Leu Trp Gly Gly Arg Glu Gly
180 185 190

Tyr Glu Thr Leu Leu Asn Thr Asp Leu Lys Arg Glu Leu Asp Gln Met
195 200 205

Gly Arg Phe Leu Asn Leu Val Val Glu Tyr Lys His Lys Ile Gly Phe
210 215 220

Lys Gly Ala Ile Leu Ile Glu Pro Lys Pro Gln Glu Pro Thr Lys His
225 230 235 240

Gln Tyr Asp Tyr Asp Val Ala Thr Val Tyr Gly Phe Leu Lys Lys Asn
245 250 255

Gly Leu Glu Asn Glu Val Lys Leu Asn Ile Glu Gln Gly His Ala Ile
260 265 270

Leu Ala Gly His Ser Phe Glu His Glu Leu Ala Leu Ala Asn Ala Leu
275 280 285

Gly Ile Phe Gly Ser Ile Asp Met Asn Arg Asn Asp Tyr Gln Ser Gly
290 295 300

Trp Asp Thr Asp Gln Phe Pro Asn Asn Val Pro Glu Met Ser Leu Ala
305 310 315 320

Tyr Tyr Gln Val Leu Ala Gly Gly Gly Phe Lys Ser Gly Gly Thr Asn
325 330 335

Phe Asp Ser Lys Leu Arg Arg Gln Ser Leu Asp Pro Ala Asp Leu Leu
340 345 350

Ile Gly His Ile Gly Gly Met Asp Cys Cys Ala Arg Gly Leu Lys Ala
355 360 365

Ala Ala Lys Met Ile Glu Asp Lys Ala Leu Ser Gln Pro Leu Ala Asp
370 375 380

Arg Tyr Ala Gly Trp Asp Ser Ala Glu Gly Gln Lys Leu Leu Arg Gly
385 390 395 400

Glu Tyr Ser Leu Asp Gln Ile Ala Gln Trp Val Glu Ala Lys Asp Ile
405 410 415

Asn Pro Gln Pro Lys Ser Gly Lys Gln Glu Leu Leu Glu Asn Ile Val
420 425 430

Asn Arg Tyr Val
435

<210> SEQ ID NO 16
<211> LENGTH: 440
<212> TYPE: PRT
<213> ORGANISM: Burkholderia cenocepacia

<400> SEQUENCE: 16

Met Ser Tyr Phe Glu His Ile Pro Ala Ile Arg Tyr Glu Gly Pro Gln
1 5 10 15

Ser Asp Asn Pro Leu Ala Tyr His His Tyr Asp Pro Asp Lys Arg Val
20 25 30

Leu Gly Lys Thr Leu Ala Glu His Leu Arg Ile Ala Val Cys Tyr Trp
35 40 45

His Thr Phe Val Trp Pro Gly His Asp Ile Phe Gly Gln Ala Ala Phe
50 55 60

Arg Arg Pro Trp Gln Gln Pro Gly Asp Ala Leu Glu Arg Ala Arg Met
65 70 75 80

Lys Ala Asp Ala Ala Phe Glu Phe Phe Thr Lys Leu Gly Thr Pro Phe
            85                  90                  95

Tyr Thr Phe His Asp Thr Asp Val Ala Pro Glu Gly Asp Ser Leu Arg
            100                 105                 110

Glu Tyr Ala Ala Asn Phe Ala Arg Met Val Asp Tyr Leu Gly Glu Arg
            115                 120                 125

Gln Gln Ala Ser Gly Val Arg Leu Leu Trp Gly Thr Ala Asn Leu Phe
            130                 135                 140

Ser His Pro Arg Phe Ala Ala Gly Ala Ala Thr Asn Pro Asn Pro Asp
145                 150                 155                 160

Val Phe Ala Trp Ala Ala Thr Gln Val Cys His Ala Leu Asp Ala Thr
                165                 170                 175

His Arg Leu Gly Gly Glu Asn Tyr Val Leu Trp Gly Gly Arg Glu Gly
            180                 185                 190

Tyr Glu Thr Leu Leu Asn Thr Asp Leu Lys Arg Glu Arg Asp Gln Phe
            195                 200                 205

Ala Arg Phe Leu Ser Met Val Val Glu His Lys His Arg Ile Gly Phe
            210                 215                 220

Lys Gly Ala Leu Leu Ile Glu Pro Lys Pro Gln Glu Pro Thr Lys His
225                 230                 235                 240

Gln Tyr Asp Tyr Asp Val Ala Thr Val His Gly Phe Leu Val Gln Tyr
                245                 250                 255

Gly Leu Gln Asn Glu Ile Arg Val Asn Ile Glu Ala Asn His Ala Thr
            260                 265                 270

Leu Ala Gly His Ser Phe His His Glu Ile Ala Asn Ala Phe Ala Leu
            275                 280                 285

Gly Val Phe Gly Ser Val Asp Ala Asn Arg Gly Asp Pro Gln Asn Gly
            290                 295                 300

Trp Asp Thr Asp Gln Phe Pro Asn Ser Val Glu Glu Leu Thr Leu Ala
305                 310                 315                 320

Phe Tyr Glu Ile Leu Arg His Gly Gly Phe Thr Thr Gly Gly Met Asn
            325                 330                 335

Phe Asp Ala Lys Val Arg Arg Gln Ser Ile Asp Pro Glu Asp Leu Phe
            340                 345                 350

Tyr Gly His Val Gly Ala Ile Asp Val Leu Ala Leu Ala Leu Glu Arg
            355                 360                 365

Ala Ala Val Leu Val Glu Asn Asp Arg Leu Asp Ala Leu Arg Arg Gln
            370                 375                 380

Arg Tyr Ala Gln Trp Asp Ala Phe Gly Arg Lys Ile Leu Ala Gly
385                 390                 395                 400

Gly Tyr Thr Leu Glu Ser Leu Ala Ala Asp Ala Leu Ala Arg Gly Val
            405                 410                 415

Asp Pro Gln His Ala Ser Gly Ala Gln Glu Arg Leu Glu Asn Ile Val
            420                 425                 430

Asn Gln Ala Ile Tyr Gly Leu Arg
            435                 440

<210> SEQ ID NO 17
<211> LENGTH: 438
<212> TYPE: PRT
<213> ORGANISM: Clostridium phytofermentans

<400> SEQUENCE: 17

Met Lys Asn Tyr Phe Pro Asn Val Pro Glu Val Lys Tyr Glu Gly Pro

-continued

```
1               5                   10                  15
Asn Ser Thr Asn Pro Phe Ala Phe Lys Tyr Tyr Asp Ala Asn Lys Val
                20                  25                  30

Val Ala Gly Lys Thr Met Lys Glu His Cys Arg Phe Ala Leu Ser Trp
            35                  40                  45

Trp His Thr Leu Cys Ala Gly Ala Asp Pro Phe Gly Val Thr Thr
        50                  55                  60

Met Asp Arg Thr Tyr Gly Asn Ile Thr Asp Pro Met Glu Leu Ala Lys
65                  70                  75                  80

Ala Lys Val Asp Ala Gly Phe Glu Leu Met Thr Lys Leu Gly Ile Glu
                85                  90                  95

Phe Phe Cys Phe His Asp Ala Asp Ile Ala Pro Glu Gly Asp Thr Phe
                100                 105                 110

Glu Glu Ser Lys Lys Asn Leu Phe Glu Ile Val Asp Tyr Ile Lys Glu
            115                 120                 125

Lys Met Asp Gln Thr Gly Ile Lys Leu Leu Trp Gly Thr Ala Asn Asn
130                 135                 140

Phe Ser His Pro Arg Phe Met His Gly Ala Ser Thr Ser Cys Asn Ala
145                 150                 155                 160

Asp Val Phe Ala Tyr Ala Ala Ala Lys Ile Lys Asn Ala Leu Asp Ala
                165                 170                 175

Thr Ile Lys Leu Gly Gly Lys Gly Tyr Val Phe Trp Gly Gly Arg Glu
            180                 185                 190

Gly Tyr Glu Thr Leu Leu Asn Thr Asp Leu Gly Leu Glu Leu Asp Asn
            195                 200                 205

Met Ala Arg Leu Met Lys Met Ala Val Glu Tyr Gly Arg Ala Asn Gly
210                 215                 220

Phe Asp Gly Asp Phe Tyr Ile Glu Pro Lys Pro Lys Glu Pro Thr Lys
225                 230                 235                 240

His Gln Tyr Asp Phe Asp Thr Ala Thr Val Leu Ala Phe Leu Arg Lys
                245                 250                 255

Tyr Gly Leu Glu Lys Asp Phe Lys Met Asn Ile Glu Ala Asn His Ala
            260                 265                 270

Thr Leu Ala Gly His Thr Phe Glu His Glu Leu Ala Met Ala Arg Val
            275                 280                 285

Asn Gly Ala Phe Gly Ser Val Asp Ala Asn Gln Gly Asp Pro Asn Leu
            290                 295                 300

Gly Trp Asp Thr Asp Gln Phe Pro Thr Asp Val His Ser Ala Thr Leu
305                 310                 315                 320

Ala Met Leu Glu Val Leu Lys Ala Gly Gly Phe Thr Asn Gly Gly Leu
                325                 330                 335

Asn Phe Asp Ala Lys Val Arg Arg Gly Ser Phe Glu Phe Asp Asp Ile
            340                 345                 350

Ala Tyr Gly Tyr Ile Ala Gly Met Asp Thr Phe Ala Leu Gly Leu Ile
            355                 360                 365

Lys Ala Ala Glu Ile Ile Asp Asp Gly Arg Ile Ala Lys Phe Val Asp
            370                 375                 380

Asp Arg Tyr Ala Ser Tyr Lys Thr Gly Ile Gly Lys Ala Ile Val Asp
385                 390                 395                 400

Gly Thr Thr Ser Leu Glu Glu Leu Glu Gln Tyr Val Leu Thr His Ser
                405                 410                 415

Glu Pro Val Met Gln Ser Gly Arg Gln Glu Val Leu Glu Thr Ile Val
            420                 425                 430
```

Asn Asn Ile Leu Phe Arg
        435

<210> SEQ ID NO 18
<211> LENGTH: 437
<212> TYPE: PRT
<213> ORGANISM: Piromyces sp.
<220> FEATURE:
<221> NAME/KEY: misc_feature
<223> OTHER INFORMATION: xylose isomerase

<400> SEQUENCE: 18

Met Ala Lys Glu Tyr Phe Pro Gln Ile Gln Lys Ile Lys Phe Glu Gly
1               5                   10                  15

Lys Asp Ser Lys Asn Pro Leu Ala Phe His Tyr Tyr Asp Ala Glu Lys
            20                  25                  30

Glu Val Met Gly Lys Lys Met Lys Asp Trp Leu Arg Phe Ala Met Ala
        35                  40                  45

Trp Trp His Thr Leu Cys Ala Glu Gly Ala Asp Gln Phe Gly Gly Gly
    50                  55                  60

Thr Lys Ser Phe Pro Trp Asn Glu Gly Thr Asp Ala Ile Glu Ile Ala
65                  70                  75                  80

Lys Gln Lys Val Asp Ala Gly Phe Glu Ile Met Gln Lys Leu Gly Ile
                85                  90                  95

Pro Tyr Tyr Cys Phe His Asp Val Asp Leu Val Ser Glu Gly Asn Ser
            100                 105                 110

Ile Glu Glu Tyr Glu Ser Asn Leu Lys Ala Val Val Ala Tyr Leu Lys
        115                 120                 125

Glu Lys Gln Lys Glu Thr Gly Ile Lys Leu Leu Trp Ser Thr Ala Asn
    130                 135                 140

Val Phe Gly His Lys Arg Tyr Met Asn Gly Ala Ser Thr Asn Pro Asp
145                 150                 155                 160

Phe Asp Val Val Ala Arg Ala Ile Val Gln Ile Lys Asn Ala Ile Asp
                165                 170                 175

Ala Gly Ile Glu Leu Gly Ala Glu Asn Tyr Val Phe Trp Gly Gly Arg
            180                 185                 190

Glu Gly Tyr Met Ser Leu Leu Asn Thr Asp Gln Lys Arg Glu Lys Glu
        195                 200                 205

His Met Ala Thr Met Leu Thr Met Ala Arg Asp Tyr Ala Arg Ser Lys
    210                 215                 220

Gly Phe Lys Gly Thr Phe Leu Ile Glu Pro Lys Pro Met Glu Pro Thr
225                 230                 235                 240

Lys His Gln Tyr Asp Val Asp Thr Glu Thr Ala Ile Gly Phe Leu Lys
                245                 250                 255

Ala His Asn Leu Asp Lys Asp Phe Lys Val Asn Ile Glu Val Asn His
            260                 265                 270

Ala Thr Leu Ala Gly His Thr Phe Glu His Glu Leu Ala Cys Ala Val
        275                 280                 285

Asp Ala Gly Met Leu Gly Ser Ile Asp Ala Asn Arg Gly Asp Tyr Gln
    290                 295                 300

Asn Gly Trp Asp Thr Asp Gln Phe Pro Ile Asp Gln Tyr Glu Leu Val
305                 310                 315                 320

Gln Ala Trp Met Glu Ile Ile Arg Gly Gly Gly Phe Val Thr Gly Gly
                325                 330                 335

Thr Asn Phe Asp Ala Lys Thr Arg Arg Asn Ser Thr Asp Leu Glu Asp

Ile Ile Ile Ala His Val Ser Gly Met Asp Ala Met Ala Arg Ala Leu
340                     345                 350
        355                 360                 365

Glu Asn Ala Ala Lys Leu Leu Gln Glu Ser Pro Tyr Thr Lys Met Lys
    370                 375                 380

Lys Glu Arg Tyr Ala Ser Phe Asp Ser Gly Ile Gly Lys Asp Phe Glu
385                 390                 395                 400

Asp Gly Lys Leu Thr Leu Glu Gln Val Tyr Glu Tyr Gly Lys Lys Asn
                405                 410                 415

Gly Glu Pro Lys Gln Thr Ser Gly Lys Gln Glu Leu Tyr Glu Ala Ile
            420                 425                 430

Val Ala Met Tyr Gln
        435

<210> SEQ ID NO 19
<211> LENGTH: 20
<212> TYPE: DNA
<213> ORGANISM: Artificial
<220> FEATURE:
<223> OTHER INFORMATION: forward degenerate primer

<400> SEQUENCE: 19
ttytggggwg ghmgdgargg                                              20

<210> SEQ ID NO 20
<211> LENGTH: 20
<212> TYPE: DNA
<213> ORGANISM: Artificial
<220> FEATURE:
<223> OTHER INFORMATION: reverse degenerate primer
<220> FEATURE:
<221> NAME/KEY: misc_feature
<222> LOCATION: (9)..(9)
<223> OTHER INFORMATION: n is a, c, g, or t

<400> SEQUENCE: 20
aaytsrtcng trtcccadcc                                              20

<210> SEQ ID NO 21
<211> LENGTH: 1317
<212> TYPE: DNA
<213> ORGANISM: Artificial
<220> FEATURE:
<223> OTHER INFORMATION: Codon optimized sequence encoding
      Lachnoclostridium phytofermentans XI

<400> SEQUENCE: 21
atgaagaact acttcccaaa cgttccagaa gttaagtacg aaggtccaaa ctctaccaac     60
ccattcgctt tcaagtacta cgacgctgaa agaattgttg ctggtaagac catgaaggaa    120
cactgtagat cgctttgtc ttggtggcac actttgtgtg ctggtggtgc tgacccattc    180
ggtgttacta ctatggacag atcttacggt aacattaccg acccaatgga attcgctaag    240
gctaaggttg acgctggttt cgaattgatg accaagttgg gtattgaata cttctgtttc    300
cacgacgctg acattgctcc agaaggtgaa aacttcgaag aatctaagaa gaacttgttc    360
gttattgttg actacattaa ggaaagatga gaccaaaccg gtattaagtt ggtgtggggt    420
accgctaaca acttcggtca cccaagattc atgcacggtg cttctacttc ttgtaacgct    480
gacgttttcg cttacgctgc tgctaagatt aagaacgctt tggacgctac tattaagttg    540
ggtggtaagg gttacgtttt ctggggtggt agagaaggtt acgaaacttt gttgaacact    600

```
gacttgggtt tggaattgga caacatggct agattgatga agatggctgt tgaatacggt    660
agagctaacg gtttcgacgg tgacttctac attgaaccaa agccaaagga accaactaag    720
caccaatacg acttcgacac tgctactgtt ttgggtttct tgagaaagta cggtttggaa    780
aaggacttca agatgaacat tgaagctaac cacgctacct tggctggtca cactttcgaa    840
cacgaattgg ctttggctag agttaacggt gttttcggtt ctgttgacgc taaccaaggt    900
gacccaaact ggggttggga cactgaccaa ttcccaaccg acgttcactc tgctaccttg    960
gctatgttgg aagttttgaa ggctggtggt ttcactaacg gtggtttgaa cttcgacgct   1020
aaggttagaa gaggttcttt cgaattcgac gacattgctt acggttacat tgctggtatg   1080
gacaccttcg ctttgggttt gattaaggct gctgaaatta ttgaagacgg tagaattgct   1140
aagttcgttg aagacagata cgcttcttac aagaccggta ttggtaaggc tattgttgac   1200
ggtactactt ctttggaaga attggaacaa tacgttttga cccacaacga accagttatg   1260
caatctggta gacaagaagt tttggaatct attgttaaca acattttgtt cagataa      1317
```

<210> SEQ ID NO 22
<211> LENGTH: 1344
<212> TYPE: DNA
<213> ORGANISM: Artificial
<220> FEATURE:
<223> OTHER INFORMATION: Codon optimized sequence encoding Clostridium
      algidicarnis XI

<400> SEQUENCE: 22

```
atgaaggaat acttcaaggg tattccagaa gttaagtacg aaggtaagga ctctattaac     60
ccattcgctt tcaagttcta cgacgctaag agagttattg acggtaagtc tatggaagaa    120
cacttgaagt cgctatgtc ttggtggcac accatgactg ctactggtac tgacccattc    180
ggtgctggta ctattgacag aaactacggt caaactgaat ctatggaaat tgctagagct    240
aaggttgacg ctgctttcga attgatgaag aagttgggta ttaagtactt ctgtttccac    300
gacgttgaca ttgttccaga aggtaaggac ttgaaggaaa ctaaggaaaa cttgtctgtt    360
attgttgact acattgaaga aaagatgaag ggtactgaca ttaagttgtt gtggggtacc    420
gctaactgtt tctcttctcc aagatacatg cacggtgctg gtacttcttg taacgctgac    480
tctttctctt acgctgcttc tcaaattaag aacgctattg acgctaccat tcaattgggt    540
ggttctggtt acgttttctg gggtggtaga gaaggttacg aaaccttgtt gaacactgac    600
atgggtttcg aattggacaa catggctaga ttgatgaaga tggctgttaa gtacgctaga    660
aagaagggtt caacggtga cttctacatt gaaccaaagc caaggaacc aactaagcat    720 caatacgact tcgacgctgc tactgttatt ggtttcttgc gtaagtacga cttgatggac    780
gacttcaagt tgaacattga agctaaccac gctactttgg ctggtcacac cttcccacac    840
gaattggctg ttgctagaat aacggtgtt ttcggttctg ttgacgctaa ccaaggtgac    900
tctttgttgg gttgggacac cgaccaattc ccaaccgacg ttaaggaagc taccttgtct    960
atgttggaaa ttattaaggc tggtggtttc actaacggtg gtttgaactt cgacgctaag   1020
gttagaagac catctttcac tttcgaagac attgttacg gttacatttc tggtatggac   1080 acttcgcct gggtttgat taaggcttac gaagttattg aagacggtag aattgacgaa   1140
ttcattgaaa agagatacgc ttcttacgaa tctggtattg gtaagaagat tttaaacaac   1200
gaagttacct tggaagaatt ggaagcttac actttggaaa acaaggaaag accaatggaa   1260
tctggtagac aagaatactt ggaaccattt ttgaaccaaa ttttgtacaa gtaatatcga   1320
```

```
taccgtcgac ctcgagtcat gtaa                                          1344
```

<210> SEQ ID NO 23
<211> LENGTH: 1323
<212> TYPE: DNA
<213> ORGANISM: Artificial
<220> FEATURE:
<223> OTHER INFORMATION: Codon optimized sequence encoding
      Mageeibacillus indolicus XI

<400> SEQUENCE: 23

```
atgaagttct tcgaaaacgt tccaaaggtt aagtacgaag gttctaagtc taccaaccca     60
ttcgctttca gtactacaa cccagaagct gttattgctg gtaagaagat gaaggaccac    120
ttgaagttcg ctatgtcttg gtggcacact atgaccgcta ctggtcaaga ccaattcggt    180
tctggtacca tgtctagaat ttacgacggt caaactgaac cattggcttt ggctaaggct    240
agagttgacg ctgctttcga cttcatggaa aagttgaaca ttgaatactt ctgtttccac    300
gacgctgact ggctccaga aggtaactct ttgcaagaaa gaaacgaaaa cttgcaagaa    360
atggtttctt acttgaagca aaagatggct ggtacctcta ttaagttgtt gtggggtact    420
tctaactgtt tctctaaccc aagattcatg cacggtgctg ctacttcttg tgaagctgac    480
gttttcgctt ggactgctac tcaattgaag aacgctattg acgctactat tgctttgggt    540
ggtaagggtt acgttttctg gggtggtaga gaaggttacg aaaccttgtt gaacactgac    600
gttggtttgg aaatggacaa ctacgctaga atgttgaaga tggctgttgc ttacgctaga    660
tctaagggtt acaccggtga cttctacatt gagccaaagc caaggaacc aaccaagcac    720
caatacgact tcgacgttgc tacctgtgtt gctttcttgg aaaagtacga cttgatgaga    780
gacttcaagg ttaacattga agctaaccac gctaccttgg ctggtcacac cttccaacac    840
gaattgagaa tggctagaac cttcggtgtt ttcggttctg ttgacgctaa ccaaggtgac    900
tctaacttgg gttgggacac cgaccaattc ccagtaaca tttacgacac tactttggct    960
atgtacgaaa ttttgaaggc tggtggtttc actaacggtg gtttgaactt cgacgctaag   1020
gttagaagac catctttcac cccagaagac attgcttacg cttacatttt gggtatggac   1080
actttcgctt ggtttgat taaggctcaa caattgattg aagacggtag aattgacaga   1140
ttcgttgctg aaaagtacgc ttcttacaag tctggtattg gtgctgaaat tttgtctggt   1200
aagacttctt tgccagaatt ggaagcttac gctttgaaga agggtgaacc aaagttgtac   1260
tctggtagac aagaatactt ggaatctgtt gttaacaacg ttattttcaa cggtaacttg   1320
taa                                                               1323
```

<210> SEQ ID NO 24
<211> LENGTH: 1356
<212> TYPE: DNA
<213> ORGANISM: Artificial
<220> FEATURE:
<223> OTHER INFORMATION: Codon optimized sequence encoding Ruminococcus
      sp. NK3A76 XI

<400> SEQUENCE: 24

```
atggctgaat tcttcgctaa cattccaaag attaagtacg aaggtccaca atctactaac     60
ccattggctt tcaagtacta caacccagac gaagttattg gtggtaagac catgaaggaa    120
caattgagat tcgctttgtc ttggtggcac actatgggtg gtgacggtac cgacatgttc    180
ggttgtggta ccactgacaa gacttggggt gaagcttctc agaagctag agctaaggct    240
aaggttgacg ctgctttcga aattatggac aagttgtcta ttgactactt ctgttaccac    300
```

```
gacagagaca tttctccaga atacggttct tgaaggaaa ccaacgaaaa gttcgacgaa      360
ttgattgact acattgctga aaagatgaag gctgacccat ctaagaagtt gttgtggggt      420
actgctaagt gtttcgacca cccaagatac atgcacggtg ctggtacttc tccatctgct      480
gacgttttcg cttacgctgc tgctcaaatt aagaaggcta ttgactctac tattaagttg      540
ggtggtaagg gttacgtttt ctggggtggt agagaaggtt acgaaacttt gttgaacacc      600
aacatgggtt tggaattgga caacatggct agattgatga gatggctgt tgaatacgct      660 agatctaagg gttacgacgg tgacttctac attgaaccaa agccaaagga accaaccaag      720
caccaatacg acttcgacac tgctactgtt attggtttct tgagaaagta cggtttggac      780
aaggacttca agatgaacat tgaagctaac cacgctactt tggctcaaca cactttccaa      840
cacgaattga gagttgctag agacaacggt tccttcggtt ctattgacgc taaccaaggt      900
gacccattgt tgggttggga cactgaccaa ttcccaacca acgcttacga cgctaccttg      960
tgtatgtacg aagttattaa ggctggtggt ttcactaacg gtggtttgaa cttcgacgct     1020
aaggctagaa gaggttctta caccttggac gacatttttct actcttacat tgctggtatg     1080
gacactttcg ctttgggttt gagagctgct acaagttga ttgaagacgg tagagttgac     1140
aagttcgttg acgacagata cgcttcttgg aacactggta tcggtaagga cattattgac     1200
ggtaaggttg gtttcgaaga attggaaaag tacgctttgg aaaagggtga agttactgac     1260
tctttgactt ctggtagaca agaatacttg gaatctgttt tgaaccaaat tatgttcact     1320
ttgtaatatc gataccgtcg acctcgagtc atgtaa                                1356

<210> SEQ ID NO 25
<211> LENGTH: 1347
<212> TYPE: DNA
<213> ORGANISM: Artificial
<220> FEATURE:
<223> OTHER INFORMATION: Codon optimized sequence encoding Epulopiscium
      sp. 'N.t. morphotype B XI

<400> SEQUENCE: 25
atggttaacg gttttgactaa cattccacca gttaagttcg aaggtagaga ctctaagaag       60
gctttgtctt tcaagtacta caacccagac gaaatgattc aaggtaagaa gatgaaggac      120
tacttgaagt tcgctatgtc ttactggcac accttgtgtg gtgacggtac tgacccattc      180
ggttcttcta ctattgacag agactactct ggtcaaactc aatggaaaa ggctaagacc      240 aaggctgacg ttgctttcgc tttgatgcaa attttgggta ttgaatactt ctgtttccac      300
gacttggaca ttgctccaac tggtaactct tgaaggaat tgaagaacaa cttgattgaa      360
attactgact acattaaggg tttgatggac aagactggta ttaagttgtt gtgggggtact      420 gctaactgtt tctctcaccc aagatacatg aacggtgctg gtacttctcc acaagctgac      480
attttcgctt gtgctgctgc tcaaattaag aacgctattg acgctaccat taagttgggt      540
ggtactggtt acgtttttctg gggtggtaga gagggttacg aaaccttgtt gaacaccaac      600
atggaaattg aattggacaa catggctaag ttgatgcaca tggctgttga ctacgctaga      660 tctaaggggtt tcaccggtga cttctacatt gaaccaaagc caaaggaacc aactaagcac      720
caatacgact tcgacgttgc tactgttgtt ggtttcttga gaagtacgg tttggacaag      780 gacttcaaga tgaacattga agctaaccac gctaccttgg ctggtcacac cttccaacac      840 gaattgaactg ttgctagagt taacaacgtt tccgttcta ttgacgctaa ccaaggtgac      900
ttgttgttgg gttgggacac tgaccaattc ccaaccaacg tttacgacac cactttgtgt      960
```

```
atgttggaag ttattaaggc tggtggtttc accaacggtg gtttgaactt cgacgctaag    1020
gttagaagag cttcttacac catggaagac attattttgg cttacatttc tggtatggac    1080
actttcgctt tgggtttgaa gattgctaac aagattattg aagacggtag aattgacgaa    1140
ttcgtttcta aagatacgc ttcttacaag actggtattg tgctgacat tattgctggt    1200 agaaccaact tggaagaatt ggaaaagtac gctttggaat tgccaccagt tgaaccacac    1260
ccaggtaagc aagaatactt ggaagctgtt ttcaacaacg ttatgttcac cgtttaatat    1320
cgataccgtc gacctcgagt catgtaa                                        1347
```

<210> SEQ ID NO 26
<211> LENGTH: 1344
<212> TYPE: DNA
<213> ORGANISM: Artificial
<220> FEATURE:
<223> OTHER INFORMATION: Codon optimized sequence encoding Alkaliphilus metalliredigens XI

<400> SEQUENCE: 26

```
atgagagaac acttcttgga aattaacaag attaagttcg aaggtggtga ctctactaac    60
ccattggctt tcaagtacta cgacgctaac agaattgttc tggtaagaa gatgaaggac    120 cacttgagat cgctttgtc ttactggcac actttgactg gtaacggtac tgacccattc    180
ggtcaaccaa ccatggaaag agactacaac tctttggacg gtattgaatt gtctaaggct    240
agagttgacg ctgctttcga attgatgact aagttgggta ttgaattctt ctgtttccac    300
gacttggaca ttgctccaga aggtaactct ttgcaagaaa agttggacaa cttggacacc    360
attttggaaa gaattgaaga caagatgaag gaaactggta ttaagtgttt gtggggtacc    420
accaacgctt tctctcaccc aagattcatg acggtgctg ctacctctcc aaacgctgat    480
gttttcgctt cgctgctgc tcaagttaag aaggctttgg aaattactca cagattgaga    540
ggtgaaaact acgttttctg gggtggtaga aaggttacg aaaccttgtt gaacactgac    600
attgctttgg aaaacgacaa cttggctaag ttcttgaaga tggctaagga ctacgctaga    660
aacattggtt cgaaggtca attcttgatt gaaccaaagc caaaggaacc aactaagcac    720
caatacgact tcgacactat gactgttttg ggtttcttga aaagtacaa cttgattgac    780 gacttcaagt tgaacattga agctaaccac gctaccttgg ctggtcacac tttccaacac    840
gaattggcta tggctagaat taacggtgtt ttgggttctg ttgacgctaa ccaaggtgac    900
ttgttgttgg gttgggacac tgaccaattc ccaaccaaca tttacgacgc taccttgtct    960
atgtacgaag ttttgaagaa cggtggtatt gctccaggtg gtttgaactt cgacgctaag    1020
gttagaagag gttctttcaa gccagacgac ttgttcattg cttacattgt tggtatggac    1080
actttcgcta agggtttgtt ggttgctgac aagttgttga ccgacggtgt tttggaaaac    1140
ttcgttacca agagatacga atcttacact gctggtattg gtaagaagat tattgaagac    1200
gctacctctt tcgaagaatt ggctgaatac gctttgaagc acgacaagat tgttttggaa    1260
tctggtagac aagaaatgtt ggaagacatt gttaacagat acatttacaa gtaatatcga    1320
taccgtcgac ctcgagtcat gtaa                                           1344
```

<210> SEQ ID NO 27
<211> LENGTH: 1323
<212> TYPE: DNA
<213> ORGANISM: Artificial
<220> FEATURE:
<223> OTHER INFORMATION: Codon optimized sequence encoding Eubacterium sp. CAG:180 XI

<400> SEQUENCE: 27
atgtacttca acaacattga aaagattaag ttcgaaggtg ttaactctaa gaacccattg 60
gctttcaagt actacgacgc tgacagaatt attgctggta agaagatgtc tgaacacttg 120
aagttcgcta tgtcttactg gcacaccatg tgtgctgacg gtactgacat gttcggtaga 180
ggtactatta acaagtcttt cggtggtaag actgctattg aaatttacga acacaaggtt 240
tacgctgctt tcgaattgat ggaaaagttg ggtatgcaat acttctgttt ccacgacaga 300
gacattgctc cagaaggtgc tactttgaag gaaactaacg aaaacttgga aagaattgtt 360
ccaattatta agtctgaaat gaagagaacc ggtattaagt tgttgtgggg taccgctaac 420
tgtttcaacc acccaagata catgtgtggt gctggtaccg ctccatctgc tgacgttttc 480
gcttacgctg ccgctcaaat taagaaggct attgaaatta ccgttgaatt gggtggtcaa 540
ggttacgttt tctggggtgg tagagaaggt tacgacacca ttttgaacac tgacatggct 600
aaggaacaag acaacatggc ttacttgatg agaatggctg ttgactacgg tagatctatt 660
ggtttcactg gtgacttcta cattgaacca aagccaaagg aaccaactaa gcaccaatac 720
gacttcgacg tttctactgt tttggctttc ttgagaaagt acgacttgga caaggacttc 780
aagatgaaca ttgaagctaa ccacgctact ttggctggtc acaccttcca acacgaattg 840
agagttgcta gagacaacgg tgttttcggt tctattgacg ctaaccaagg tgacatgttg 900
ttgggttggg acaccgacca attcccaact gacttgtact ctaccactat gtgtatgtac 960
gaagttttga agcaaggtgg tttcaccaac ggtggtttga acttcgacgc taaggctaga 1020
agagcttcta acacttacga agacgttttc ttgtcttaca ttgctggtat ggacgctttc 1080
gcttacggtt tgattgttgc tgacaagatt atttctgacg gtgttatgga caagttcgtt 1140
gaaaacagat actcttctta caccgaaggt attggtaaga agattgctga caagcaaacc 1200
tctttggctg aattggaaca atacactttg accaacggtg aaccaactgc tgaatctggt 1260
aagcaagaat acttggaagc tttggttaac caatacatta tttctgctgg tagagaattg 1320
taa 1323

<210> SEQ ID NO 28
<211> LENGTH: 1320
<212> TYPE: DNA
<213> ORGANISM: Artificial
<220> FEATURE:
<223> OTHER INFORMATION: Codon optimized sequence encoding Clostridium saccharoperbutylacetonicum XI

<400> SEQUENCE: 28
atgaaggaat acttcggtaa cgtttctaag attaactacg aaggtccagg ttctaagaac 60
ccatactctt tcaagtacta caacccagac gaagttattg gtggtaagac catgaaggaa 120
cacttgagat tctctttgtc ttactggcac actttgactg ctaacggtgc tgacccattc 180
ggtgctggta ccatgttgag accatgggac gacattacta acgaaatgga cttggctaag 240
gctagaatgg aagctgcttt cgaattgatg gacaagttga acattgaata cttctgtttc 300
cacgacagag acattgctcc agaaggtaag actttgcaag aaactaacga aaacttggac 360
gaaattgttg cttactgtaa ggaattgatg aagaagtaca acaagaagtt gttgtggggt 420
actgctaact gcttcaccaa cccaagatac gttcacggtg ctggtacttc ttgtaacgct 480
gacgttttcg cttacgctgc tgctcaaatt aagaaggctt tggaagttac taaggaattg 540

-continued ggtggtgaaa actacgtttt ctggggtggt agagaaggtt acgaaacctt gttaaacact 600
gacatgggtt tggaattgga caacttcgct cgtttgttgc aaatggctgt tgactacgct 660
aaggaaattg gtttcactgg tcaattcttg attgaaccaa agccaaagga accaactaag 720
catcaatacg acttcgacac cgctaccgtt ttgggtttct tgaagaagta caacttggac 780
aagtacttca aggttaacat tgaagctaac cacgctactt tggctcaaca cactttccaa 840
cacgaattga acttcgctag aattaacaac ttcttgggtt ctattgacgc taaccaaggt 900
gacccaatgt tgggttggga tactgaccaa ttcccaacta acatttacga cgctaccttg 960
gctatgtacg aaattttgaa gaacggtggt ttggctccag gtggtgttaa cttcgacgct 1020
aaggtcagaa gagcttcttt cgaaaaggaa gacttgttct tggcttacat tgctggtatg 1080
gacactttcg ctaagggttt gaaggttgct cacaagttgt tggaaaacgg tgaattggaa 1140
aacttcatta agaacaagta cgcttctttc tctgaaggta ttggtaagga aattgttgaa 1200
ggtaaggttg gtttgaagga attggaagct tacgctttga agaacaacga aattaccaac 1260
aagtctggta gacaagaatt gttggaagct attgttaacc aatacatttt cgaagactaa 1320

<210> SEQ ID NO 29
<211> LENGTH: 1311
<212> TYPE: DNA
<213> ORGANISM: Artificial
<220> FEATURE:
<223> OTHER INFORMATION: Codon optimized sequence encoding Fusobacterium mortiferum XI

<400> SEQUENCE: 29
atggaattct tcaagggtat tgacaaggtt aagtacgaag gtgttaagac taacaacttg 60
ttggctttcg ctcactacaa cccagaagaa gttattttgg gtaagaagat gaaggaccac 120
ttgaagttcg ctatgtctta ctggcacacc ttgactggtg aaggtactga cccattcggt 180
aacgctacta tggacagaga atggaacgaa tacaccccaa tggaaaaggc taaggctaga 240
gttaaggctg gtttcgaatt catggaaaag ttgggtttgg aatacttctg tttccacgac 300
aaggacattg ctccagaagc tgaaactttg gaagaatacc acagaaactt ggacgaaatt 360
gttgacttga ttgaagaaga aatgaagaga actggtatta agttgttgtg gggtacttct 420
aacatgttct ctcacccaag attcatgcac ggtgctgcta cttcttgtaa cgctgacgtt 480
ttcgcttacg ctgctgctca aactaagaag gctttggaaa ttactaagag attgaacggt 540
actggttacg ttttctgggg tggtagagaa ggttacgaaa ctttgttgaa cactgacatt 600
ggtttggaat tggacaactt ggctagattc ttgcaaatgg ctgttgacta cgctaagaag 660
attggtttcg aaggtcaatt cttcattgaa ccaaagccaa aggaaccaac taagcaccaa 720
tacgacttcg acactactac tgttttggaa ttcttgagaa agtacaactt ggacaagtac 780
ttcaagatga acattgaagc taaccacgct accttggctg gtcacacttt ccaacacgaa 840
ttgtgtactg ctagaattaa cggtgttttc ggttctattg acgctaacca aggtgacatg 900
ttgttgggtt gggacactga ccaattccca actaacgttt acgacgctgt tttggctatg 960
tacgaaactt tgttggctgg tggtttcaag gaaggtggtt tgaacttcga cgctaaggtt 1020
agaagaggtt ctttcgaacc aaaggacttg ttctacgctt acatttctgg tatggacacc 1080
ttcgctaagg gtttgaaggt tgctgctaag ttgattgaag acggtacttt cgaaaagatt 1140
aaggttgaaa gatactcttc ttacactact ggtattggta agcaaattgt taacggtgaa 1200
gttggtttcg aagaattgtc taagtacgct ttgaccaacg gtgttaagaa gaactcttct 1260
ggtagacaag aaatgttgga aaacattttg aacagataca tttacgaata a        1311

<210> SEQ ID NO 30
<211> LENGTH: 1320
<212> TYPE: DNA
<213> ORGANISM: Artificial
<220> FEATURE:
<223> OTHER INFORMATION: Codon optimized sequence encoding [Clostridium]
      cellulosi XI

<400> SEQUENCE: 30
atgaaggaat acttctctaa cattccaaag gttagatacg aaggtccaga ctctaagaac    60
ccattcgctt tcaagttcta cacccagaa gaaaagattg ctggtaagac tatgagagaa   120
caattgaagt tctctctttgg ttactggcac accttggacg ctgaaggtac cgacatgttc   180
ggtagagcta ccatggacaa atctttcggt gaaactgacc aatggctat ttacaagaac    240 aaggcttacg ctgctttcga attgatggac aagttggaca ttgactactt ctgtttccac   300
gacagagaca ttgctccaga aggtccaact ttgtctgaaa ctaacaagaa cttggacgaa   360 attgttctctt tgttgaagaa gttgatggct gaacacaaca gaagttgtt gtggggtact   420 gctaacacct tctctcaccc aagatacgtt cacggtgctg gtacttcttg taacgcttct   480
gttttcgctt cgctgctgc tcaaattaag aaggctattg aaattaccaa ggaattggac   540
ggttgtggtt acgttttctg gggtggtaga gaaggttacg aaactttgtt gaacactgac   600
atggaattgg aattggacaa catggctaga ttgttgaaga tggctgttga ctacgctaga   660
tctattggtt tcaagggtga attcttcatt gaaccaaagc caaggaacc aactaagcac   720 caatacgact acgacgtttc tactgttttg ctttcttga gaaagtacgg tttggacaag   780
gttttcaagg ttaacattga agctaaccac gctactttgg ctcaacacac tttccaacac   840
gaattgagag ttgctagaat taacggtgtt ttgggttctg ttgacgctaa ccaaggtgac   900
gttatgttgg ttgggacac tgaccaattc ccaactaacg tttacgacac tgctttggct   960
atgtacgaaa ttttgaagaa cggtggtttg ccatctggtg gtttgaactt cgactctaag  1020
aacagaagag ttctcttcga ccagaagac attttccacg gttcattgc tggtatggac  1080 gctttcgctt tgggtttgag aattgctgac agaatcatta gagacggtag attgaacaa  1140 ttcgttaagg acagatacaa gtcttaccaa tctggtattg gtgctgacat tgttctggt  1200 agagctaaga ttgaagactt ggaaaagtac gctttgaagt tgggtgaagt taacgctatt  1260
ggttctggta gacaagaata cttggaagac attttgaact ctattatgtt cggtaagtaa  1320

<210> SEQ ID NO 31
<211> LENGTH: 1353
<212> TYPE: DNA
<213> ORGANISM: Artificial
<220> FEATURE:
<223> OTHER INFORMATION: Codon optimized sequence encoding
      Cellulosilyticum lentocellum XI

<400> SEQUENCE: 31
atggctgaat tcttcaaggg tattggtgtt attccattcg aaggtgctga ctctgttaac    60
ccattggctt tcaagcacta caacaaggac gaaaaggttg tgacaagac tatggctgaa   120 cacttgagat tcgctatgtc ttactggcac acttgtgtg ctgaaggtgg tgacccattc   180
ggttctacca ctgctgctag accatggaac caaattgcta acccaattga atggctaag   240 gctaaggttg acgctggttt cgaattcatg caaaagttgg gtatcgaata tttctgtttc   300
cacgacagag acattgctcc agaaggtaag gacttggctg aaactaacca aattttggac   360
gaagttgttg cttacattaa ggttaagatg caagaaaccg gtattaagtt gttgtggggt 420
actgctaact gtttcaacaa caagagattc atgcacggtg ctggtactac ttgtaacgct 480
gaagttttcg cttacgctgc tgctcaaatt aagaaggcta ttgaagttac caaggaattg 540
ggtggtgaaa actacgtttt ctggggtggt agagaaggtt acgaaacttt gttgaacact 600
gacactggtt tggaattgga caacttcgct agattgttgc aaatggctgt tgactacgct 660
aaggaaattg gtttcactgg tcaattcttg attgaaccaa agccaaagga accaactaag 720
caccaatacg acttcgacac tgctactgtt ttggcttttct tgagaaagta caacttggac 780
acttacttca agatgaacat tgaagctaac cacgctactt tggctggtca cactttccaa 840
cacgaattga acatgtctag aattaacaac gttttgggtt ctattgacgc taaccaaggt 900
gacttgatgt tgggttggga cactgaccaa ttcccaacta acatttacga cgctactatg 960
gctatgtacg aagttttgaa ggctggtggt attgctccag gtggtttcaa cttcgactct 1020
aaggttagaa gaggttcttt cgaagaagct gacttgttca ttgcttacat tgctggtatg 1080
gacactttcg ctaagggttt gaaggttgct tacaacttgt tgaaggacgg tgttttggaa 1140
gacttcgtcg ctgacagata cgcttccttc aacgagggta tcggtaagga cattgtttct 1200
ggtaacgttg gtttcaagga attggaagct tacgctttga agcaacaacc aattgttaac 1260
aagtctggta gacaagaatg gttggaaact gttgttaacc aatacattta caacaacaag 1320
taatatcgat accgtcgacc tcgagtcatg taa 1353

<210> SEQ ID NO 32
<211> LENGTH: 1338
<212> TYPE: DNA
<213> ORGANISM: Artificial
<220> FEATURE:
<223> OTHER INFORMATION: Codon optimized sequence encoding
Peptoclostridium difficile XI

<400> SEQUENCE: 32
atgtctgaaa ttttcaaggg tattggtcaa attaagttcg aaggtgttaa gtctgacaac 60
gaattggctt tcagatacta caacccagaa caagttgttg gtaacaagac tatgaaggaa 120
cacttgagat tcgctatgtc ttactggcac actttgtgtg gtgaaggtaa cgacccattc 180
ggtgttggta ctgttgaaag accatggaac aacattaccg acccaattga aattgctaag 240
attaaggttg acgctggttt cgaattcatg tctaagatgg gtattgaata cttctgtttc 300
cacgacagag acattgctcc agaaggtaga gacttggaag aaactaacaa gattttggac 360
gaaattgttg aatacattaa ggttaacatg gaaaagactg gtattaagtt gttgtggggt 420
actgctaaca tgttcggtaa cccaagattc gttcacggtg cttctactac ttgtaacgct 480
gacgtttacg cttacgctgc tgctcaagtt aagaaggcta tggaaattac taagtacttg 540
ggtggtgaaa acttcgtttt ctggggtggt agagaaggtt acgaaacttt gttgaacact 600
aacactgaat tggaaatgga caacttcgct agattcttgc aaatggctgt tgactacgct 660
aaggaaattg gtttcactgg tcaattcttg attgaaccaa agccaaagga accaactaag 720
caccaatacg acttcgacac tgctactgtt ttgggtttct tgagaaagta caacttggac 780
aagtacttca agatgaacat tgaagctaac cacgctactt tggctggtca cactttccaa 840
cacgaattga acattgctag aattaacaac gttttgggtt ctattgacgc taaccaaggt 900
gacttgttgt tgggttggga cactgaccaa ttcccaacta acatttacga cgctactttg 960
gctatgtacg aagttttgaa gcaaggtggt attgctccag gtggtttcaa cttcgactct 1020

```
aaggttagaa gagcttcttt cgaagttgaa gacttgttct tggcttacat tgctggtatg    1080
gacactttcg ctaagggttt gttgattgct cacaagttgt tggaagacga agttttcgaa    1140
aacttcacta aggaaagata cgcttctttc tctgaaggta ttggtaagga cattgttgaa    1200
ggtaaggttg gtttcaagga attggaatct tacgctttgc aaatgccagt tattaagaac    1260
aagtctggta gacaagaaat gttggaatct attttgaaca gatacattta cgaagttgac    1320
actatttcta acaagtaa                                                  1338
```

<210> SEQ ID NO 33
<211> LENGTH: 1395
<212> TYPE: DNA
<213> ORGANISM: Artificial
<220> FEATURE:
<223> OTHER INFORMATION: Codon optimized sequence encoding
      (Pepto)clostridium difficile NAP08 XI

<400> SEQUENCE: 33

```
atgtgtaaga ttttgggtgg tcacgaaatg aacgaaattt caagggtat t

-continued

Caldicellulosiruptor acetigenus XI

<400> SEQUENCE: 34

```
atgaagtact tcaaggacat tccagaagtt aagtacgaag gtccacaatc tgacaaccca      60
ttcgctttca agtactacaa cccagacgaa gttattgacg gtaagccatt gaaggaccac     120
ttgagattcg ctattgctta ctggcacact ttctgtgcta ctggttctga cccattcggt     180
caaccaacca ttaacagacc atgggacaag ttctctaacc caatggacaa cgctaaggct     240
agagttgaag ctgctttcga attcttcgaa aagttgaacg ttccattctt ctgtttccac     300
gacagagaca ttgctccaga aggtgaaaac ttgagagaaa ctaacaagaa cttggacgaa     360
attgtttcta tgattaagga atacttgaag acttctaaga ctaaggtttt gtggggtact     420
gctaacttgt tctctcaccc aagatacgtt cacggtgctg ctacttcttg taacgctgac     480
gttttcgctt acgctgctgc tcaagttaag aaggctttgg aagttactaa ggaattgggt     540
ggtgaaaact acgttttctg gggtggtaga gaaggttacg aaactttgtt gaacactgac     600
atggaattgg aattggacaa cttggctaga ttcttgcaca tggctgttga ctacgctaag     660
gaaattggtt tcgacggtca attcttgatt gaaccaaagc caaggaacc aactaagcac      720
caatacgact tcgacgctgc tcacgtttac ggtttcttga agaagtacga cttggacaag     780
tacttcaagt tgaacattga agttaaccac gctaccttgg ctggtcacga cttccaccac     840
gaattgagat tcgctagaat taacaacatg ttgggttcta ttgacgctaa catgggtgac     900
ttgttgttgg gttgggacac tgaccaattc ccaactgacg ttagattgac tactttggct     960
atgtacgaag ttattaagat gggtggtttc gacaagggtg gtttgaactt cgacgctaag    1020
gttagaagag gttctttcga attggaagac ttggttattg gtcacattgc tggtatggac    1080
gctttcgcta agggtttcaa gattgcttac aagttggtta aggacggtgt tttcgacaag    1140
ttcattgaag aaagatacag atcttacaag gaaggtattg gtgctaagat tgtttctggt    1200
caagctgact tcaagacttt ggaagaatac gctttgaact tgtctaagat tgaaaacaag    1260
tctggtaagc aagaattgtt ggaaatgatt ttgaacaagt acatgttctc tgaataatat    1320
cgataccgtc gacctcgagt catgtaa                                         1347
```